United States Patent
Ramanujulu et al.

(10) Patent No.: US 9,422,238 B2
(45) Date of Patent: Aug. 23, 2016

(54) ICMT INHIBITORS

(71) Applicant: National University of Singapore, Singapore (SG)

(72) Inventors: Pondy Murugappan Ramanujulu, Singapore (SG); Tianming Yang, Singapore (SG); Mei-Wang Casey, Singapore (SG); Patrick J. Casey, Singapore (SG); Mei Lin Go, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/404,912

(22) PCT Filed: May 30, 2013

(86) PCT No.: PCT/SG2013/000219
§ 371 (c)(1),
(2) Date: Dec. 1, 2014

(87) PCT Pub. No.: WO2013/180656
PCT Pub. Date: Dec. 5, 2013

(65) Prior Publication Data
US 2015/0218095 A1    Aug. 6, 2015

(30) Foreign Application Priority Data
Jun. 1, 2012  (SG) .................. 201204064

(51) Int. Cl.
*C07D 471/04* (2006.01)
*C07D 209/14* (2006.01)
*C07D 401/04* (2006.01)
*C07D 403/04* (2006.01)

(52) U.S. Cl.
CPC ............ *C07D 209/14* (2013.01); *C07D 401/04* (2013.01); *C07D 403/04* (2013.01); *C07D 471/04* (2013.01)

(58) Field of Classification Search
CPC .................................................. C07D 209/14
See application file for complete search history.

(56) References Cited

U.S. PATENT DOCUMENTS

2011/0039825 A1   2/2011   Ivashchenko et al.
2011/0046368 A1   2/2011   Ivashchenko et al.

FOREIGN PATENT DOCUMENTS

WO   WO-2005/040157   5/2005
WO   WO-2013/180656   12/2013

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
"International Application No. PCT/SG2013/000219, International Search Report mailed Jun. 28, 2013", 5 pgs.
Go, Mei-Lin, et al., "Amino Derivatives of Indole as Potent Inhibitors of Isoprenylcysteine Carboxyl Methyltransferase", J. Med. Chem., 2010, 53 (19), pp. 6838-6850, (Sep. 1, 2010), 6838-6850.
Judd, Weston R., et al., "Discovery and SAR of Methylated Tetrahydropyranyl Derivatives as Inhibitors of Isoprenylcysteine Carboxyl Methyltransferase (ICMT)", J. Med. Chem., 2011, 54 (14), pp. 5031-5047, (Jun. 10, 2011), 5031-5047.
Poste, George, et al., "Chapter 4 Lipid Vesicles as Carriers for Introducing Biologically Active Materials into Cells", Methods in Cell Biology, vol. 14, 1976, pp. 33-71, (1976), 33-71.

* cited by examiner

*Primary Examiner* — Shawquia Jackson
(74) *Attorney, Agent, or Firm* — Schwegman Lundberg & Woessner, P.A.

(57) ABSTRACT

The invention provides a 1,3,5-substituted indole wherein the substituent at position 1 is a C6 to C12 alkyl group; the substituent at position 3 is $CH_2NR^1R^2$ wherein $R^1$ is H or C1 to C3 alkyl, $R^1$ being optionally substituted with —OH, —SH, —$NH_2$ or NHalkyl, wherein alkyl is a C1 to C4 alkyl group, and $R^2$ is C1 to C3 alkyl or $(CH_2)_n$ bonded to position 2 of the indole, wherein n is 1, 2 or 3; and the substituent at position 5 is either an optionally substituted nitrogen containing heteroaromatic ring or an aminosulfonylphenyl group or an alkylsulfonylphenyl group.

18 Claims, 19 Drawing Sheets

Compound 8-12

Cysmethynil (A) 8-12

(B) Cysmethynil

A: 8-12

B: Cysmethynil

Metabolite C

Metabolite D (a) Metabolite A (b) Metabolite B (c) Metabolite C (d) Metabolite D

ICMT INHIBITORS

PRIORITY CLAIM TO RELATED APPLICATIONS

This application is a U.S. national stage application filed under 35 U.S.C. §371 from International Application Serial No. PCT/SG2013/000219, which was filed May 30, 2013, and published as WO 2013/180656 on Dec. 5, 2013, and which claims priority to Singapore Application No. 201204064-8, filed Jun. 1, 2012, which applications and publication are incorporated by reference as if reproduced herein and made a part hereof in their entirety, and the benefit of priority of each of which is claimed herein.

FIELD

The invention relates to analogues of cysmethynil as 1cmt inhibitors.

BACKGROUND

Proteins with a CAAX motif regulate a number of pathways important in oncogenesis. These proteins undergo a series of post-translational modifications that are important for their localization, stability and function. The modifications are initiated by the addition of an isoprenoid moiety (farnesyl or geranylgeranyl) to the cysteine of the CAAX motif by protein farnesyltransferase (FTase) or protein geranylgeranyltransferase-1 (GGTase-1) respectively. This is followed by the endoproteolytic release of the terminal tripeptide (AAX) by RAS converting enzyme (RCE1) and carboxylmethylation of the C-terminal prenylcysteine by isoprenylcysteine carboxyl methyltransferase (Icmt) (FIG. 1).

The most widely studied example of CAAX proteins is the RAS family of regulatory proteins. RAS is a very important molecular switch for a variety of signaling pathways that control diverse processes like cytoskeletal integrity, proliferation, cell adhesion, apoptosis and cell migration. Activating mutations in RAS genes are implicated in the pathogenesis of a large number of solid tumors and hematologic malignancies. In addition, many cancers contain alterations upstream of RAS in signaling cascades and the resultant hyperactivation of RAS is thought to contribute to tumorigenesis.

The possibility of blocking RAS-induced oncogenic transformation by inhibiting the enzymes involved in the post-translational processing of the CAAX motif has been explored for its therapeutic potential. The protein prenyltransferases in particular FTase have been targets of major drug discovery programs. FTase inhibitors showed significant activity in mouse models but clinical trials in cancer patients were disappointing, possibly due to the geranylgeranylation of substrates by GGTase1 when FTase was inhibited. Hence, attention has shifted to the post-prenylation enzymes RCE1 and Icmt as potential therapeutic targets. In particular, there is keen interest in developing Icmt inhibitors in view of studies that showed that genetic and pharmacological intervention with Icmt activity led to significant impairment of oncogenesis in several tumor cell models.

To date, four broad classes of Icmt inhibitors have been investigated. The first class comprises S-adenosylhomocysteine (AdoHcy) and compounds that increase intracellular AdoHcy. AdoHcy is formed when a methyltransferase catalyzes the transfer of the methyl group from S-adenosylmethonine (AdoMet) to the substrate. AdoHcy binds to and competitively inhibits methyltransferase activity. However, AdoHcy is not a selective inhibitor of Icmt and affects the activity of other cellular methyltransferases.

The second class of ICMT inhibitors is structural analogues of the substrate prenylcysteine. Examples are N-acetyl-S-farnesyl-L-cysteine (AFC) and N-acetyl-S-geranylgeranyl-L-cysteine (AGGC). These compounds are competitive inhibitors of Icmt but as structural mimics of the carboxy-terminal prenylcysteine of processed CAAX proteins, they can be expected to affect a large number of processes controlled by CAAX proteins. The more potent analogs identified through these studies are depicted in FIG. 2. Replacement of the amide bond in AFC with the metabolically stable and more drug-like sulphonamide linkage gave A which inhibited Icmt with an $IC_{50}$ of 8.8 µM when evaluated on a vapour diffusion assay. The allylic thioether is deemed to be undesirable due to its chemical and enzymatic lability, thus prompting its replacement with a triazole moiety. The most potent triazole prenyl cysteine analog B has an $IC_{50}$ of 19.4 µM. Another modification involved replacing two of the isoprenoid units in the farnesyl side chain of AFC with an aryl alkyl moiety. C was identified as the most potent analog in that investigation.

The third category comprises small molecule inhibitors of Icmt. The first compound to be identified was cysmethynil (2-[5-(3-methylphenyl)-1-octyl-1H-indolo-3-yl]acetamide) which was discovered through the screening of a diverse chemical library made up of over 70 sub-families with unique scaffolds.

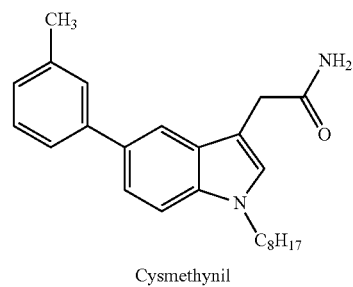

Cysmethynil

It is a competitive inhibitor of the isopenylated cysteine substrate and a non-competitive inhibitor of the methyl donor AdoMet. Inhibition is time dependent and involves the formation of an initial reversible complex with the enzyme (Ki 2.39 µM), followed by a conformational change to give a tighter EI* complex with an overall dissociation constant of 0.11 µM. Cysmethynil caused the mislocation of RAS and impaired epidermal growth factor signaling in cancer cells. It blocked anchorage-independent growth in a colon cancer cell line which was reversed by overexpression of Icmt. Cysmethynil was reported to induce autophagic cell death.

Cysmethynil is poorly soluble and binds strongly to plasma proteins. A quick assessment of its compliance to drug-like filters like the Lipinski's "Rule of Five" and other criteria shows that it exceeds the lipophilic threshold for drug-likeness (Estimated Log P of cysmethynil is 7) and just complies with the cut-off value for rotatable bonds.

In 2011, Judd and co-workers (Judd W R et al. 2011. J Med Chem 54, 5031) investigated the Icmt inhibitory potential of methylated tetrahydropyranyl derivatives and reported 3-methoxy-N-[2-(2,2,6,6-tetramethyl-4-phenyltetrahydropyran-4-yl)ethyl]aniline

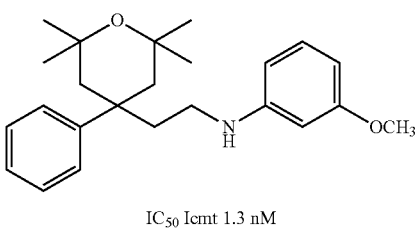

IC$_{50}$ Icmt 1.3 nM 3-methoxy-N-[2-(2,2,6,6-tetramethyl-4-phenyltetrahydro pyran-4-yl)ethyl]aniline as a potent nanomolar inhibitor of Icmt. Icmt inhibition was determined by a fluorometric coupled enzyme assay for SAM-dependent methyl transferase and reconfirmed using the direct radiometric assay which is traditionally used for measuring Icmt inhibition. The compound showed a dose-dependent increase in Ras cytosolic protein and was modestly cytotoxic on several malignant cell lines, irrespective of their Ras status. GI$_{50}$ values ranged from 0.3 to >100 µM. Interestingly, the authors found that a farnesyltransferase inhibitor FTI-2628 was significantly more potent on cells that harbour Ras mutations than those with wild type Ras. Hence they proposed that the inhibition of the prenylation step of CAAX proteins was more effective in reducing cell viability than inhibition of the Icmt-mediated methylation step with this class of small molecule Icmt inhibitors.

S-Farnesyl-thiosalicylic acid to inhibits both Icmt and H-ras driven cell growth. However it was considered that inhibition of ras dependent cell growth was not related to the inhibition of ras methylation by Icmt.

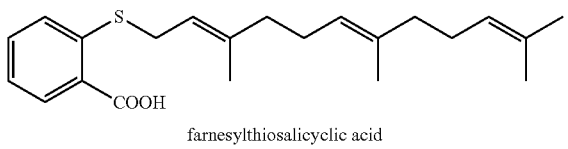 [SMILES: CC(C)=CCC/C(C)=C/CC/C(C)=C/CSc1ccccc1C(=O)O]

farnesylthiosalicyclic acid

The last category of compounds comprises a miscellaneous group of natural products that have been found to possess Icmt inhibitory activity. They range from chemical entitites isolated from marine sponges (spermatinamine, aplysamine 6) to plants (prenylated β hydroxychalcones, a flavanone S-glabrol). Most of these compounds are modest inhibitors (IC$_{50}$>10 µM) and lack drug-like features.

SUMMARY OF INVENTION

In a first aspect of the invention there is provided a 1,3,5-substituted indole wherein:
the substituent at position 1 is C6 to C12 alkyl group;
the substituent at position 3 is CH$_2$NR$^1$R$^2$ wherein R$^1$ is H or C1 to C3 alkyl, R$^1$ being optionally substituted with —OH, —SH, —NH$_2$ or NHalkyl, wherein alkyl is a C1 to C4 alkyl group, and R$^2$ is C1 to C3 alkyl or (CH$_2$)$_n$ bonded to position 2 of the indole, wherein n is 1, 2 or 3; and
the substituent at position 5 is either an optionally substituted nitrogen containing heteroaromatic ring or an aminosulfonylphenyl group or an alkylsulfonylphenyl group.

The following options may be used in conjunction with the first aspect, either individually or in any suitable combination.

The substituent at position 1 may be a straight chain alkyl group. It may be octyl, e.g. n-octyl.

R$^1$ and R$^2$ may both be ethyl. Alternatively R$^1$ may be H or Me and R$^2$ (CH$_2$)$_2$ bonded to position 2 of the indole. In the latter case the indole is a tetrahydrocarboline.

The substituent at position 5 may be a 6-membered heteroaromatic ring. It may contain no heteroatoms other than N. It may contain 1 or 2 ring nitrogen atoms. It may be for example 2-aminopyrimidine-5-yl The indole may have lipophilicity (log D at pH 7.4) of less than about 5. It may have an aqueous solubility of greater than about 10$^{-4}$M at pH 7.4. It may have an IC$_{50MDA-MB-231}$ of less than about 6. It may have an 10$_{50\ PC3}$ of less than about 6.

In an embodiment, there is provided a 1,3,5-substituted indole wherein the substituent at position 1 is octyl; the substituent at position 3 is NEt$_2$; and the substituent at position 5 is either an optionally substituted nitrogen containing heteroaromatic ring having one or two ring nitrogen atoms or an aminosulfonylphenyl group or an alkylsulfonylphenyl group. The substituent at position 5 may be 2-aminopyrimidine-5-yl.

In a further embodiment there is provided a 1,3,5-substituted indole wherein the substituent at position 1 is octyl; the substituent at position 3 is NEt$_2$; and the substituent at position 5 is either an optionally substituted pyridine or pyrimidine ring or a methylaminosulfonylphenyl group or a methylsulfonylphenyl group.

In another embodiment, there is provided a 1,3,5-substituted indole wherein the substituent at position 1 is octyl; the substituent at position 3 is CH$_2$NMeR$^2$ wherein R$^2$ is (CH$_2$)$_2$ bonded to position 2 of the indole; and the substituent at position 5 is either an optionally substituted nitrogen containing heteroaromatic ring or an aminosulfonylphenyl group or an alkylsulfonylphenyl group.

In a further embodiment there is provided a 1,3,5-substituted indole wherein the substituent at position 1 is octyl; the substituent at position 3 is CH$_2$NMeR$^2$ wherein R$^2$ is (CH$_2$)$_2$ bonded to position 2 of the indole; and the substituent at position 5 is either a 2-aminopyrimidine-5-yl group or a 4-methylsulfonylphenyl group. The substituent at position 5 may be 2-aminopyrimidine-5-yl.

In a second aspect of the invention there is provided use of an indole according to the first aspect for any one or more, optionally all, of: inhibiting Icmt activity, treating cancer and inhibiting oncogenesis.

In a third aspect of the invention there is provided a method of treating a cancer comprising administering to a patient in need thereof a therapeutically effective quantity of a compound according to the first aspect.

In a fourth aspect of the invention there is provided use of a compound according to the first aspect for the manufacture of a medicament for the treatment of cancer.

In a fifth aspect of the invention there is provided a composition for treatment of cancer comprising a compound according to the first aspect and one or more pharmaceutically acceptable carriers, diluents or adjuvants.

In a sixth aspect of the invention there is provided a compound according to the first aspect when used for one or more, optionally all, of inhibiting Icmt activity, inhibiting oncogenesis and treating cancer.

In a seventh aspect of the invention there is provided a compound according to the first aspect for use in therapy.

DESCRIPTION OF EMBODIMENTS

Figure 1:
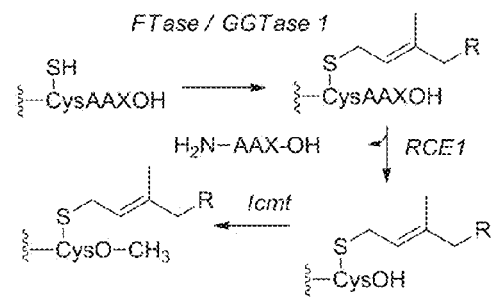
FIG. 1: Post-translational processing of proteins with CAAX motif
Figure 2:
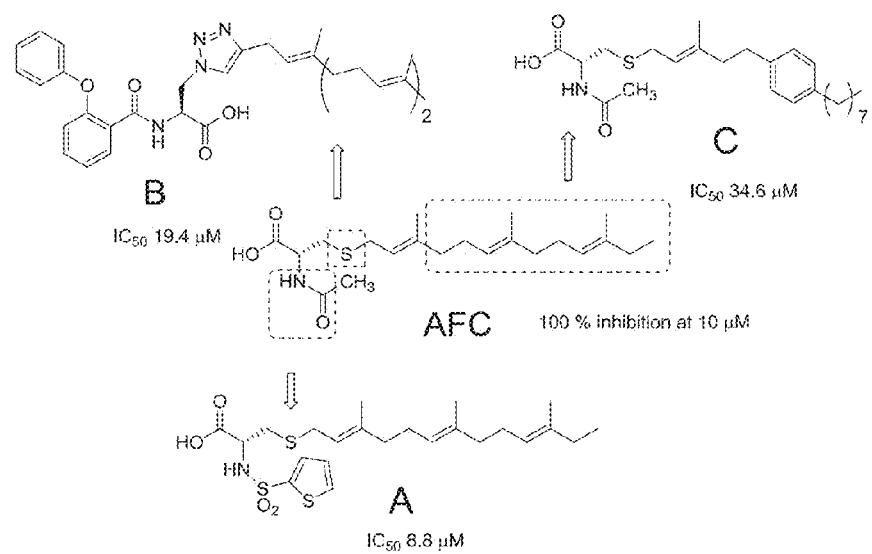
[
FIG. 2: Structures of active ICMT inhibitors that are structural mimics of the minimal substrate AFC

The invention relates to provided 1,3,5-substituted indoles. In the compounds of the invention the substituent at position 1 is C6 to C12 alkyl group; the substituent at position 3 is $CH_2NR^1R^2$ wherein $R^1$ is H or C1 to C3 alkyl and $R^2$ is C1 to C3 alkyl or $(CH_2)_n$ bonded to position 2 of the indole, wherein n is 1, 2 or 3; and the substituent at position 5 is either an optionally substituted nitrogen containing heteroaromatic ring or an aminosulfonylphenyl group or an alkylsulfonylphenyl group.

In some embodiments the indole nucleus has no other substituents other than those specified, i.e. it has no substituents at C4, 6 or 7, and only has a substituent at C2 if $R^2$ is $(CH_2)_n$ bonded to position 2. In other embodiments, other substituents are present.

The substituent at position 1 (i.e. on the indole nitrogen atom) is a C6 to C12 alkyl group. It may for example be C6 to C10, C8 to C12, or C8 to C10. It may be C6, C7, C8, C9, C10, C11 or C12. It may be straight chain or it may be branched chain. It may be non-cyclic. It may for example be n-octyl or isooctyl.

The substituent at position 3 may be a monoalkylaminomethyl group or a dialkylaminomethyl group. In these instances, the alkyl groups may, independently, be methyl, ethyl, propyl or isopropyl. In some embodiments, the alkyl group may be a straight chain alkyl group, i.e. not isopropyl. Alternatively one of the substituents on the amine nitrogen may be an alkylene group, $(CH_2)_n$, which links to position 2 of the indole so as to form a 3-pyrrolidine, 1,2,3,6-tetrahydropyridine or 1-azacyclohept-3-ene ring fused with C2 and C3 of the indole nucleus. In this instance, the other substituent on the amine nitrogen may be hydrogen, methyl, ethyl, n-propyl or isopropyl. In some embodiments, the other substituent on the amine nitrogen may be a straight chain alkyl group, i.e. not isopropyl. The alkyl group of the mono alkylaminomethyl, or either or both of the alkyl groups on the dialkylaminomethyl group independently, may have a heteroatom substituent bearing a hydrogen atom. The substituent may therefore be, for example, —OH, —SH, —NH$_2$, NHalkyl, etc. In this instance, the alkyl group may be a C1 to C4 alkyl group which may be substituted or may be unsubstituted.

The substituent at C5 is an aromatic ring with suitable hydrophilicity. In many embodiments the ring is a 6-membered homoaromatic or heteroaromatic ring, commonly monocyclic, however other options are contemplated. For example it may be a 5-membered heterocycle, a fused homoaromatic and/or heteroaromatic system (e.g. naphthalene, quinoline or naphthiridine ring system) etc. Commonly if a heteroatom is present in the aromatic ring, the only heteroatom will be nitrogen, although in some instances other heteroatoms such as S, O etc. may also be present. Common ring systems include phenyl, pyridyl and pyrimidyl (commonly 5-pyrimidyl). In many instances, although not all, the ring is substituted. Homoaromatic rings are commonly substituted with one sulfonyl group. This may be an alkylsulfonyl group such as methylsulfonyl ($CH_3SO_2$). Other suitable sulfonyl groups include aminosulfonyl groups, optionally substituted on the nitrogen atom. Thus for example methylaminosulfonyl, dimethylaminosulfonyl, ethylaminosulfonyl and diethylaminosulfonyl groups are contemplated. When the C5 substituent is heteroaromatic, it may be a pyridine ring. This may be substituted e.g. by a halogen, or may be unsubstituted. The ring nitrogen atom may be in a 1,2-, 1,3- or 1,4-relationship with the indole ring. The C5 substituent may also be a pyrimidyl ring. In particular it may be a 2-aminopyrimidyl ring or a 2-cyanopyrimidyl ring (commonly bonded to the indole nucleus through C5 of the pyrimidine ring). The amino group of the aminopyrimidine may be primary (i.e. $NH_2$) or may be substituted with 1 or 2 alkyl groups (commonly methyl or ethyl).

The compound of the present invention may have lipophilicity (log D at pH 7.4) of less than about 5, or of less than about 4.8, 4.6, 4.4, 4.2 or 4. It may have an aqueous solubility of greater than about $10^{-4}$M at pH7.4, or greater than about $2*10^{-4}$, $5*10^{-4}$ or $10^{-3}$. It will be understood that the substituents at C1, C3 and C5 may be selected so as to achieve the desired lipophilicity and/or aqueous solubility.

The compound of the present invention may have an $IC_{50MDA\text{-}MB\text{-}231}$ of less than about 6 micromolar, or less than about 5.5, 5, 4.5, 4 or 3.5 micromolar. It may have an $IC_{50\ PC3}$ of less than about 6 micromolar, or less than about 5.5, 5, 4.5, 4 or 3.5 micromolar. It may have any two or more of the abovementioned properties together, e.g. it may have an aqueous solubility of greater than about $10^{-4}$M at pH7.4 and lipophilicity (log D at pH 7.4) of less than about 5, or may have an aqueous solubility of greater than about $10^{-4}$M at pH7.4 and $IC_{50MDA\text{-}MB\text{-}231}$ of less than about 6 micromolar, or it may have $IC_{50MDA\text{-}MB\text{-}231}$ and $IC_{50\ PC3}$ both of less than about 6 micromolar, or it may have aqueous solubility of greater than about $10^{-4}$M at pH7.4 and have $IC_{50MDA\text{-}MB\text{-}231}$ and $IC_{50\ PC3}$ both of less than about 6 micromolar (or, independently, some other value as specified above). It may additionally or alternatively have an $IC_{50\ Icmt}$ of less than about 2 μM, or less than about 1.8, 1.6, 1.4, 1.2 or 1 μM.

The invention also encompasses therapeutic compositions comprising the compounds described above. These compositions may be used for one or more, optionally all, of inhibiting Icmt activity, inhibiting oncogenesis and treating cancer.

The compositions may be administered either therapeutically or preventively. In a therapeutic application, compositions are administered to a patient already suffering from a disease, in an amount sufficient to cure or at least partially arrest the disease and its complications. The composition should provide a quantity of the compound or agent sufficient to effectively treat the patient.

The therapeutically effective dose level for any particular patient will depend upon a variety of factors including: the disorder being treated and the severity of the disorder; activity of the compound or agent employed; the composition employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m². Generally, an effective dosage is expected to be in the range of about 25 to about 500 mg/m², preferably about 25 to about 350 mg/m², more preferably about 25 to about 300 mg/m², still more preferably about 25 to about 250 mg/m², even more preferably about 50 to about 250 mg/m², and still even more preferably about 75 to about 150 mg/m².

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular) or oral route. More preferably administration is by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection or in the form of a formulation suitable for oral ingestion (such as capsules, tablets, caplets, elixirs, for example), or in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The inventors have hypothesized that less lipophilic cysmethynil analogs might have a better solubility-lipophilicity balance that could translate to an improved pharmacokinetic profile and bioavailability. On the other hand, an excessive reduction in lipophilicity may result in compounds that are not able to gain access to the membrane bound Icmt and thus fail to bring about adequate inhibition. In an effort to reconcile these conflicting requirements, the inventors synthesized cysmethynil analogs with a $10^4$ fold variation in lipophilicities and evaluated them for Icmt inhibitory activities as well as antiproliferative activity on breast cancer MDA-MB-231 cells. The results showed that cysmethynil can be structurally modified to give analogs that are more potent than cysmethynil and yet possess lower lipophilicities that could lead to improved bioavailability (Go M L et al, 2010 J Med Chem 53, 6838). The most promising compound to emerge from these investigation was N-ethyl-N-[(1-octyl-5-m-tolyl-1H-indol-3-yl)methyl]ethanamine.

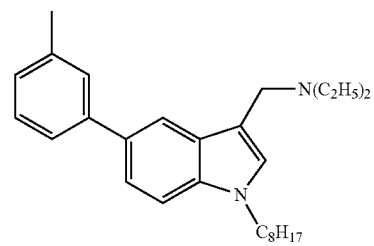

$IC_{50}$ Icmt 0.7 uM
$IC_{50}$ MDA-MB-231 3.6 uM
N-ethyl-N-[(1-octyl-5-m-tolyl-1H-indol-3-yl)methyl]ethanamine The strength of the novel compounds of the present invention are thought to lie in their superior physicochemical profiles as seen from the improved solubilities. Compounds 8-12 and 305 (see Tables 1 and 2 below) have low to submicromolar Icmt inhibitory activities and cell based antiproliferative activities. [It should be noted that compound 8-12 is also referred to herein as compound 4-12, and references to these should be taken to be equivalent. The structure of this compound is shown in Table 1.] Compared to cysmethynil they have (i) more potent growth inhibitory activities on malignant cell lines, and (ii) greater aqueous solubilities at pH 7.4. The latter may have a positive influence on the pharmacokinetic profile of the test compounds.

A key insight to emerge from investigations into the structure-activity relationship of cysmethynil is the unique contributions made by the three functionalities on the indole core of cysmethynil to Icmt inhibition. The substituent at position 5 is seen to have the least influence on Icmt inhibitory activity as only incremental changes were observed when modifications were made at that position. This may in fact work to advantage as functionalities that can moderate physicochemical properties while having minimal adverse effects on activity may be introduced at this position. In the case of position 1, lipophilic side chains are generally preferred. For instance, replacing the n-octyl of cysmethynil with the more lipophilic geranyl side chain improved Icmt inhibitory activity, but introducing the shorter and less lipophilic isoprenyl side chain in place of n-octyl had the opposite effect. Substituting the acetamide side chain of cysmethynil with a tertiary amine gave indoleamines which maintained Icmt inhibitory activity while markedly improving cell-based growth inhibitory activity. For the indoleamines, a noticeable structure activity relationship (SAR) trend was the apparent optimal pairing of groups at positions 1 and 5. For instance, a lipophilic side chain at position 1 such as n-octyl may be combined with a small, less lipophilic group like fluoro at position 5. On the other hand, a less lipophilic group like isoprenyl at position 1 must necessarily be balanced by a more lipophilic functionality like m-tolyl at position 5. With this insight, the inventors proposed that it is possible to modulate Icmt and growth inhibitory activities of indoleamines with minimal increase or even a decrease in lipophilicity.

The following provides a summary of the SAR of cysmethynil:

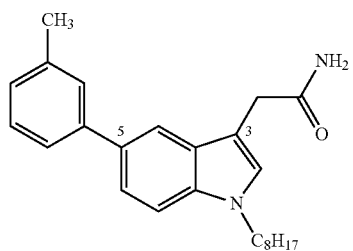

Position 5: highly tolerant of substitution-m-tolyl may be replaced by 5-F in indoleamines provided n-octyl is present at position 1

The side chain at position 3 appears to be important. Replacement with (i) tertiary amides, esters, homologues provides minimal effects on activity; (ii) tertiary amines to give indoleamines maintains Icmt inhibitory activity with marked improvements in cell based activity.

The lipophilic side chain at position 1 appears to be important for activity. n-Octyl may be replaced by geranyl and to a lesser degree by isoprenyl. Aromatic residues at this position are in general not favourable.

Based on the above SAR findings, further modifications to the cysmethynil template were investigated, which form the basis of the present invention. The first approach was to introduce polar functionalities at position 5 based on the hypothesis that this position can tolerate modifications without adverse effects on activity. The focus on polar substituents is prompted by the need to strike an optimal lipophilicity-solubility balance that is required for drug-like character. The following compounds were synthesized to achieve this end (Table 1).

TABLE 1

Structures, estimated lipophilicities (logD 7.4, log P) and solubilities (pH 7.4) of indoleamine analogs with phenyl and heteroaromatic substituents at Position 5.

| Cpd No | R | Log D $7.4^1$ (Log P)$^2$ | Solubility (pH 7.4, M)$^3$ |
|---|---|---|---|
| 8-1 | CH$_3$ (m-tolyl) | 6.37 (8.86) | 8.7 × 10$^{-5}$ |
| 8-2 | 2-F-phenyl | 5.93 (8.37) | 5.3 × 10$^{-5}$ |
| 8-3 | 3-F-phenyl | 5.83 (8.27) | 5.8 × 10$^{-5}$ |
| 8-4 | 2-CF$_3$-phenyl | 6.58 (9.03) | 3 × 10$^{-5}$ |
| 8-5 | 3-CF$_3$-phenyl | 6.44 (8.89) | 3.3 × 10$^{-5}$ |

TABLE 1-continued

Structures, estimated lipophilicities (logD 7.4, log P) and solubilities (pH 7.4) of indoleamine analogs with phenyl and heteroaromatic substituents at Position 5.

| Cpd No | R | Log $D_{7.4}$[1] (Log P)[2] | Solubility (pH 7.4, M)[3] |
|---|---|---|---|
| 8-6 | 2-OCF₃-phenyl | 6.61 (9.06) | $3.3 \times 10^{-5}$ |
| 8-7 | 4-methylpyridin-3-yl | 4.58 (7.03) | $1.5 \times 10^{-3}$ |
| 8-8 | 3-fluoro-4-methylpyridin-5-yl | 4.63 (7.03) | $4.6 \times 10^{-4}$ |
| 8-9 | 3-NO₂-4-methylphenyl | 5.72 (8.14) | $4.1 \times 10^{-5}$ |
| 8-10 | 4-(methylsulfonyl)phenyl | 4.63 (7.05) | $1.2 \times 10^{-4}$ |
| 8-12 | 2-amino-5-methylpyrimidin-yl | 3.54 (5.97) | $7.4 \times 10^{-4}$ |
| 8-15 | 5-methylpyrimidin-yl | 3.84 (6.24) | $1.8 \times 10^{-3}$ |
| 8-17 | 2-(dimethylamino)-5-methylpyrimidin-yl | 4.16 (6.59) | $2.2 \times 10^{-4}$ |
| 8-19 | 2-cyano-5-methylpyrimidin-yl | 3.51 (5.88) | $1.1 \times 10^{-4}$ |
| 8-20 | 4-methyl-3-cyanophenyl | 5.32 (7.74) | $5.3 \times 10^{-5}$ |
| 8-21 | 3-hydroxy-4-methylphenyl | 5.23 (7.7) | $2.3 \times 10^{-4}$ |
| 8-24 | 4-methyl-(N-methylsulfamoyl)phenyl | 4.81 (7.24) | $2.2 \times 10^{-4}$ |

[1]Estimated Log D at pH 7.4, ACD/Labs Release 12.0.
[2]Estimated Log D of non-ionized species (equivalent to Clog P), ACD/Labs Release 12.0.
[3]Estimated solubility (mole/L) at pH 7.4, ACD/Labs Release 12.0.

Cysmethynil is estimated to have a log $D_{7.4}$ of 6.94. As it has no ionisable moiety, its Log P is also 6.94. Estimated solubility is $3.3 \times 10^{-7}$ M. As seen from Table 1, all the analogs have estimated solubilities that are at least 100 times greater than cysmethynil. They also have lower log $D_{7.4}$ values. In particular analogs with pyrimidine (8-12, 8-15, 8-17, 8-19) and pyridine rings (8-7, 8-8) at position 5 have attractive solubility and lipophilicity profiles. The same may be true for the methyl sulfonyl and methylaminosulfonyl substituents of 8-10 and 8-24 respectively.

Another modification reported herein involves restricting the conformational flexibility of the diethylaminomethyl side chain of the indoleamines. The inventors speculated that conformation restriction of this side chain, which is known to play a critical role in Icmt and cell growth inhibition, will bring about a smaller loss in entropy when the restrained molecule binds to its putative receptor. Consequently, the conformationally restricted analog may enjoy a free energy advantage arising from the minimal loss of conformational entropy upon binding, not seen with flexible analogs. Table 2 shows the structures of a series of tetrahydrocarbolines in which the aminomethyl side chain has been restrained in a six-membered ring.

TABLE 2
Structures, estimated lipophilicities (logD 7.4, log P) and solubilities (pH 7.4) of conformationally restrained analogs of indoleamines: Tetrahydrocarbolines
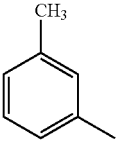
| Cpd No | R1 | R2 | R3 | Log D $_{7.4}$[1] (Log P)[2] | Solubility (pH 7.4, M)[3] |
|---|---|---|---|---|---|
| 235 | —CH$_3$ | n-C$_8$H$_{17}$ | 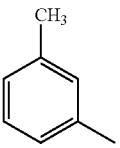 | 5.93 (7.55) | 4.9 × 10$^{-5}$ |
| 260 | —CH(CH$_3$)$_2$ | n-C$_8$H$_{17}$ | 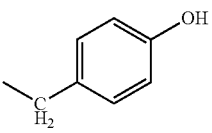 | 6.64 (5.37) | 1.8 × 10$^{-5}$ |
| 240 | 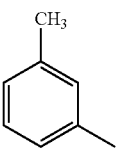 | n-C$_8$H$_{17}$ | 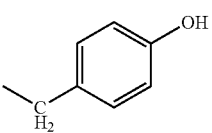 | 7.43 (8.47) | 1.3 × 10$^{-6}$ |
| 300 | 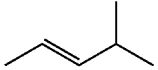 | 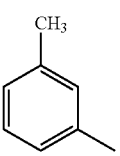 | 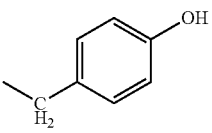 | 5.31 (6.28) | 8.8 × 10$^{-6}$ |
| 199 | —CH$_3$ | n-C$_8$H$_{17}$ | —F | 3.7 (5) | 6.6 × 10$^{-4}$ |
| 205 | 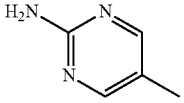 | n-C$_8$H$_{17}$ | —F | 5.17 (5.91) | 1.5 × 10$^{-5}$ |
| 309 | H | n-C$_8$H$_{17}$ | 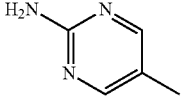 | 2.35 (4.98) | 3.3 × 10$^{-3}$ |
| 305 | —CH$_3$ | n-C$_8$H$_{17}$ | 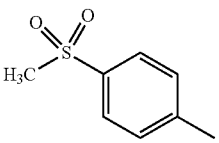 | 3.17 (4.66) | 3.7 × 10$^{-4}$ |
| 314 | H | n-C$_8$H$_{17}$ |  | 3.4 (6.06) | 4.8 × 10$^{-4}$ |

TABLE 2-continued

Structures, estimated lipophilicities (logD 7.4, log P) and solubilities (pH 7.4) of conformationally restrained analogs of indoleamines: Tetrahydrocarbolines

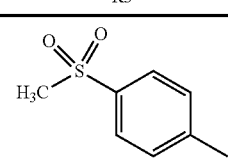

| Cpd No | R1 | R2 | R3 | Log D $_{7.4}$[1] (Log P)[2] | Solubility (pH 7.4, M)[3] |
|---|---|---|---|---|---|
| 306 | —CH$_3$ | n-C$_8$H$_{17}$ | 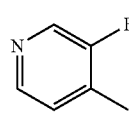 | 4.24 (5.74) | 5.6 × 10$^{-5}$ |
| 315 | H | n-C$_8$H$_{17}$ | (3-F-pyridyl-methyl) | 3.45 (6.03) | 1.9 × 10$^{-3}$ |

[1]Estimated Log D at pH 7.4, ACD/Labs Release 12.0 in which the queried compound is dissected into fragments with known Log D values such that the estimated Log D of the compound is then a summation of the Log D values of these fragments.
[2]Estimated Log D of non-ionized species (equivalent to Clog P), ACD/Labs Release 12.0.
[3]Estimated solubility (mole/L) at pH 7.4, ACD/Labs Release 12.0.

Conformational restriction of the aminomethyl side chain appears to be accompanied by a modest improvement in solubility and a small decrease in lipophilicity, as seen from the estimated Log D and solubility values for 8-1 (log D$_{7.4}$ 6.37, solubility 8.7×10$^{-5}$ M) and 235 (log D$_{7.4}$ 5.93, solubility 4.9×10$^{-5}$ M). Variations at R1 are R1=H (to note that this modification results in a secondary amine), methyl, isopropyl and p-hydroxybenzyl. As anticipated, the considerably larger and bulkier p-hydroxybenzyl moiety gave analogs with markedly lower solubilities than 8-1, even in the case of 300 which has a shorter and less lipophilic isoprenyl side chain. The introduction of heteroaromatic rings (pyrimidine, pyridine) at R3 as well as the replacement of m-tolyl with p-methylsulfonylphenyl at the same position may have the desired effects of improving solubility and lowering lipophilicity.

The compounds in Tables 1 and 2 were evaluated for inhibition of Icmt and growth inhibitory effects on two malignant cell lines MDA-MB231 and PC3. The results are given in Table 3.

TABLE 3

IC$_{50}$ values for inhibition of Icmt and antiproliferative activities of test compounds

| Cpd No | IC$_{50\ Icmt}$ (μM)[1] | IC$_{50MDA-MB-231}$ (μM)[1] | IC$_{50\ PC3}$ (μM)[1] |
|---|---|---|---|
| 8.1 | 2.18 | 7.90 (1.72) | 6.31 (0.20) |
| 8.2 | 2.56 | 7.03 (0.81) | 7.28 (2.57) |
| 8.3 | 1.61 | 6.71 (0.21) | 6.25 (0.67) |
| 8.4 | 1.28 | 6.69 (0.13) | 9.66 (2.62) |
| 8.5 | 2.61 | 6.53 (0.49) | 6.81 (0.53) |
| 8.6 | ND[2] | 7.17 (0.06) | 11.19 (2.48) |
| 8.7 | 1.75 | 5.50 (0.81) | 5.84 (0.31) |
| 8.8 | 0.96 | 5.14 (0.67) | 5.88 (0.44) |
| 8.9 | ND[2] | 6.51 (0.98) | 7.29 (0.85) |
| 8.10 | 1.72 | 5.56 (0.58) | 4.74 (1.31) |
| 8.12 | 0.78 | 2.63 (0.43) | 2.55 (0.46) |
| 8.15 | 1.58 | 9.00 | 8.32 |
| 8.17 | 1.63 | 2.24 | 2.01 |
| 8.19 | 2.26 | 3.95 | 5.92 |
| 8.20 | 2.45 | 7.72 | 6.19 |
| 8.21 | 5.43 | 14.75 | 17.43 |
| 8.24 | 1.71 | 8.52 | 6.58 |
| 235 | 10.3 | 9.18 (1.45) | 7.58 (1.57) |
| 260 | 8.3 | 7.38 (0.48) | 9.69 (1.84) |
| 240 | ND[2] | 14.75 (5.45) | 10.25 (1.38) |
| 300 | ND[2] | 9.38 (0.92) | 13.3 (5.70) |
| 199 | ND[2] | 19.21 (1.64) | 15.52 (0.25) |
| 205 | ND[2] | 10.5 (0.08) | 10.53 (0.28) |
| 309 | ND[2] | 2.72 (0.24) | 4.44 (0.06) |
| 305 | 3.3 | 4.61 (0.07) | 4.31 (0.34) |
| 314 | ND[2] | 2.10 (0.02) | 2.92 (0.21) |
| 306 | ND[2] | 4.60 (0.06) | 5.38 (0.29) |
| 315 | ND[2] | 4.59 (0.33) | 7.69 (0.07) |
| Cysmethynil | 1.8 (0.32) | 26.8 (1.9) | 24.8 (1.5) |

[1]Mean of two or more separate determinations. Standard deviations (in parentheses) are given only for those compounds that were evaluated on more than 2 separate occasions.
[2]ND = not determined.

The following deductions may be drawn from the results in Table 3. Except for 8.6 and 8.9 whose IC$_{50}$ Icmt were not determined, the other indoleamines with different substituents at position 5 have Icmt inhibitory properties that fall within a relatively narrow range (0.8-5.4 μM) and do not vary markedly from that of cysmethynil. There is however a significant improvement in cell-based antiproliferative activity compared to cysmethynil.

Mention should be made of 8-1 which is the most promising analog identified in an earlier study. A re-determination of IC$_{50}$ values indicated that this compound is not more potent than cysmethynil as an Icmt inhibitor (IC$_{50}$ 2.2 uM, compared to the previous value of 0.7 uM) but it still maintains a better antiproliferative profile than cysmethynil, notwithstanding the higher IC$_{50\ MDA-MB-231}$ that is obtained on redetermination (7.9 uM compared to the previous value of 3.6 uM$^{28}$).

The most promising analog to emerge from this series is 8-12 which has an IC$_{50\ Icmt}$ of 0.78 μM and antiproliferative IC$_{50}$ of 2.63 μM (MDA-MB-231) and 2.55 uM (PC3). SAR for 8-12 suggests that the presence of the amino substituent is important (compare 8-12 and 8-15). Replacing the amino substituent with the polar nitrile functionality (8-20) was not favoured. Replacing the aminopyrimidine ring of 8-12 with 2-fluoro-4-pyridyl (8-8) maintained a near submicromolar IC$_{50}$ for Icmt inhibition but antiproliferative activity on MDA-MB-231 and PC3 cells were less impressive. 8-7 which has an unsubstituted 3-pyridyl ring at position 5 also failed to impress.

Unlike analogs with heteroaromatic rings at position 5, those analogs with substituted phenyl rings at position 5 do not appear to have significant inhibitory advantage over 8-1. Notwithstanding the range of substituents deployed (fluoro, trifluoromethyl, triflouromethoxy, cyano, methylsulfonyl, methylaminosulfonyl, hydroxyl), IC$_{50}$ values for Icmt inhibition and antiproliferative activities generally cluster over a narrow range. Although they are more potent than cysmethynil in terms of antiproliferative activities on the two malignant cell lines, these analogs are generally equipotent to cysmethynil in terms of Icmt inhibition.

Icmt inhibitory activities of most tetrahydrocarbolines have not been determined. Of the 3 analogs that have been assessed for their Icmt inhibitory activities, the results suggest that restraining the aminomethyl side chain diminishes Icmt inhibitory activity. Compound 235 with the restrained side chain is almost 5 times less potent as an Icmt inhibitor than its conformationally flexible analog 8-1. The most potent compound (305) has an IC$_{50\ Icmt}$ of 3.3 μM, which is about 2 fold higher than that of cysmethynil. However, most of the tetrahydrocarbolines demonstrate good cell-based antiproliferative activity.

Preliminary SAR for cell based antiproliferative activity of tetrahydrocarbolines suggests that the size of the N-substituent (R$_1$, position 2) on the tetrahydrocarboline scaffold should be kept small. Thus, analogs with the bulky p-hydroxybenzyl substituent (240, 300, 205) were associated with poor activity. On the other hand, a ring structure is preferred at position 8 (R$_3$) as seen from the poor activities associated with 199 and 205 which have R$_3$=F in place of an aromatic ring. Intriguingly, 2-aminopyrimidine is seen again to be a favoured substituent, as in the case of the indoleamines. Compound 305 has a good inhibitory profile for both Icmt and cell based antiproliferative activities. Compounds 309 and 314 may be potential hits, pending determination of their Icmt inhibitory activities. The cell based inhibitory profiles of 314 are almost comparable to that of 8-12. 314 has a p-methylsulfonylphenyl substituent at R$_3$ and it is structurally related to 8-10 in the indoleamine series.

Taken together, the present study has identified the following compounds as particularly promising inhibitors:

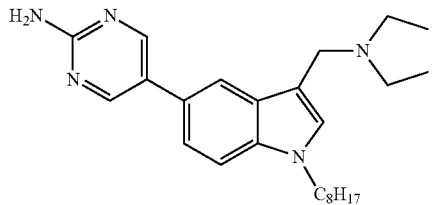

IC$_{50\ Icmt}$ 0.8 uM
IC$_{50\ MDAMB231}$ 2.6 uM
IC$_{50\ PC3}$ 2.6 uM
MW 404.32

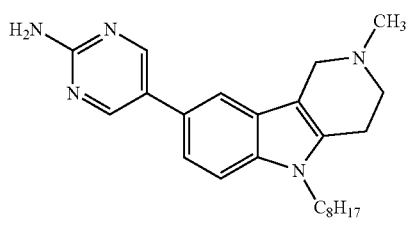

IC$_{50\ Icmt}$ 3 uM
IC$_{50\ MDAMB231}$ 4.6 uM
IC$_{50\ PC3}$ 4.3 uM
MW 391.27

Estimated solubilities of 8-12 and 305 (Tables 1, 2) point to significantly good solubilities for both compounds. The aqueous solubilities at pH 7.4 of 8-12, 305, cysmethynil, 8-1 and other representative compounds were determined on Multiscreen® solubility filter plates. Briefly, the test compound in DMSO was diluted with phosphate buffer pH 7.4 (1% DMSO) to give a final concentration of approximately 400 μM. The turbid solution was delivered to the filter plate, agitated for a specific time period and then filtered. The concentration of dissolved compound in the filtrate was determined by uv spectroscopy and referred to pre-constructed calibration curves for solubility determination. The procedure provides an assessment of the kinetic solubilities of the compound at 3 h and 24 h. Results are given in Table 4.

TABLE 4

Aqueous solubilities of selected analogs at pH 7.4, after 3 h and 24 h of agitation

| Compound | Aqueous Solubility (pH 7.4)$^1$ | |
| --- | --- | --- |
| | 3 hours | 24 hours |
| Cysmethynil | <1 μM | <1 μM |
| 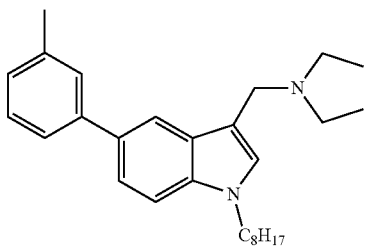 8-1 | <1 μM | <1 μM |

TABLE 4-continued

Aqueous solubilities of selected analogs at pH 7.4, after 3 h and 24 h of agitation

| Compound | Aqueous Solubility (pH 7.4)[1] | |
|---|---|---|
| | 3 hours | 24 hours |
| 8-7 | 249.7 (9.7) μM | 244.8 (9.7) μM |
| 8-12 | 166.2 (8.6) μM | 155.9 (6.4) μM |
| 8-15 | 266.3 (5.5) μM | 271.6 (6.6) μM |
| 8-17 | 25.3 (3.4) μM | 24.9 (1.5) μM |
| 305 | 49.5 (3.8) μM | 40.6 (1.8) μM |

[1]Mean and SD of 3 determinations from 2 different stock solutions

In general, with an average permeability and a projected clinical potency of 1 mg per kg, a drug is thought to require a minimum aqueous solubility of 50-100 µg per mL to avoid the use of non-standard solubility-fixing formulation applications. Notwithstanding the kinetic nature of the solubility determination that is employed here, 8-12 has an approximate solubility of 65 µg per mL while 305 has a lower solubility of 20 µg per mL. Both solubilities exceed that of cysmethynil and 8-1.

Overall, two novel analogs 8-12 and 305 have been identified which show low to submicromolar Icmt inhibitory activities and cell based antiproliferative activities. The advantages offered by these compounds compared to cysmethynil are (i) more potent growth inhibitory activities on malignant cell lines, and (ii) greater aqueous solubilities at pH 7.4.

Following the above studies, further compounds related to or within the scope of the present invention were investigated. The results are shown in Table 5.

TABLE 5

Structures and IC$_{50}$ values for antiproliferative activities of various compounds

| Compound | Structure | IC50 (µM)$^a$ MDA-MB231 | IC50 (µM)$^a$ PC 3 | Molecular weight |
|---|---|---|---|---|
| cpd 205 | 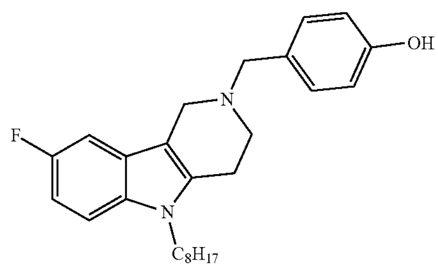 | 10.5 ± 0.08 | 10.53 ± 0.28 | 408.55 |
| cpd 214 | 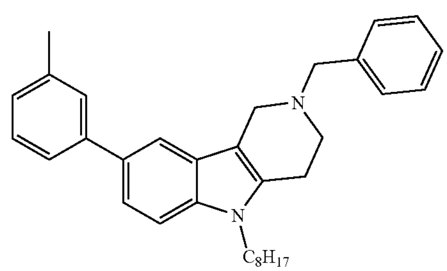 | 8.60 ± 1.68 | 10.91 ± 2.31 | 464.68 |
| cpd 260 | 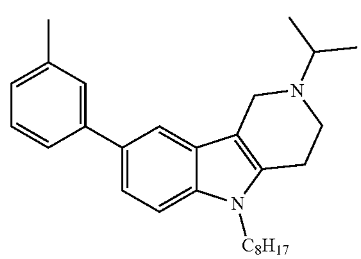 | 7.38 ± 0.48 | 9.69 ± 1.84 | 416.64 |
| cpd 273 | 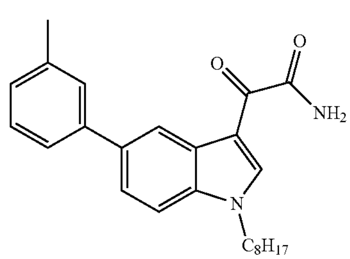 | >50 | 16.70 ± 1.68 | 390.52 |

TABLE 5-continued
Structures and IC₅₀ values for antiproliferative activities of various compounds
| Compound | Structure | IC50 (μM)$^a$ MDA-MB231 | IC50 (μM)$^a$ PC 3 | Molecular weight |
|---|---|---|---|---|
| cpd 300 | 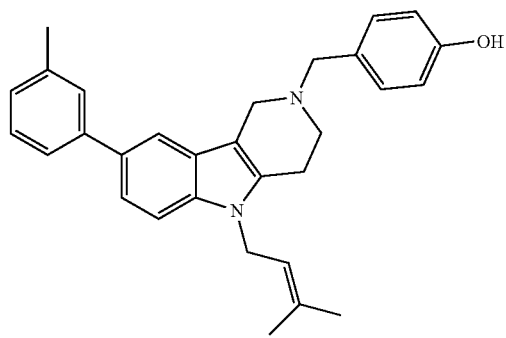 [SMILES: CC(C)=CCn1c2c(c3cc(-c4cccc(C)c4)ccc31)CN(Cc1ccc(O)cc1)CC2] | 9.38 ± 0.92 | 13.30 ± 5.70 | 436.59 |
| cpd 319 | 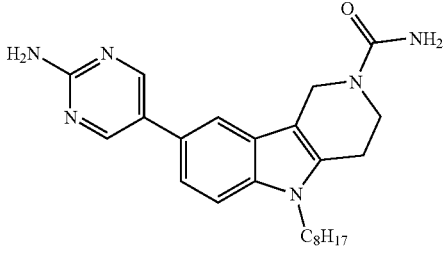 | ND | 9.43 ± 3.85 | 420.55 |
| cpd 321 | 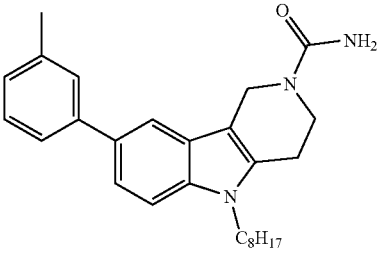 | ND | 10.54 ± 3.08 | 417.59 |
| cpd 323 | 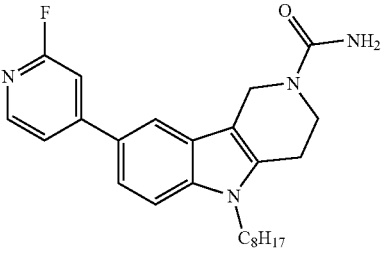 | ND | 10.2 ± 3.63 | 422.54 |
| cpd 324 | 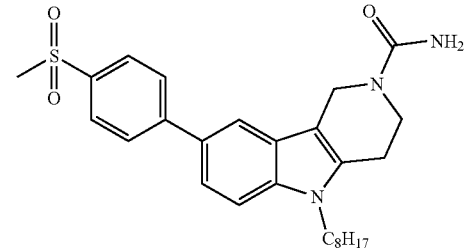 | ND | 8.88 ± 0.62 | 481.65 |

TABLE 5-continued

Structures and IC$_{50}$ values for antiproliferative activities of various compounds

| Compound | Structure | IC50 (μM)$^a$ MDA-MB231 | IC50 (μM)$^a$ PC 3 | Molecular weight |
|---|---|---|---|---|
| cpd 474 | 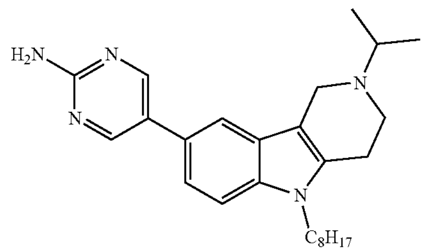 | 9.17 ± 0.54 | 9.32 ± 0.65 | 419.60 |
| cpd 480 | 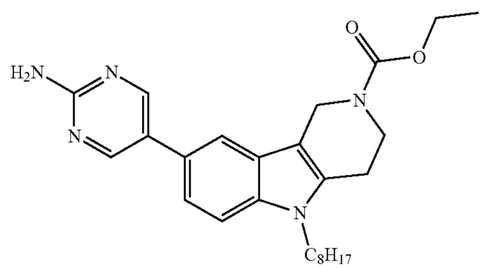 | 17.0 | 21.3 | 449.59 |
| cpd 481 | 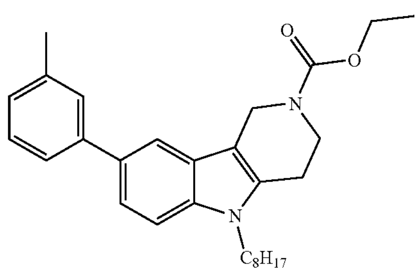 | 25.9 | 30.1 | 446.62 |
| cpd 488 | 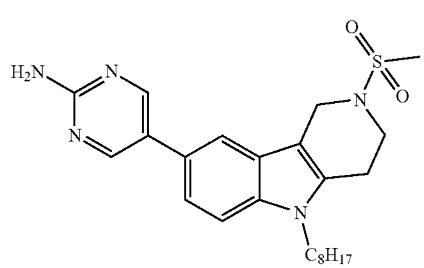 | 27.4 | ND | 455.62 |
| cpd 490 | 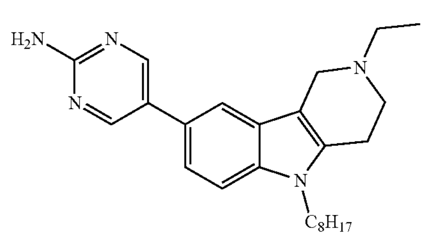 | 5.85 | ND | 405.58 |

TABLE 5-continued

Structures and IC$_{50}$ values for antiproliferative activities of various compounds

| Compound | Structure | IC50 (μM)$^a$ MDA-MB231 | IC50 (μM)$^a$ PC 3 | Molecular weight |
|---|---|---|---|---|
| cpd 510 | (2-aminopyrimidin-5-yl)-substituted tetrahydro-β-carboline with N-C$_8$H$_{17}$ and N-CH$_2$CH$_2$OH | 3.42 ± 0.72 | 3.97 ± 0.42 | 421.58 |
| cpd 512 | 5-(2-aminopyrimidin-5-yl)-1-octyl-1H-indole-3-acetamide | >50 | >50 | 379.50 |
| cpd 513 | 5-(2-fluoropyridin-4-yl)-1-octyl-1H-indole-3-acetamide | 26.09 ± 0.41 | 25.64 ± 3.48 | 381.48 |
| cpd 582 | 5-(2-aminopyrimidin-5-yl)-1-butyl-3-((adamantylamino)methyl)-1H-indole | ND | ND | 429.60 |

ND = not done

EXAMPLES

General Details for Chemical Synthesis

Reagents (synthetic grade or better) were obtained from commercial suppliers and used without further purification. Microwave reactions were carried out on the Biotage Initiator® Microwave Synthesizer. Merck silica 60 F254 sheets and Merck silica gel (0.040-0.063 mm) were used for thin layer chromatography (TLC) and flash chromatography respectively. $^1$H NMR spectra (400 MHz) were determined on a Bruker DRX 400 spectrometer with reference to residual d-chloroform (δ 7.260) or d$_6$-DMSO (δ 2.500) as internal standards. $^{13}$C NMR spectra (100 MHz) were determined on the same instruments and reported in ppm (δ) relative to residual d-Chloroform (δ 76.9). Coupling constants (J) were reported in Hertz (Hz). Proton ($^1$H) NMR spectral information is tabulated in the following format: multiplicity, coupling constant, number of protons. Multiplicities are reported as follows: s=singlet, d=doublet, t=triplet, q=quartet, dd=doublet of doublets, td=doublet of triplet, m=multiplet The m/z values of these compounds were determined by LC-MS (Waters Mircromass zq) using an ESI probe (indoleamines). For tetrahydrocarbolines, mass spectra were recorded in positive ion mode using electro spray ionization (ESI) or high-resolution LC-MS (IT TOF).

Syntheses of Indoleamines

Figure 3:
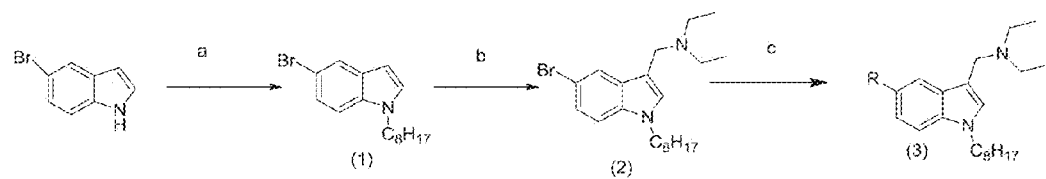
FIG. 3: Syntheses of indoleamines

The indoleamines comprise 5-substituted indole compounds with tertiary diethyl amine substitutions at position 3 and n-octyl substitution at position 1. Common synthetic protocol is shown in FIG. 3. Reagents and conditions: (a) sodium hydride (NaH, 60%), 1-bromooctane, DMF, 0° C. to rt; (b HCHO, diethylamine, RT stirring overnight (c) boronic acid, Pd(PPh$_3$)$_4$, potassium carbonate (K$_2$CO$_3$, aqueous solution), 1,4-dioxane, microwave, 20 min, 100 deg C.

5-Bromo-1-octyl-1H-indole (1)

To a stirred suspension of sodium hydride (NaH, 60% dispersion in mineral oil; 48 mg, 2 mmol) in anhydrous dimethylformamide (5 ml) in an ice bath was added dropwise a solution of 5-bromo 1H indole (1.5 mmol) in anhydrous DMF (10 mL) over a period of 10 min at 0 C. After stirring for 10 min, 1-Bromooctane (1.8 mmol) was added drop wise over 5 min and reaction mixture was allowed to warm to RT and left with stirring for overnight. The reaction was quenched by pouring over ice and extracted twice with ethyl acetate (25 ml). The combined organic layers were washed with brine, dried ($Na_2SO_4$), filtered and concentrated under reduced pressure to obtain the crude residue. The crude material was purified by flash silica gel column chromatography with ethyl acetate and Hexane to get 5-bromo 1-octyl 1H-indole as an oil (Yield: 80 to 90%). Product was confirmed by NMR and LC-MS $^1$H NMR (400 MHz, $CDCl_3$): δ 0.85 (t, J=7 Hz, 3H), 1.25-1.29 (m, 12H), 1.79 to 1.83 (m 2H), 4.08 (t, J=7 Hz, 2H), 6.42 (dd, J=3 Hz 1H), 7.09 (d, J=3 Hz, 1H), 7.19-7.29 (m, 2H), 7.75 (d, J=2 Hz, 1H); LC-MS (ESI): m/z 308.11. [M+H]$^+$ (5-bromo-1-octyl-1H-indol-3-ylmethyl)ethylamine (2)

To a stirred solution of 5-bromo 1-octyl 1H-indole (2 mmol) in acetic acid (10 ml) was added formaldehyde (0.5 ml) and diethyl amine (4 mmol), reaction was stirred at RT overnight, reaction were monitored by TLC. Reaction was quenched by methylene chloride 20 ml, and 15 ml of water and pH was adjusted to 9 using 1N NaOH solution. Added more methylene chloride and organic layer was washed with water. Combined organic layer was washed with brine, dried ($Na_2SO_4$) and concentrated under reduced pressure to obtain the crude residue. The crude material was purified by column chromatography in chloroform and Methanol solvent system to get oily product. Product was confirmed by LC-MS and NMR. Yield 40 to 60%.

$^1$H NMR (400 MHz, $CDCl_3$): δ 0.85 (t, J=7 Hz, 3H), 1.25-1.29 (m, 12H), 1.79 to 1.83 (m 2H), 4.08 (t, J=7 Hz, 2H), 6.42 (dd, J=3 Hz 1H), 7.09 (d, J=3 Hz, 1H), 7.19-7.29 (m, 2H), 7.75 (d, J=2 Hz, 1H); $^{13}$C NMR (125 MHz, $CDCl_3$): δ 14.06, 22.62, 24.11, 24.42, 26.58, 26.72, 29.17, 31.59, 31.81, 49.08, 56.92, 58.11, 64.36, 107.27, 107.45, 110.00, 114.46, 114.49, 119.55, 119.61, 119.11, 123.98, 124.07, 129.73, 131.79, 131.85., 148.95, 151.37 LC-MS (ESI): m/z 393.11. [M+H]$^+$

General Method for the Synthesis of diethyl-[5-substituted-1-octyl-1H-indol-3yl methyl]-amines (3)

In a microwave reaction tube (20 ml), to a suspension of diethyl-(5-bromo-1-Octyl-1H-indol-3-yl methyl)-amine (0.8 mmol), corresponding boronic acid, (1.25 mmol) and 5,10,15,20-tetrakis(pentafluorophenyl)-21H,23H-phosphine palladium(II) (55 mg 0.05 mmol), in 3 ml of dry 1,4-dioxane was added 2 ml of potassium carbonate (1.5 mM) solution in water and the tube was sealed. The microwave reaction was carried out for 20 min at a temperature of 100° C. with stirring. After 20 min the reaction was stopped, the mixture had turned from an orange to a black color solution. The reaction mixture was extracted twice with ethyl acetate (25 ml), the combined organic layers were washed once with water (20 ml), brine, dried ($Na_2SO_4$) and concentrated under reduced pressure to obtain the crude residue. The crude material was purified by flash column chromatography to give diethyl-[5-R-1-octyl-1H-indol-3yl methyl]-amine. Product was confirmed by NMR and LC-MS, purity was confirmed by HPLC. Average yield was 25-40%

8.1: Diethyl-1-(1-octyl-5m-tolyl-1H-indol-3yl (methyl)-amine $^1$H NMR (400 MHz, $CDCl_3$ δ 0.85 (t, 3H), 1.25-1.49 (m, 18H), 1.79 to 1.83 (m 2H), 2.45 (s, 3H) 3.00-3.35 (m, 4H), 4.12 (t, 2H), 4.45 (d, 2H), 7.10 to 7.35 (m 4H), 7.40 to 7.55 (m 4H), 7.75 (s, 1H); $^{13}$C NMR (125 MHz, $CDCl_3$): δ 8.95, 14.07, 21.60, 22.61, 26.94, 29.12, 29.82, 30.06, 31.76, 45.43, 46.85, 46.92, 101.74, 110.55, 116.11, 122.29, 124.63, 127.64, 128.21, 128.34, 128.67, 128.75, 131.85, 134.38, 135.60, 138.43, 142.00, 184.49, LC-MS (ESI): m/z 405.40. [M+H]$^+$ 8.2: Diethyl-[5 (2-Fluoro-phenyl)-1-octyl-1H-indol-3yl methyl-amine $^1$H NMR (400 MHz, $CDCl_3$): δ 0.85 (t, 3H), 1.25-1.49 (m, 18H), 1.79 to 1.83 (m 2H), 3.00-3.35 (m, 4H), 4.12 (t, 2H), 4.45 (d, 2H), 7.10 to 7.35 (m 4H), 7.40 to 7.55 (m 4H), 7.75 (s, 1H), LC-MS (ESI): m/z 409.37. [M+H]$^+$ 8.3: Diethyl-[5(3-Fluoro-phenyl)-1-octyl-1H-indol-3yl methyl-amine $^1$H NMR (400 MHz, $CDCl_3$): δ 0.85 (t, 3H), 1.25-1.49 (m, 18H), 1.79 to 1.83 (m 2H), 3.00-3.35 (m, 4H), 4.12 (t, 2H), 4.48 (d, 2H), 7.15 (t, 2H), 7.40 to 7.60 (m 5H), 7.70 (s, 1H), $^{13}$C NMR (125 MHz, $CDCl_3$): δ 8.87, 14.05, 22.59, 26.92, 29.11, 30.05, 31.74, 45.38, 46.83, 46.91, 101.86, 110.63, 115.51, 115.72, 116.18, 122.08, 128.63, 128.82, 128.89, 131.93, 133.25, 135.59, 138.12, 160.98, 163.42, LC-MS (ESI): m/z 409.37. [M+H]$^+$ 8.4: Diethyl-1-(1-octyl-5-(2-trifluoromethyl-phenyl)-1H-indol-3 ylmethyl-amine $^1$H NMR (400 MHz, $CDCl_3$): δ 0.85 (t, 3H), 1.25-1.49 (m, 18. H), 1.85 to 1.95 (m 2H), 2.85-3.10 (m, 4H), 4.10-4.35 (m, 4H), 7.15 (dd, 1H), 7.40 to 7.60 (m 4H), 7.70 (s, 1H), 7.80 (dd, 1H), LC-MS (ESI): m/z 459.33. [M+H]$^+$ 8.5: Diethyl-1-(1-octyl-5-(3-trifluoromethyl-phenyl)-1H-indol-3ylmethyl-amine $^1$H NMR (400 MHz, $CDCl_3$): δ 0.85 (t, 3H), 1.25-1.49 (m, 18H), 1.79 to 1.83 (m 2H), 3.00-3.35 (m, 4H), 4.12 (t, 2H), 4.55 (s, 2H), 7.40-7.60 (m 5H), 7.70-7.90 (m, 3H), $^{13}$C NMR (125 MHz, $CDCl_3$): δ 8.83, 14.04, 22.59, 26.90, 29.10, 30.04, 31.74, 45.40, 46.88, 46.95, 102.10, 110.86, 116.45, 122.04, 122.95, 123, 37, 123.40, 124.02, 125.65, 128.69, 129.31, 130.72, 130.95, 131.27, 132.72, 135.94, 142.81, 163.42, LC-MS (ESI): m/z 459.33. [M+H]$^+$ 8.6: Diethyl-1-(1-octyl-5-(3-trifluoromethoxy-phenyl)-1H-indol-3ylmethyl-amine $^1$H NMR (400 MHz, $CDCl_3$): δ 0.85 (t, 3H), 1.25-1.49 (m, 18H), 1.79 to 1.83 (m 2H), 2.85-3.10 (m, 4H), 4.12 (t, 2H), 4.33 (s, 2H), 6.70-6.80 (m 1H), 7.10-7.30 (m 2H), 7.40-7.70 (m, 5H), $^{13}$C NMR (125 MHz, $CDCl_3$): δ 8.93, 14.03, 22.59, 26.86, 29.12, 30.14, 31.73, 45.43, 46.89, 47.03, 102.31, 110.85, 116.24, 118.95, 119.32, 119.42, 119.84, 122.07, 125.67, 128.44, 128.56, 128.83, 130.10, 131.29, 132.64, 135.87, 144.15, 149.08, 150.04, 158.42, LC-MS (ESI): m/z 475.50. [M+H]$^+$

8.7: Diethyl-(1-octyl-5-pyridin-3-yl-1H-indol-3ylmethyl)-amine $^1$H NMR (400 MHz, CDCl$_3$): δ 0.85 (t, 3H), 1.15-1.49 (m, 18H), 1.80 to 1.93 (m 2H), 3.00-3.35 (m, 4H), 4.12 (t, 2H), 4.55 (s, 2H), 7.40-7.65 (m 3H), 7.75-7.85 (m 1H), 8.05 (s, 1H), 8.50-8.80 (m, 2H), 9.15 (s, 1H), $^{13}$C NMR (125 MHz, CDCl$_3$): δ 8.55, 14.03, 22.57, 26.88, 29.09, 30.04, 31.71, 45.44, 47.01, 47.20, 103.10, 111.48, 117.95, 121.36, 126.67, 128.58, 132.60, 136.92, 140.06, 140.87, 141.11, 162.13, 162.49, LC-MS (ESI): m/z 392.4. [M+H]$^+$

8.8: Diethyl-[5(4-Fluoro-pyrdin-3yl)-1-octyl-1H-indol-3yl methyl]-amine $^1$H NMR (400 MHz, CDCl$_3$): δ 0.85 (t, 3H), 1.15-1.40 (m, 18H), 1.80 to 1.93 (m 2H), 2.65-2.80 (q, 4H), 3.95 (s, 2H), 4.12 (t, 2H), 7.00 (dd 1H), 7.25-7.45 (m 3H), 7.85 (s, 1H), 8.05 (t, 1H), 8.45 (s, 1H), $^{13}$C NMR (125 MHz, CDCl$_3$): δ 11.19, 14.07, 22.62, 26.99, 29.17, 30.25, 31.76, 46.35, 46.58, 47.74, 109.03, 109, 40, 110.24, 117.91, 120.92, 128.02, 129.07, 129.41, 136.09, 140.06, 139.94, 145.67, 162.13, 164.49, LC-MS (ESI): m/z 410.06. [M+H]$^+$

8.9: Diethyl-[5(3-nitro-phenyl)-1-octyl-1H-indol-3yl methyl]-amine $^1$H NMR (400 MHz, CDCl$_3$): δ 0.85 (t, 3H), 1.15-1.40 (m, 18H), 1.80 to 1.93 (m 2H), 2.65-2.80 (q, 4H), 4.05 (s, 2H), 4.12 (t, 2H), 7.35 (s 1H), 7.40-7.55 (m 2H), 7.60 (t, 1H), 7.90 (s, 1H), 7.95 (dd, 1H), 8.15 (dd, 1H), 8.50 (s, 1H) $^{13}$C NMR (125 MHz, CDCl$_3$): δ 10.88, 14.08, 22.62, 26.98, 29.18, 30.25, 31.76, 46.32, 46.66, 47.72, 110.37, 117.82, 121.05, 121.15, 121.96, 128.97, 129.57, 129.98, 133.27, 136.29, 144.21, 148.73, LC-MS (ESI): m/z 438.39. [M+H]$^+$

8.10: Diethyl-[5(4-methanesulfonyl-phenyl)-1-octyl-1H-indol-3yl methyl]-amine $^1$H NMR (400 MHz, CDCl$_3$): δ 0.85 (t, 3H), 1.15-1.40 (m, 18H), 1.70 to 1.90 (m 2H), 2.95-3.05 (m, 4H), 3.10 (s, 3H), 4.12 (t, 2H), 4.35 (s, 2H), 7.40-7.50 (dd, 2H), 7.55 (s, 1H), 7.75-7.95 (m, 5H), $^{13}$C NMR (125 MHz, CDCl$_3$): δ 9.31, 14.08, 22.59, 26.92, 29.14, 30.16, 31.73, 44.52, 44.65, 45.80, 46.93, 47.16, 103.04, 110.92, 117.44, 122.06, 125.98, 127.87, 128.09, 128.54, 131.67, 132.13, 136.32, 138.31 147.54, LC-MS (ESI): m/z 469.39. [M+H]$^+$

8.12: 5-(3-Diethylaminomethyl-1-octyl-1H-indol-5-yl)-pyrimidin-2-ylamine $^1$H NMR (400 MHz, CDCl$_3$): δ 0.85 (t, 3H), 1.15-1.40 (m, 16H), 1.70 to 1.90 (m 2H), 2.85 (q, 4H), 4.05 (s, 2H), 4.12 (t, 2H), 5.25 (br, 2H), 7.25-7.35 (m, 1H), 7.40-7.50 (m, 2H), 7.75 (s, 1H), 8.55 (s, 2H), $^{13}$C NMR (125 MHz, CDCl$_3$): δ 10.55, 14.06, 22.60, 26.97, 29.17, 30.23, 31.75, 46.06, 46.69, 47.47, 110.52, 116.36, 120.41, 126.31, 126.88, 129.05, 130.38, 135.73, 156.58, 161.76, LC-MS (ESI): m/z 408.39. [M+H]$^+$

8.15: Diethyl-(1-octyl-5-pyrimidin-5-yl-1H-indol-3ylmethyl)-amine $^1$H NMR (400 MHz, CDCl$_3$): δ 0.85 (t, 3H), 1.15-1.40 (m, 16H), 1.75 to 1.90 (m 2H), 2.7 (q, 4H), 3.9 (s, 2H), 4.12 (t, 2H), 7.25 (br, 1H), 7.90 (s, 1H), 9.00 (s, 2H), 9.15 (s, 1H), $^{13}$C NMR (125 MHz, CDCl$_3$): δ 9.69, 13.88, 22.40, 26.77, 28.96, 29.98, 31.55, 45.67, 46.56, 47.17, 66.89, 110.46, 112.55, 117.00, 118.92, 121.25, 122.88, 128.61, 129.71, 130.62, 131.73, 135.90, 143.29, 157.63, LC-MS (ESI): m/z 393.54. [M+H]$^+$

8.17: [5-(3-Diethylaminomethyl-1-octyl-1H-indol-5-yl)-pyridin-2-yl]-dimethyl-amine $^1$H NMR (400 MHz, CDCl$_3$): δ 0.85 (t, 3H), 1.15-1.40 (m, 16H), 1.75 to 1.90 (m 2H), 2.9 (q, 4H), 3.12 (s, 6H), 4.12 (t, 2H), 4.2 (s, 2H), 6.6 (d, 1H), 7.40 (s, 2H), 7.60 (s, 1H), 7.70-7.80 (m, 2H), 8.45 (s, 1H), $^{13}$C NMR (125 MHz, CDCl$_3$): δ 9.96, 14.08, 22.61, 26.98, 29.17, 30.22, 31.76, 38.30, 45.83, 46.80, 47.28, 105.84, 110.45, 115.57, 121.06, 125.64, 128.94, 131.02, 131.28, 135.21, 136.23, 146.16, 158.36, LC-MS (ESI): m/z 435.47. [M+H]$^+$

8.19: 5-(3-Diethylaminomethyl-1-octyl-1H-indol-5-yl)-pyrimidine-2-carbonitrile $^1$H NMR (400 MHz, CDCl$_3$): δ 0.85 (t, 3H), 1.10 (t, 6H), 1.15-1.40 (m, 10H), 1.75 to 1.90 (m 2H), 2.65 (q, 4H), 3.85 (s, 2H), 4.12 (t, 2H), 7.18 (s, 1H), 7.35-7.50 (m, 2H), 8.00 (s, 1H), 9.10 (s, 2H), $^{13}$C NMR (125 MHz, CDCl$_3$): δ 11.64, 14.07, 22.61, 24.88, 26.95, 29.15, 30.25, 31.74, 46.58, 48.09, 67.10, 75.05, 110.86, 116.13, 119.20, 120.22, 123.03, 129.16, 129.37, 137.22, 137.80, 142.19, 155.42, LC-MS (ESI): m/z 418.59. [M+H]$^+$

8.20: 4-(3-Diethylaminomethyl-1-octyl-1H-indol-5-yl)-benzonitrile $^1$H NMR (400 MHz, CDCl$_3$): δ 0.85 (t, 3H), 1.15-1.40 (m, 16H), 1.75 to 1.90 (m 2H), 2.95 (q, 4H), 4.05-4.2 (m, 4H), 6.95-7.05 (m, 2H), 7.20 (t, 1H), 7.4-7.6 (m, 3H), 7.7-7.85 (m, 2H), LC-MS (ESI): m/z 416.53. [M+H]$^+$

8.21: 3-(3-Diethylaminomethyl-1-octyl-1H-indol-5-yl)-phenol $^1$H NMR (400 MHz, CDCl$_3$): δ 0.85 (t, 3H), 1.15-1.40 (m, 16H), 1.50 (br, 1H) 1.75 to 1.85 (m 2H), 2.95 (q, 4H), 4.05-4.2 (m, 4H), 6.30 (m, 1H), 6.75-6.8 (m, 1H), 6.95 (m, 1H), 7.0-7.2 (m, 3H), 7.3-7.4 (m, 2H), LC-MS (ESI): m/z 407.50. [M+H]$^+$

8.24: 4-(3-Diethylaminomethyl-1-octyl-1H-indol-5-yl)-N-methyl-benzensulfonamide $^1$H NMR (400 MHz, CDCl$_3$): δ 0.85 (t, 3H), 1.15 (t, 6H), 1.20-1.40 (m, 10H), 1.75 to 1.90 (m 2H), 2.75 (q, 4H), 2.85 (s, 3H), 3.90 (s, 2H), 4.12 (t, 2H), 7.10 (d, 1H), 7.20 (t, 1H), 7.30-7.45 (m, 4H), 7.60-7.75 (m, 2H), LC-MS (ESI): m/z 484.47. [M+H]$^+$ Evaluation of Purity of Indoleamines by Reversed Phase HPLC Purity was determined using Waters 2695 Separations Module on a Waters Xterra C18 3.5 μm 3.0×50 mm column with a flow rate of 2.0 mL/min. Two different solvent systems were used: Mobile phase A: H$_2$O with 0.1% TFA, and Mobile Phase B: acetonitrile with 0.1% TFA. Waters 2996 photodiode array detector set at 254 nm was used for detection. The chromatogram was run for six minutes for the detection of major peak corresponding to the target compound.

|  | Mobile phase A | | Mobile phase B | |
|---|---|---|---|---|
| Compound | RT | Area (%) | RT | Area (%) |
| S8.1 | 0.70 | 98.52 | 1.17 | 95.42 |
| S8.2 | 3.44 | 97.03 | 4.82 | 86.19 |
| S8.3 | 2.10 | 99.9 | 4.79 | 99.9 |
| S8.4 | ND | | ND | |
| S8.5 | 3.61 | 91.50 | 4.89 | 89.60 |
| S8.6 | 5.03 | 98.22 | 2.51 | 98.66 |
| S8.7 | 1.02 | 99.90 | 2.20 | 99.76 |
| S8.8 | 1.23 | 91.68 | 3.02 | 93.49 |
| S8.9 | 2.20 | 96.56 | 3.57 | 98.73 |
| S8.10 | 3.09 | 95.31 | 3.01 | 95.54 |
| S8.12 | 2.50 | 98.88 | 4.74 | 99.19 |
| S8.15 | 0.26 | 97.85 | 2.65 | 99.16 |
| S8.17 | 0.28 | 91.45 | 2.28 | 93.59 |
| S8.19 | 1.190 | 91.02 | 3.02 | 97.12 |
| S8.20 | 1.29 | 95.36 | 3.29 | 93.46 |
| S8.21 | 1.19 | 93.16 | 3.15 | 95.73 |
| S8.24 | 1.17 | 96.06 | 3.05 | 96.00 |

Synthesis of Tetrahydrocarbolines

Figure 4:
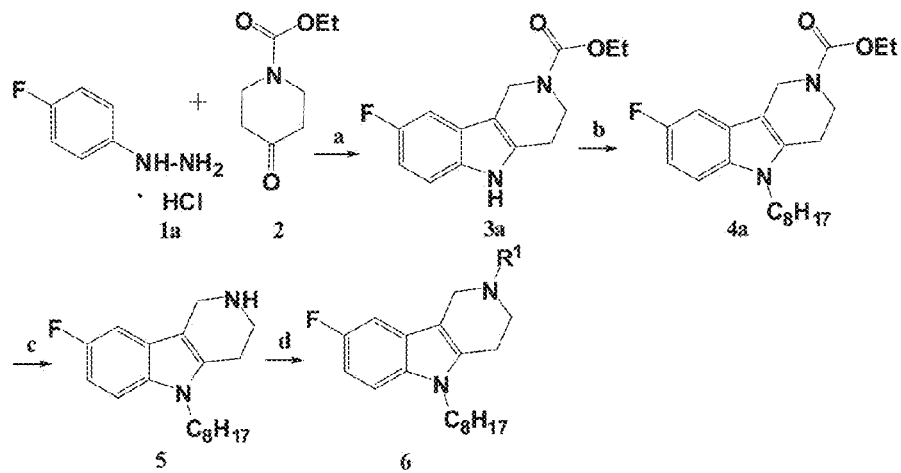
FIG. 4: Synthesis of tetrahydrocarbolines 199 and 205

A scheme for synthesising certain tetrahydrocarbolines is shown in FIG. 4. Reagents and conditions: (a) ethanol, reflux; (b) sodium hydride (NaH, 60%), 1-bromooctane, DMF, 0° C. to rt; (c) potassium hydroxide (KOH, aqueous solution), ethanol, reflux, 16 h; (d) RCHO, NaBH(OAc)$_3$, acetic acid, 1,2-dichloroethane, rt.

Step a. Fischer Indole Synthesis: 2-Carbethoxy-8-fluoro-1,2,3,4-tetrahydropyrido[4,3-b]indole (3a)

The mixture of 4-fluorophenylhydrazine hydrochloride (1a, 1 mmol) and 1-carbethoxy-4-piperidone (2, 1 mmol) in absolute EtOH (20 mL) was refluxed for 3 h. The reaction mixture was allowed to stand at room temperature overnight, and the solid product was collected by filtration, washed with 50% aqueous EtOH, and recrystallized from 95% EtOH to give an off-white solid, yield: 90.6%.

$^1$H NMR (300 Hz, CDCl$_3$) δ 8.11 (s, 1H), 7.23-7.18 (m, 1H), 7.10-7.07 (m, 1H), 6.92-6.85 (m, 1H), 4.64 (s, 2H), 4.20 (q, 2H, J=7.2 Hz), 3.85 (br, 2H), 2.83 (t, 2H, J=5.4 Hz), 1.31 (t, 3H, J=7.2 Hz). $^{13}$C NMR (75 Hz, CDCl$_3$) δ 159.32, 156.22, 132.31, 125.86, 125.74, 111.29, 111.16, 109.77, 109.42, 102.95, 102.64, 61.60, 41.07, 23.44, 18.38, 14.70.

Step b. 2-Carbethoxy-8-fluoro-5-n-octyl-1,2,3,4-tetrahydropyrido[4,3-b]indoles (4a)

To the mixture of 2-carbethoxy-8-fluoro-1,2,3,4-tetrahydropyrido[4,3-b]indoles (3a, 1 mmol) and sodium hydride (60%) (2.5 mmol) was added dry DMF (10 mL) under N$_2$. The reaction mixture was stirred at room temperature for 15 min. The solution of 1-bromooctane in dry DMF (5 mL) was added to the reaction mixture slowly at 0° C. Then the reaction mixture was stirred at room temperature for about 3 h. The reaction mixture was poured into an ice-water, was extracted by dichloromethane (DCM) for four times (15 mL×3). The DCM layer was washed with water for three times (20 mL×3) and brine, respectively, dried with Na$_2$SO$_4$, filtered and concentrated to give brow residue. This residue was purified by silica gel column chromatography to give yellow oil. Yield: 73.9%.

$^1$H NMR (300 Hz, CDCl$_3$) δ 7.20-7.16 (m, 1H), 7.11-7.08 (m, 1H), 6.94-6.88 (m, 1H), 4.65 (s, 2H), 4.20 (q, 2H, J=7.2 Hz), 3.98 (t, 2H, J=7.35 Hz), 3.88 (br, 2H), 2.80 (br, 2H), 1.72-1.68 (m, 2H), 1.33-1.26 (m, 13H), 0.88 (t, 3H, J=6.0 Hz). $^{13}$C NMR (75 Hz, CDCl$_3$) δ 159.09, 155.99, 132.84, 125.23, 125.10, 109.66, 109.53, 109.16, 108.82, 102.86, 102.54, 61.51, 43.24, 41.10, 31.71, 30.29, 29.22, 29.09, 26.97, 22.54, 14.69, 14.00.

Step c. 8-Fluoro-5-n-octyl-1,2,3,4-tetrahydropyrido[4,3-b]indole (5)

To the solution of 2-carbethoxy-8-fluoro-5-n-octyl-1,2,3,4-tetrahydropyrido[4,3-b]indole (4a) in ethanol was added the aqueous solution of potassium hydroxide. The mixture was refluxed for 16 h. The reaction mixture was concentrated to remove ethanol and extracted with DCM for three times (15 mL×3). The DCM layer was washed with brine, dried with Na$_2$SO$_4$, filtered and concentrated to give brow residue. This residue was purified by silica gel column chromatography to give yellow oil. Yield: 67.3%. $^1$H NMR (300 Hz, CDCl$_3$) δ 7.19-7.15 (m, 1H), 7.06-7.02 (m, 1H), 6.91-6.85 (m, 1H), 4.04 (br, 2H), 3.96 (q, 2H, J=7.35 Hz), 3.27 (br, 2H), 2.76 (br, 2H), 1.72-1.68 (m, 2H), 1.29-1.25 (m, 10H), 0.87 (t, 3H, J=6.4 Hz). $^{13}$C NMR (75 Hz, CDCl$_3$) δ 159.06, 155.97, 135.02, 132.51, 125.65, 125.52, 109.49, 109.36, 108.86, 108.52, 102.86, 102.55, 43.11, 31.74, 30.31, 29.27, 29.13, 27.03, 22.56, 14.03. MS (ESI) [M+H]$^+$ 303.2

Step d

2-Substituted-8-fluoro-5-octyl-1,2,3,4-tetrahydropyrido[4,3-b]indoles (6). To the mixture of 8-fluoro-5-octyl-1,2,3,4-tetrahydropyrido[4,3-b]indole (5) and NaBH(OAc)$_3$ was added appropriate aldehyde, 1,2-dichloroethane and acetic acid, respectively. The mixture was stirred at room temperature overnight. The reaction mixture was poured into ice-water, then basified by NaOH aqueous solution to pH=9 at 0° C. The mixture was extracted with DCM for three times (10 mL×3). The DCM layer was washed with brine, dried with Na$_2$SO$_4$, filtered and concentrated to give brow residue. This residue was purified by silica gel column chromatography to give the target compound as oil.

Cpd199.

8-fluoro-2-methyl-5-n-octyl-1,2,3,4-tetrahydropyrido[4,3-b]indole (6a). Off-yellow oil. Yield: 80.9%. $^1$H NMR (300 Hz, CDCl$_3$) δ 7.17-7.13 (m, 1H), 7.06-7.02 (m, 1H), 6.90-6.83 (m, 1H), 3.97 (t, 2H, J=7.35 Hz), 3.62 (s, 2H), 2.84 (s, 4H), 2.55 (s, 3H), 1.72-1.68 (m, 2H), 1.29-1.25 (m, 10H), 0.87 (t, 3H, J=6.45 Hz). $^{13}$C NMR (75 Hz, CDCl$_3$) δ 159.00, 155.91, 134.85, 132.90, 125.69, 125.56, 109.42, 109.29, 108.57, 108.22, 107.70, 107.64, 102.75, 102.44, 52.43, 51.67, 45.74, 43.25, 31.74, 30.27, 29.27, 29.11, 26.99, 23.15, 22.56, 14.02. MS [M+H]$^+$ 317.3

Cpd205.

8-fluoro-2-(4'-hydroxybenzyl)-5-n-octyl-1,2,3,4-tetrahydropyrido[4,3-b]indole (6b). $^1$H NMR (300 Hz, DMSO-d6) δ 9.31 (br, 1H), 7.37-7.32 (m, 1H), 7.15 (d, 2H, J=8.1 Hz), 7.06-7.02 (m, 1H), 6.89-6.83 (m, 1H), 6.73 (d, 2H, J=8.1 Hz), 4.00 (t, 2H, J=6.9 Hz), 3.59 (br, 2H), 3.50 (br, 2H), 2.76 (br, 4H), 1.60 (br, 2H), 1.22-1.20 (m, 10H), 0.83 (t, 3H, J=6.6 Hz). $^{13}$C NMR (75 Hz, DMSO-d6) δ 158.19, 156.27, 155.12, 135.89, 132.56, 129.84, 128.65, 125.19, 125.06, 114.88, 110.09, 109.97, 107.88, 107.54, 107.27, 107.21, 102.22, 101.92, 60.94, 49.53, 49.00, 42.40, 31.12, 29.76, 28.59, 28.55, 26.23, 22.50, 21.97, 13.86. MS [M+H]$^+$ 409.3

Synthesis of Tetrahydrocarbolines 235, 240, 260 and 300

Figure 5:
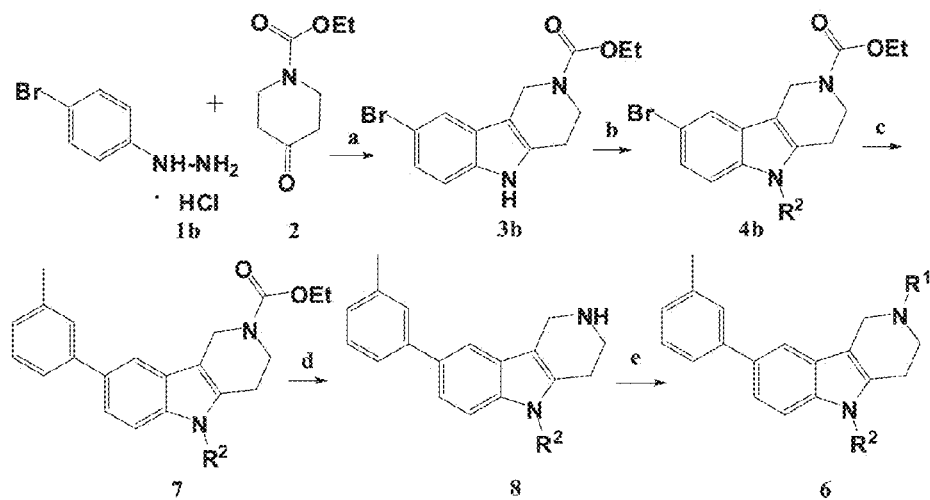
FIG. 5: Synthesis of tetrahydrocarbolines 235, 240, 260 and 300

Synthesis of tetrahydrocarbolines 235, 240, 260 and 300 is shown in FIG. 5. Reagents and conditions: (a) ethanol, reflux; (b) sodium hydride (NaH, 60%), 1-bromooctane, or 1-chloro-3-methylbut-2-ene (isoprenylchloride), DMF, 0° C. to rt; (c) m-tolylboronic acid, Pd(PPh$_3$)$_4$, potassium carbonate (K$_2$CO$_3$, aqueous solution), 1,4-dioxane, N$_2$ atmosphere, reflux, 10 h; (d) potassium hydroxide (KOH, aqueous solution), ethanol, reflux, 16 h; (e) RCHO, NaBH(OAc)$_3$, acetic acid, 1,2-dichloroethane, rt.

Step a. Fischer Indole Synthesis: 2-Carbethoxy-8-bromo-1,2,3,4-tetrahydropyrido[4,3-b]indole (3b)

The mixture of 4-bromophenylhydrazine hydrochloride (1b, 1 mmol) and 1-carbethoxy-4-piperidone (2, 1 mmol) in absolute EtOH (20 mL) was refluxed for 3 h. The reaction mixture was allowed to stand at room temperature overnight, and the solid product was collected by filtration, washed with 50% aqueous EtOH, and recrystallized from 95% EtOH to give an off-white solid, yield: 79.6%. $^1$H NMR (300 Hz, CDCl3) δ 8.17 (br, 1H), 7.56 (s, 1H), 7.23-7.14 (m, 1H), 4.63 (s, 2H), 4.20 (q, 2H, J=7.2 Hz), 3.85 (br, 2H), 2.82 (br, 2H), 1.30 (t, 3H, J=7.2 Hz).

Step b. 2-Carbethoxy-8-bromo-5-n-octyl-1,2,3,4-tetrahydropyrido[4,3-b]indole (4b)

To the mixture of 2-carbethoxy-8-fluoro-1,2,3,4-tetrahydropyrido[4,3-b]indole (3b, 1 mmol) and sodium hydride (60%) (2.5 mmol) was added dry DMF (10 mL) under N$_2$ at 0° C. The reaction mixture was stirred at room temperature for 15 min. The solution of 1-bromooctane in dry DMF (5 mL) was added to the reaction mixture slowly at 0° C. Then the reaction mixture was stirred at room temperature for about 3 h. The reaction mixture was poured into an ice-water, was extracted by dichloromethane (DCM) for four times (15 mL×3). The DCM layer was washed with water for three times (20 mL×3) and brine, respectively, dried with Na$_2$SO$_4$, filtered and concentrated to give brow residue. This residue was purified by silica gel column chromatography to give yellow oil. Yield: 83.5%. $^1$H NMR (300 Hz, CDCl$_3$) δ 7.57-7.568 (m, 1H), 7.25-7.22 (m, 1H), 7.15-7.12 (m, 1H), 4.65 (br, 2H), 4.20 (q, 2H, J=7.2 Hz), 4.20 (t, 2H, J=7.35 Hz), 3.87 (br, 2H), 2.80 (br, 2H), 1.74-1.67 (m, 2H), 1.33-1.25 (m, 13H), 0.87 (t, 3H, J=6.6 Hz). $^{13}$C NMR (75 Hz, CDCl$_3$) δ 155.96, 134.97, 128.98, 128.17, 126.71, 123.69, 120.23, 112.20, 110.53, 106.02, 61.53, 43.21, 41.08, 41.02, 31.71, 30.24, 29.22, 29.09, 26.95, 22.54, 14.70, 14.02.

1-Chloro-3-methylbut-2-ene (isoprenylchloride) as the starting material, and the procedure was the same as compound (4b). 2-Carbethoxy-8-bromo-5-isoprenyl-1,2,3,4-tetrahydropyrido[4,3-b]indole. $^1$H NMR (400 Hz, CDCl$_3$) δ 7.57-7.56 (m, 1H), 7.24-7.21 (m, 1H), 7.13-7.11 (m, 1H), 5.14-5.10 (m, 1H), 4.64 (br, 2H), 4.59-4.57 (d, 2H, J=6.4 Hz), 4.19 (q, 2H, J=7.2 Hz), 3.86 (t, 2H, J=5.2 Hz), 2.79 (t, 2H, J=5.6 Hz), 1.81 (d, 3H, J=0.8 Hz), 1.70 (d, 3H, J=0.9 Hz), 1.30 (t, 3H, J=7.2 Hz). $^{13}$C NMR (100 Hz, CDCl$_3$) δ 171.11, 155.89, 135.14, 134.94, 126.83, 123.75, 120.25, 119.97, 112.33, 110.59, 106.32, 61.53, 60.35, 41.29, 41.14, 41.04, 25.51, 18.04, 14.71.

Step c. 2-Carbethoxy-8-m-tolyl-5-n-octyl-1,2,3,4-tetrahydropyrido[4,3-b]indole (7)

To the mixture of 2-Carbethoxy-8-bromo-5-n-octyl-1,2,3,4-tetrahydropyrido[4,3-b]indole (4b, 1 equiv.), m-tolyboronic acid (1.1 equiv.) and Pd(PPh$_3$)$_4$ (0.05 equiv.) in 12 mL 1,4-dioxane was added 4 mL aqueous solution of K$_2$CO$_3$ (3 equiv.). The mixture was refluxed under N$_2$ atmosphere for about 10 h. On cooling, the solvent was evaporated and the resulting residue was extracted with DCM (20 mL×3), the DCM layer was washed with brine, dried (Na$_2$SO$_4$) and filtered. The residue obtained on removal of the solvent was purified by column chromatography on silica gel with EtOAc/hexane as eluting solvents to give the target compound 2-carbethoxy-8-m-tolyl-5-octyl-1,2,3,4-tetrahydropyrido[4,3-b]indole (7). Yield: 60.4%. $^1$H NMR (300 Hz, CDCl$_3$) δ 7.67 (br, 1H), 7.48-7.43 (m, 3H), 7.35-7.31 (m, 2H), 7.15-7.12 (m, 1H), 4.76 (s, 2H), 4.22 (q, 2H, J=7.2 Hz), 4.03 (t, 2H, J=7.2 Hz), 3.91 (br, 2H), 2.84 (br, 2H), 2.45 (s, 3H), 1.77-1.73 (m, 2H), 1.35-1.27 (m, 13H), 0.89 (t, 3H, J=6.5 Hz). $^{13}$C NMR (75 Hz, CDCl$_3$) δ 156.09, 142.48, 138.10, 135.83, 132.72, 128.50, 128.09, 126.98, 125.57, 124.39, 120.83, 118.99, 116.15, 109.29, 106.70, 61.49, 60.36, 43.21, 41.31, 31.75, 30.38, 29.28, 29.13, 27.04, 22.57, 21.56, 14.73, 14.16, 14.03.

Step d. 8-m-Tolyl-5-n-octyl-1,2,3,4-tetrahydropyrido[4,3-b]indole (8)

To the solution of 2-carbethoxy-8-m-tolyl-5-n-octyl-1,2,3,4-tetrahydropyrido[4,3-b]indole (7) in ethanol was added the aqueous solution of potassium hydroxide. The mixture was refluxed for 16 h. The reaction mixture was concentrated to remove ethanol and extracted with DCM for three times (15 mL×3). The DCM layer was washed with brine, dried with Na$_2$SO$_4$, filtered and concentrated to give brow residue. This residue was purified by silica gel column chromatography to give yellow oil. Yield: 63.6%. $^1$H NMR (300 Hz, CDCl$_3$) δ 7.62 (br, 1H), 7.48-7.41 (m, 3H), 7.36-7.32 (m, 2H), 7.15-7.12 (m, 1H), 4.12 (br, 2H), 3.99 (t, 2H, J=7.2 Hz), 3.31 (br, 2H), 2.91 (br, 1H), 2.79 (br, 2H), 2.45 (s, 3H), 1.77-1.73 (m, 2H), 1.32-1.28 (s, 10H), 0.90 (t, 3H, J=6.6 Hz). $^{13}$C NMR (75 Hz, CDCl$_3$) δ 142.57, 138.05, 135.45, 133.83, 132.48, 128.46, 128.06, 126.89, 125.91, 124.37, 120.56, 116.20, 109.13, 108.09, 43.26, 43.01, 42.14, 31.75, 30.35, 29.28, 29.14, 27.05, 23.10, 22.56, 21.55, 14.03.

Step e. 2-Substituted-8-m-tolyl-5-n-octyl-1,2,3,4-tetrahydropyrido[4,3-b]indoles (6)

To the mixture of 8-m-tolyl-5-octyl-1,2,3,4-tetrahydropyrido[4,3-b]indole (8) and NaBH(OAc)$_3$ was added appropriate aldehyde, 1, 2-dichloroethane and acetic acid, respectively. The mixture was stirred at room temperature overnight. The reaction mixture was poured into ice-water, then basified by NaOH aqueous solution to Ph=9 at 0° C. The mixture was extracted with DCM for three times (10 mL×3). The DCM layer was washed with brine, dried with Na$_2$SO$_4$, filtered and concentrated to give brow residue. This residue was purified by silica gel column chromatography to give an oil product.

Cpd240.

2-(4'-hydroxybenzyl)-8-m-tolyl-5-n-octyl-1,2,3,4-tetrahydropyrido[4,3-b]indoles (6c). Off-yellow solid. Yield: 33.4%. $^1$H NMR (300 Hz, CD$_3$OD) δ 7.52 (s, 1H), 7.43-7.35 (m, 4H), 7.29-7.23 (m, 3H), 7.08-7.06 (m, 1H), 6.80-6.78 (m, 2H), 4.07 (t, 2H, J=6.6 Hz), 3.74-3.73 (m, 4H), 2.92-2.88 (m, 4H), 2.39 (s, 3H), 1.73 (br, 2H), 1.29-1.26 (m, 10H), 0.87 (t, 3H, J=6.6 Hz).

$^{13}$C NMR (75 Hz, CDCl$_3$) δ 156.28, 142.63, 139.69, 139.64, 138.04, 135.90, 133.98, 132.36, 129.40, 128.45, 128.06, 126.86, 126.09, 124.38, 121.22, 120.37, 116.20, 114.57, 109.13, 107.64, 61.97, 50.23, 49.77, 43.24, 31.79, 30.36, 29.31, 29.16, 27.08, 22.68, 22.59, 21.56, 14.06. MS [M+H]$^+$ 481.3

Cpd300.

2-(4'-hydroxybenzyl)-5-isoprenyl-8-m-tolyl-1,2,3,4-tetrahydropyrido[4,3-b]indoles (6d). Off-yellow solid. Yield: 35.3%. $^1$H NMR (400 Hz, CDCl$_3$) δ 7.46 (br, 1H), 7.42-7.37 (m, 3H), 7.33 (br, 1H), 7.31-7.28 (m, 3H), 7.10-7.08 (m, 1H), 6.87-6.85 (m, 2H), 5.19-5.16 (m, 1H), 4.61 (d, 2H, J=6.4 Hz), 4.07 (br, 2H), 3.97 (br, 2H), 3.26 (br, 2H), 3.02 (br, 2H), 2.39 (s, 3H), 1.82 (br, 3H), 1.71 (br, 3H). $^{13}$C NMR (100 Hz, CDCl$_3$) δ 142.23, 138.18, 136.12, 135.25, 133.18, 132.56, 131.77, 128.86, 128.54, 128.09, 127.12, 125.65, 124.40, 121.38, 120.07, 116.12, 116.08, 115.48, 109.56, 105.91, 49.03, 48.45, 41.57, 25.56, 21.55, 18.31, 18.11. MS [M+H]$^+$437.1

Cpd235.

2-methyl-8-m-tolyl-5-n-octyl-1,2,3,4-tetrahydropyrido[4,3-b]indoles (6e). Off-yellow oil. Yield: 98.3%. $^1$H NMR (300 Hz, CDCl$_3$) δ 7.61 (br, 1H), 7.47-7.40 (m, 3H), 7.35-7.31 (m, 2H), 7.14-7.11 (m, 1H), 4.02 (t, 2H, J=7.2 Hz), 3.84 (br, 2H), 2.99-2.97 (m, 2H), 2.94-2.92 (m, 2H), 2.62 (s, 3H), 2.44 (s, 3H), 1.78-1.73 (m, 2H), 1.31-1.27 (m, 10H), 0.88 (t, 3H, J=6.45 Hz). $^{13}$C NMR (75 Hz, CDCl$_3$) δ 142.62, 138.06, 135.93, 133.22, 132.53, 128.47, 128.11, 126.90, 125.93, 124.39, 120.57, 116.18, 109.21, 106.89, 51.88, 51.28, 44.70, 43.28, 31.77, 30.33, 29.31, 29.14, 27.04, 22.57, 22.24, 21.55, 14.03. MS [M+H]$^+$ 389.2

Cpd260.

2-isopropyl-8-m-tolyl-5-n-octyl-1,2,3,4-tetrahydropyrido[4,3-b]indoles (6f). Off-yellow oil. Yield: 24.7%. $^1$H NMR (300 Hz, CDCl$_3$) δ 7.62 (br, 1H), 7.48-7.41 (m, 3H), 7.35-7.30 (m, 2H), 7.14-7.12 (m, 1H), 4.02-3.97 (m, 4H), 3.28-3.20 (m, 1H), 3.11 (t, 2H, J=5.4 Hz), 2.99 (t, 2H, J=5.1 Hz), 2.44 (s, 3H), 1.77-1.73 (m, 2H), 1.33-1.28 (m, 16H), 0.90 (t, 3H, J=6.6 Hz). $^{13}$C NMR (75 Hz, CDCl$_3$) δ 142.49, 137.99, 136.01, 133.37, 132.47, 128.41, 127.99, 126.85, 125.95, 124.30, 120.59, 115.96, 109.20, 106.16, 54.81, 46.58, 44.39, 43.25, 31.71, 30.31, 29.23, 29.08, 27.00, 22.52, 21.49, 18.25, 13.98. MS [M+H]$^+$ 417.2

Figure 6:
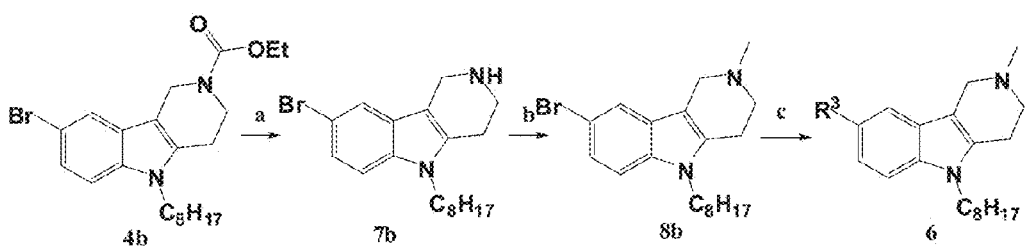
FIG. 6: Synthesis of tetrahydrocarboline 305 and 306

A scheme for synthesis of tetrahydrocarbolines 305 and 306 is shown in FIG. 6. Reagents and conditions: (a) potassium hydroxide (KOH, aqueous solution), ethanol, reflux, 16 h; (b) formaldehyde, NaBH(OAc)$_3$, acetic acid, 1,2-dichloroethane, rt; (c) appropriate boronic acid or boronic acid pinacol ester, Pd(PPh$_3$)$_4$, potassium carbonate (K$_2$CO$_3$, aqueous solution), 1, 4-dioxane, microwave, 110° C., 0.5 h.

Step a. 8-Bromo-5-n-octyl-1,2,3,4-tetrahydropyrido[4,3-b]indole (7b)

To the solution of 2-carbethoxy-8-bromo-5-n-octyl-1,2,3,4-tetrahydropyrido[4,3-b]indole (4b) in ethanol was added the aqueous solution of potassium hydroxide. The mixture was refluxed for 16 h. The reaction mixture was concentrated to remove ethanol and extracted with DCM for three times (15 mL×3). The DCM layer was washed with brine, dried with Na$_2$SO$_4$, filtered and concentrated to give brow residue. This residue was purified by silica gel column chromatography to give yellow oil. Yield: 74.5%.

Step b. 2-methyl-8-bromo-5-n-octyl-1,2,3,4-tetrahydropyrido[4,3-b]indoles (8b)

To the mixture of 8-bromo-5-n-octyl-1,2,3,4-tetrahydropyrido[4,3-b]indole (7b) and NaBH(OAc)$_3$ was added formaldehyde, 1,2-dichloroethane and acetic acid, respectively. The mixture was stirred at room temperature overnight. The reaction mixture was poured into ice-water, then basified by NaOH aqueous solution to Ph=9 at 0° C. The mixture was extracted with DCM for three times (10 mL×3). The DCM layer was washed with brine, dried with Na$_2$SO$_4$, filtered and concentrated to give brow residue. This residue was purified by silica gel column chromatography to give an oil product. Yield: 60.3%. $^1$H NMR (400 Hz, CDCl$_3$) δ 7.50-7.50 (m, 1H), 7.25-7.22 (m, 1H), 7.15-7.12 (m, 1H), 3.99-3.94 (m, 4H), 3.17 (t, 2H, J=5.6 Hz), 2.98 (t, 2H, J=5.6 Hz), 2.70 (s, 3H), 1.72-1.68 (m, 2H), 1.28-1.24 (m, 10H), 0.86 (t, 3H, J=6.8 Hz). MS [M+H]$^+$377.0, 379.1.

Step c. 8-substituted-2-methyl-5-n-octyl-1,2,3,4-tetrahydropyrido[4,3-b]indole (6)

To the mixture of 2-methyl-8-bromo-5-n-octyl-1,2,3,4-tetrahydropyrido[4,3-b]indoles (8b, 1 equiv.), appropriate boronic acid or boronic acid pinacol ester (1.1 equiv.) and Pd(PPh$_3$)$_4$ (0.05 equiv.) in 2 mL 1,4-dioxane was added 0.5 mL aqueous solution of K$_2$CO$_3$ (3 equiv.). The mixture was stirred at 110° C. under microwave for about 0.5 h. On cooling, the solvent was evaporated and the resulting residue was extracted with DCM (10 mL×3), the DCM layer was washed with brine, dried (Na$_2$SO$_4$) and filtered. The residue obtained on removal of the solvent was purified by column chromatography on silica gel with EtOAc/hexane as eluting solvents to give the target compound (6).

Cpd305

8-(2'-amino-pyrimidin-5'-yl)-2-methyl-5-n-octyl-1,2,3,4-tetrahydropyrido[4,3-b]indole (6 g). Yield: 48.2%. $^1$H NMR (400 Hz, CDCl$_3$) δ 8.55 (br, 2H), 7.47-7.46 (m, 1H), 7.34-7.32 (m, 1H), 7.25-7.23 (m, 1H), 5.12 (br, 2H), 4.02 (t, 2H, J=7.2 Hz), 3.83 (s, 2H), 2.97-2.94 (m, 4H), 2.64 (s, 3H), 1.77-1.70 (m, 2H), 1.30-1.24 (m, 10H), 0.86 (t, 3H, J=6.8 Hz). $^{13}$C NMR (100 Hz, CDCl$_3$) δ 161.61, 156.48, 136.04, 133.71, 126.56, 126.17, 126.10, 119.42, 115.22, 109.77, 106.98, 52.26, 51.61, 45.17, 43.34, 31.76, 30.32, 29.29, 29.12, 27.03, 22.57, 22.55, 14.03. MS [M+H]$^+$ 392.2, 390.2

Cpd306

2-methyl-8-(4'-(methylsulfonyl)phenyl)-5-n-octyl-1,2,3,4-tetrahydropyrido[4,3-b]indole (6 h). Yield: 47.1%. $^1$H NMR (400 Hz, CDCl$_3$) δ 7.98-7.96 (m, 2H), 7.81-7.79 (m, 2H), 7.63 (br, 1H), 7.44-7.42 (m, 1H), 7.38-7.35 (m, 1H), 4.04 (t, 2H, J=7.2 Hz), 3.99 (br, 2H), 3.14 (t, 2H, J=5.6 Hz), 3.09 (s, 3H), 3.01 (t, 2H, J=5.2 Hz), 2.71 (s, 3H), 1.77-1.74 (m, 2H), 1.31-1.25 (m, 10H), 0.87 (t, 3H, J=6.8 Hz). $^{13}$C NMR (100 Hz, CDCl$_3$) δ 175.49, 148.05, 137.87, 136.71, 133.30, 130.34, 127.83, 127.75, 125.90, 120.75, 116.73, 109.82, 105.87, 67.05, 53.39, 51.54, 50.96, 44.68, 44.01, 43.48, 31.74, 30.29, 29.26, 29.12, 27.02, 22.56, 14.02. MS (ESI) [M+H]$^+$ 453.2

Figure 7:
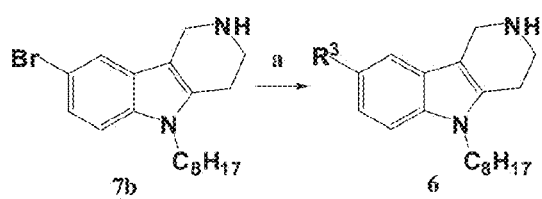
FIG. 7: Synthesis of tetrahydrocarbolines 309, 314 and 315

FIG. 7 shows the synthesis of tetrahydrocarbolines 309, 314 and 315. Reagents and conditions: (a) appropriate boronic acid or boronic acid pinacol ester, Pd(PPh$_3$)$_4$, potassium carbonate (K$_2$CO$_3$, aqueous solution), 1,4-dioxane, microwave, 110° C., 0.5 h.

Step a. 8-substituted-5-n-octyl-1,2,3,4-tetrahydropyrido[4,3-b]indole (6). To the mixture of 8-bromo-5-n-octyl-1,2,3,4-tetrahydropyrido[4,3-b]indoles (7b, 1 equiv.), appropriate boronic acid or boronic acid pinacol ester (1.1 equiv.) and Pd(PPh$_3$)$_4$ (0.05 equiv.) in 2 mL 1,4-dioxane was added 0.5 mL aqueous solution of K$_2$CO$_3$ (3 equiv.). The mixture was stirred at 110° C. under microwave for about 0.5 h. On cooling, the solvent was evaporated and the resulting residue was extracted with DCM (10 mL×3), the DCM layer was washed with brine, dried (Na$_2$SO$_4$) and filtered. The residue obtained on removal of the solvent was purified by column chromatography on silica gel with EtOAc/hexane as eluting solvents to give the target compound (6).

Cpd309

8-(2'-amino-pyrimidin-5-yl)-5-n-octyl-1,2,3,4-tetrahydropyrido[4,3-b]indole (6i). Yield: 47.1%. $^1$H NMR (400 Hz, CDCl$_3$) δ 8.55 (br, 2H), 7.47 (br, 1H), 7.35-7.33 (m, 1H), 7.25-7.23 (m, 1H), 5.22 (br, 2H), 4.12 (br, 2H), 4.01 (t, 2H, J=7.2 Hz), 3.28 (t, 2H, J=4.8 Hz), 2.90-2.86 (m, 1H), 2.78 (br, 2H), 1.75-1.68 (m, 2H), 1.30-1.25 (m, 10H), 0.86 (t, 3H, J=6.8 Hz). $^{13}$C NMR (100 Hz, CDCl$_3$) δ 161.63, 156.53, 156.44, 135.52, 134.62, 126.52, 126.23, 126.04, 119.27, 115.28, 109.62, 108.71, 43.43, 43.05, 42.26, 31.74, 30.34, 29.27, 29.12, 27.04, 23.45, 22.55, 14.01. MS [M+H]$^+$ 378.0, 376.2

Cpd314

8-(4'-(methylsulfonyl)phenyl)-5-n-octyl-1,2,3,4-tetrahydropyrido[4,3-b]indole (6j). Yield: 49.6%. $^1$H NMR (400 Hz, CDCl$_3$) δ 7.96 (d, 2H, J=8.4 Hz), 7.79 (d, 2H, J=8.4 Hz), 7.63 (br, 1H), 7.43-7.41 (m, 1H), 7.37-7.35 (m, 1H), 4.29 (br, 2H), 4.02 (t, 2H, J=7.2 Hz), 3.44 (br, 2H), 3.09 (s, 3H), 2.96 (br, 2H), 1.76-1.71 (m, 2H), 1.31-1.25 (br, 10H), 0.87 (t, 3H, J=6.8 Hz). $^{13}$C NMR (100 Hz, CDCl$_3$) δ 147.91, 137.92, 136.43, 133.45, 130.44, 128.06, 127.81, 127.76, 127.70, 125.84, 120.93, 116.84, 109.82, 44.68, 43.38, 31.74, 30.32, 29.25, 29.12, 27.04, 22.56, 14.03. MS [M+H]$^+$ 439.2.

Cpd315

8-(2'-fluoropyridin-4-yl)-5-n-octyl-1,2,3,4-tetrahydro-1H-pyrido[4,3-b]indole (6k). Yield: 34.7%. $^1$H NMR (400 Hz, CDCl$_3$) δ 8.18 (d, 1H, J=5.2 Hz), 7.68 (d, 1H, J=5.6 Hz), 7.44-7.40 (m, 2H), 7.36-7.34 (m, 1H), 7.15 (br, 1H), 4.11 (br, 2H), 4.01 (t, 2H, J=7.2 Hz), 3.27 (t, 2H, J=5.2 Hz), 2.77 (t, 2H, J=5.2 Hz), 2.53 (br, 1H), 1.75-1.72 (m, 2H), 1.31-1.25 (m, 10H), 0.87 (t, 3H, J=6.8 Hz). $^{13}$C NMR (100 Hz, CDCl$_3$) δ 165.71, 163.36, 155.52, 155.44, 147.47, 147.31, 136.68, 135.13, 127.61, 127.58, 126.12, 119.66, 119.36, 119.33, 116.48, 109.58, 106.60, 106.23, 43.32, 43.05, 42.12, 31.68, 30.28, 29.21, 29.06, 26.96, 23.39, 22.50, 13.96. MS [M+H]$^+$ 380.2.

Evaluation of Purity of Tetrahydrocarbolines by Reversed Phase HPLC

Purity of final compounds was verified by reverse phase HPLC on two different solvent systems and found to be ≥95%. Purity was tested on an Agilent 1100 series HPLC system with a Luna 5u C18(2) 100A column (100×4.6 mm, 10 μm). The mobile phase flow rate was 1.0 mL/min. Chromatogram was run for at least for 10 mins for the detection of the major peak corresponding to the target compound.

| Compound | Mobile Phase A$^a$ (area %)$^c$ | | Mobile Phase B (area %)$^c$ | |
| --- | --- | --- | --- | --- |
| | 254 nm | 280 nm | 254 nm | 280 nm |
| 199 | 95.26$^d$ | 95.02 | 96.11$^d$ | 95.35 |
| 205 | 95.19 | 95.78 | 95.49 | 97.89 |
| 240 | 98.41 | 95.55 | 97.75 | 96.76 |
| 300 | 96.16 | 99.35 | 95.13 | 98.44 |
| 235 | 98.18 | 98.14 | 97.89 | 97.41 |
| 260 | 95.75 | 95.61 | 95.82 | 96.31 |
| 305 | 98.87 | 97.67 | 97.31 | 95.32 |
| 306 | 95.91 | 98.78 | 95.74 | 99.47 |
| 309 | 96.89 | 96.26 | 97.53 | 95.44 |
| 314 | 95.74 | 95.24 | 95.18 | 95.61 |
| 315 | 96.73 | 95.41 | 97.18 | 95.16 |

Mobile Phase A: acetonitrile (95%) and water (5%) + 0.1% triethylamine (TEA)
Mobile Phase B: methanol (95%) and water (5%) + 0.1% triethylamine (TEA) Area (%) of Major Peak = [Area of Major Peak/Total Area of All Peaks] × 100 Wavelength 300 mn Evaluation of Icmt Inhibition Isoprenylcysteine carboxyl methyltransferase (Icmt) was provided by Prof PJ Casey of Duke University, NC. S-Adenosylmethionine (SAM), magnesium chloride Hexahydrate (MgCl$_2$), tartrazine, 4-(2-hydroxyethyl)-1-piperazineethanesulfonic acid (HEPES), dimethyl sulfoxide (DMSO) and dithiotreitol (DTT) were purchased from Sigma (Mo, USA). [$^3$H] S-Adenosylmethionine, [$^3$H] Biotin and Streptavidin PVT SPA Beads were purchased from PerkinElmer (Waltham, Mass.). Assays were performed in black small volume 384 well microtitre plates from PerkinElmer.

Stocks of Icmt membrane protein (30 μg/μL) stored at −80° C. were thawed at 37° C. and placed on ice. The Icmt membrane protein was diluted in assay buffer (70 mM HEPES, 100 mM NaCl, 5 mM Mg Cl$_2$ and 3 mM DTT, pH 7.5) to a 0.03 μg/μL working concentration and added to the wells of a microtitre plate (5 μl/well). To each wells 20 μl of the reaction buffer was added. The reaction was initiated with the addition of 5 μL of substrate solution containing BFC (6 μM), SAM (3 μM) and 30 μCi/mL [$^3$H] SAM (all of these reagents were stored at −20° C., SAM reagents thawed on ice, BFC thawed at RT). The plate was incubated at 37° C. for 30 minutes. The reaction was stopped with the addition of 15 μL of stop solution containing SAM (150 μM) and Streptavidin SPA beads (20 mg/mL). Following overnight incubation at ambient temperature radioactivity was counted on a Microbeta Trilux™ (Perkin Elmer, Turku, Finland).

Evaluation of Antiproliferative Activity.

The MDA-MB-231 human breast cells and PC3 Prostrate cancer cells were maintained at 37° C. with 5% CO$_2$ in DMEM (Invitrogen) supplemented with 10% fetal bovine serum (FBS, Hyclone), 50 U/ml penicillin (Gibco), and 50 μg/ml streptomycin (Gibco). For proliferation assays, cells were seeded at 2500 cells per well in DMEM containing 5% FBS in 96-well plates for 24 h prior to treatment with specific test compound or vehicle at various concentrations for 72 h. The relative number of the live cells was determined using the CellTiter® 96 AQueous One Solution Cell Proliferation Assay (Promega). Determinations were made in duplicates or triplicates.

Determination of Solubility

Determination of aqueous solubility was carried out on Multiscreen® Solubility filter plates (Millipore-MSS-LBPC10) from Millipore Corporation (MA, USA). The protocol (PC2445EN00, Millipore Corporation) was followed. Briefly, various concentrations of the test compound were prepared in Universal buffer (pH 7.4)/acetonitrile/DMSO. The UV absorbances of these solutions were obtained at a pre-determined wavelength and used to construct a calibration curve for the test compound. Next, a stock solution of the test compound in DMSO was prepared at a known concentration, diluted with Universal buffer (pH 7.4), dispensed into wells in the Multiscreen Solubility filter plate, and agitated for a period of time. The suspension is then filtered, the filtrate collected and diluted with acetonitrile to give the same solvent composition used to prepare the calibration solutions. The absorbance of the diluted filtrate was then read at the predetermined wavelength and the concentration of the filtrate (taken here to be equivalent to the solubility of the test compound) was determined from the calibration curve.

Further Testing

The following additional results were obtained for compound 8-7, 8-12, 8-15 and 305. For comparison purposes, corresponding results are also provided for cysmethynil.

|  | cysmethynil | 8-7 | 8-15 | 8-12 | 305 |
|---|---|---|---|---|---|
| ClogP | 7.0 | 7.6 | 6.6 | 6.6 | 5.8 |
| Log $D_{7.4}$ | 6.9 | 4.6 | 3.8 | 3.5 | 3.2 |
| $IC_{50\ Icmt}$ (μM) | 1.90 (0.28) | 1.80 | 1.60 | 0.86 (0.09) | 3.30 |
| $IC_{50\ MDA\text{-}MB\text{-}231}$ (μM) | 27.4 (1.10) | 6.01 (0.24) | 13.25 (0.16) | 2.48 (0.07) | 5.65 (0.31) |
| $IC_{50\ HepG2}$ (μM) | 21.8 (0.20) | —[c] | —[c] | 1.65 (0.23) | 1.73 (0.22) |
| $IC_{50\ IMR90}$ (μM) | 29.19 (1.89) | 5.52 (0.09) | 9.84 (0.94) | 2.65 (0.15) | 5.29 (0.09) |
| Solubility (μM)[d] | 1.14 (0.1) | 244.8 (9.7) | 271.56 (6.63) | 155.9 (6.4) | 40.6 (1.75) |
| PAMPA $P_e$ ($\times 10^{-6}$ cm/s)[d] | Nil[e] | —[c] | —[c] | 14.2 (1.4) | 19.66 ± 0.56 |
| DLS count rate (kcps)[f] |  |  |  |  |  |
| 10 μM | 164.0 | 16.5 | 28.9 | 53.3 | 29.0 |
| 1 μM | 22.6 | 16.8 | 20.4 | 24.5 | 21.0 |
| Half-life (min) | 44.8 (8.0) | —[c] | —[c] | 11.3 (0.4) | 31.6 (7.7) |
| Intrinsic Clearance (μL/min/mg) | 53.6 (9.0) | —[c] | —[c] | 204.0 (9.0) | 76.6 (21) |

[a]Estimated with ChemDraw Ultra 12.0 (ClogP) and ACD/Labs 12.0 (log D 7.4).
[b]Mean (SD) of at least 3 determinations or mean of 2 separate determinations.
[c]Not attempted.
[d]Determinations were made pH 7.4, 24 h (solubility) or 16 h (PAMPA $P_e$) agitation. Mean (SD) of 3 separate determinations.
[e]Could not be determined under existing experiental conditions.
[f]Mean count rates (kilocount per sec) from 3 separate determinations at 10 μM or 1 μM (1% DMSO, potassium phosphate buffer 5 mM pH 7.4).

Test methods are set out below.

Determination of Icmt Inhibition

Sf9 (*Spodoptera frugiperda* ovarian) membranes containing recombinant Icmt were provided by Prof PJ Casey (Duke University, NC and Duke-NUS Graduate Medical School). S-Adenosylmethionine (SAM), magnesium chloride hexahydrate, tartrazine, 4-(2-hydroxyethyl)-1-piperazineethanesulfonic acid (HEPES) and dithiotreitol (DTT) were purchased from Sigma (Mo, USA). [$^3$H] S-Adenosylmethionine, [$^3$H] biotin and streptavidin PVT SPA Beads were purchased from PerkinElmer (Waltham, Mass.). Biotinylated farnesylcysteine was synthesized as described in an earlier report. Assays were performed in black 384-well microtitre plates from PerkinElmer.

A vial of Icmt membrane protein (30 μg/μL) stored at −80° C. was thawed at 37° C. and placed on ice. The protein was diluted in assay buffer (70 mM HEPES, 100 mM NaCl, 5 mM MgCl$_2$, 3 mM DTT, pH 7.5) to 0.03 μg/μL and aliquots were added to each well (5 μL/well), followed by 20 μL of the assay buffer. The reaction was initiated by adding 5 μL of a solution containing biotinylated BFC (6 μM), SAM (3 μM) and 30 μCi/mL [$^3$H] SAM. These reagents were stored at −20° C. and thawed on ice (SAM, [$^3$H] SAM) or at room temperature (BFC). The plate was incubated at 37° C. for 30 minutes after which the reaction was quenched by adding 15 μL of a solution comprising SAM (150 μM) and streptavidin SPA beads (20 mg/mL). After overnight incubation at ambient temperature, radioactivity was counted (Microbeta Trilux™, Perkin Elmer, Turku, Finland). The degree of inhibition was assessed from the radioactivity obtained in presence of test compound compared to that obtained from the control sample with test compound. Two independent determinations were made for each test compound.

Cell-Based Growth Inhibitory Determination

Human breast cancer MDA-MB231, liver cancer HepG2 and lung fibroblast cells were purchased from ATCC (Rockville, Md.). MDA-MB231 cells and IMR-90 cells were grown in DMEM (Sigma Aldrich, Singapore) and EMEM (Sigma Aldrich, Singapore) respectively at 37° C., 5% CO$_2$. DMEM was supplemented with 10% fetal bovine serum (Invitrogen, heat treated at 65 deg C., 30 min), 50 units/L penicillin-G and 50 μg/mL streptomycin. EMEM was supplemented with 10% fetal bovine serum (heat treated as above), 100 mg/L penicillin-G and 100 μg/mL streptomycin. MDA-MB231 and IMR-90 were subcultured at 80-90% confluency and used within 15-28 passages and 4-10 passages respectively. HepG2 cell lines were cultured in DMEM high glucose with 10% v/v fetal bovine serum (heat treated as described earlier), 100 mg/L penicillin G and 100 μg/mL streptomycin. HepG2 cells were subcultured at 80-90% confluency and used within 7-10 passages.

Cell viability was assessed using CellTitre 96® Aqueous One Solution (Promega, Madison, Wis.) containing the tetrazolium salt 3-(4,5-dimethylthiazol-2-yl)-5-(3-carboxymethoxyphenyl)-2-(4-sulfophenyl)-2H-tetrazolium (MTS). Seeding densities were 2400 cells/well (MDA-MB-231), 4000 cells/well (IMR90) and 7500 cells/well (HepG2). Cells were grown on 96-well plates for 24 h before aliquots of test compounds were added to each well and the plates were incubated for 72 h. Final concentration of DMSO per well was maintained at 0.5% v/v. At the end of the incubation period, 20 μL of the MTS solution was added to each well and the plates were incubated for another 4 h before absorbance readings at 490 nm were taken (Tecan Infinite M200 Microplate reader). Cell viability was determined from the expression:

$$\text{Cell Viability} = \frac{(Absorbance_{cells+cpd} - Absorbance_{cpd})}{[((Absorbance)]_{cell+vc} - Absorbance_{vc})} \times 100\%$$

Where $Absorbance_{cells+cpd}$=absorbance of wells containing cells in vehicle (media+0.5% DMSO) in the presence of test compound $Absorbance_{cpd}$=absorbance of wells containing vehicle and test compound (to account for absorbance due to test compound at 490 nm)

$Absorbance_{cells+vc}$=absorbance of wells containing untreated cells and vehicle (vc)

$Absorbance_{vc}$=absorbance of wells containing only vehicle (vc).

% Viability readings were plotted against log concentration on GraphPad Prism (Version 5.0, GraphPad Software, San Diego, Calif.) to give a sigmoidal curve from which IC$_{50}$ (concentration required to reduce viability by 50% compared to control/untreated cells) was obtained. The plot was constrained to ≥0 and ≤100%. At least 3 independent determinations of IC$_{50}$ were made using two different stock solutions of test compound.

Figure 8:
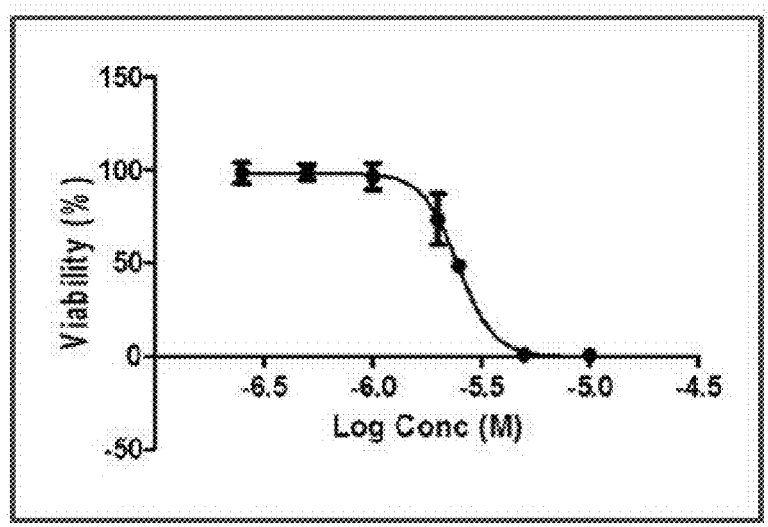
FIG. 8: Representative viability vs concentration plots for cysmethynil and 8-12
Figure 8:
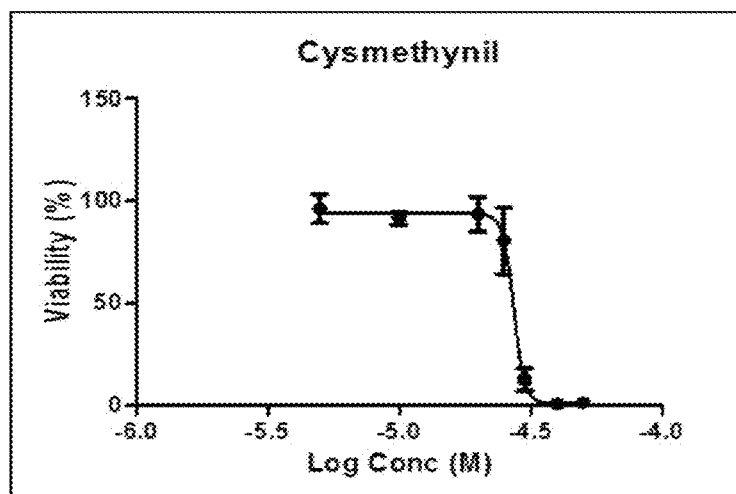

Representative viability vs concentration plots for cysmethynil and 4-12 are shown in FIG. 8.

Determination of Aqueous Solubility

Determination of aqueous solubility was carried out on Multiscreen® Solubility filter plates (Millipore-MSS-LBPC10) from Millipore Corporation (MA, USA). The protocol (PC2445EN00, Millipore Corporation) was followed. Briefly, various concentrations of the test compound were prepared in Universal buffer (pH 7.4)/acetonitrile/ DMSO. The UV absorbances of these solutions were obtained at a pre-determined wavelength and used to construct a calibration curve for the test compound. Next, a stock solution of the test compound in DMSO was prepared at a known concentration, diluted with Universal buffer (pH 7.4), dispensed into wells in the Multiscreen Solubility filter plate, and agitated for 24 hours at room temperature (25 deg C.). Final concentration of DMSO per well was 1% v/v except for 8-7 and 8-15 where it was 1.5% v/v. The suspension was filtered, the filtrate collected and diluted with acetonitrile to give the same solvent composition used to prepare the calibration solutions. The absorbance of the diluted filtrate was read at the predetermined wavelength and the concentration of the filtrate (equivalent to the solubility of the test compound) was determined from the calibration curve. The concentration of cysmethynil was determined by LC-MS because of their low solubilities which could not be quantified by uv. LCMS determinations were made on an Agilent 1200 Series HPLC linked to a AB Sciex Instruments 3200 Q TRAP LC/MS/MS. Separations were carried out on a Phenomenex Luna column [3u, C$_{18}$(2), 100A, 5×4.6 mm]. The internal standard was diethyl-[5(4-methanesulfonyl-phenyl)-1-octyl-1H-indol-3yl methyl]-amine for cysmethynil and 7. The internal standard for 2 was cysmethynil. Quantification was based on the ratio of peak areas of the daughter ion and the mother ion (M+H), normalized against the same ratio obtained for the internal standard. The solubility determinations were carried out in triplicates or more from two different stock solutions.

Determination of Permeability of Test Compounds

The Parallel Artificial Membrane Permeability Assay (PAMPA) was used to determine the effective permeabilities (P$_e$) of compounds 8-12 and 305. Briefly, determinations were carried out on MultiScreen-IP PAMPA assay (donor) plates (MAIPNTR10) and MultiScreen Receiver Plates (MATRNPS50) from Millipore Corporation (USA) with 1% lecithin (L-α-phosphatidylcholine from lyophilized powder of egg yolk, Sigma Aldrich, USA) in dodecane (ReagentPlus®, Sigma Aldrich, USA) as lipid barrier. 5 µL of 1% lecithin in dodecane was dispensed into the wells of the donor plates. Aliquots (300 uL) of test compound (120 uM of 6 and 50 µM of 8, both in 0.1×PBS with 1% DMSO) were dispensed into the donor wells and equal volumes of the buffer solution (0.1×PBS with 1% DMSO) were added to the corresponding acceptor wells. The donor and acceptor plates were assembled and the unit was gently agitated on a mini shaker at room temperature (25° C.) for 16 hours: After this time, aliquots (250 µL/well from donor and acceptor plates) were transferred to wells in a UV compatible plate (Costar-3635, Corning) for quantification at λmax of 262 nm for 8-12 on a microplate reader (Tecan Infinite™ M200). In the case of 305, 180 µL/well of the donor and acceptor plates were transfer to separate glass inserts in HPLC vials. 20 µL of the internal standard (diethyl-[5(4-methanesulfonyl-phenyl)-1-octyl-1H-indol-3yl methyl]-amine) solution (100 µM in acetonitrile) was added to each sample which were then measured by LCMS (Shimadzu LC 20 series HPLC and AB Sciex Instruments 3200 Q TRAP LC/MS/MS) and was based on the ratio of peak areas of the daughter ion and the mother ion (M+H), normalized against the same ratio obtained for the internal standard. The mobile phase was Milli-Q water (0.1% formic acid) and acetonitrile (0.1% formic acid), run on gradient. The column was Poroshell 120 EC-C18 (150×4.6 mm, 2.7 Å) and injections were made at a volume of 2 µL with flow rate of 0.6 mL/min. Calibration plots of test compounds were obtained under similar analytical conditions.

P$_e$ of three standard compounds were determined under similar conditions, namely caffeine, quinidine and verapamil. 500 uM stock solutions were prepared and dispensed to the donor wells as described earlier. Quantification was by uv at λmax of 272 nm (caffeine), 280 nm (verapamil) and 330 nm (quinidine). Calibration plots of reference compounds were determined under similar analytical conditions. The Pe of these compounds were in the sequence verapamil>quinidine>caffeine.

P$_e$ was obtained from Equation 1:

$$P_e = -2.303 \times \frac{V_A V_D}{(V_A + V_D) \times A \times (t)} \times \log\left\{1 - \frac{V_A + V_D}{V_D \times S} \times \frac{C_{A(t)}}{C_{D(o)}}\right\}$$

Where $V_A$ and $V_D$ are the volumes of acceptor (cm$^3$) and donor (cm$^3$) wells respectively, A is the area of the surface area of the membrane (0.24 cm$^2$), t is the permeation time (s); S is the fraction of sample remaining in the donor and acceptor wells after permeation time and is determined from Equation 2, $C_A$ and $C_D$ are the concentrations (µM) of test/reference compound in acceptor and donor wells respectively.

$$S = \left[\frac{V_A}{V_D} \times \frac{C_{A(t)}}{C_{D(o)}}\right] + \frac{C_{D(t)}}{C_{D(o)}} \qquad \text{Equation 2}$$

The P$_e$ of each compound was obtained from at least 3 separate experiments using no less than 2 different stock solutions. For each independent determination, triplicates (3 wells) were run for each compound.

Assessment of Aggregation Tendency by Dynamic Light Scattering (DLS)

Stock solutions (10 mM) of test compounds prepared in DMSO, diluted to 1 mM with DMSO and then serially diluted with potassium phosphate buffer (5 mM, pH 7.4, prefiltered before use) to give final concentrations of 1 µM and 10 µM. Final concentration of DMSO was 1% v/v. Measurements were carried out on the Malvern Instrument Zetasizer Nano ZS system equipped with a 4 mW He—Ne laser at 633 nm and detector angle of 90°. Three or more determinations of derived count rates (kilocounts per second, kcps) were obtained from each concentration of test compound, using two separately prepared stock solutions. Data collection was carried out using the software supplied with the instrument. Results are represented as mean±standard deviation. The positive control was benzyl benzoate (250 µM) which gave a count rate of 1180 kcps (±35). The vehicle (phosphate buffer, 1% DMSO) gave a reading of 14.9±0.4.

Determination of In Vitro Stability of Cismethynil, 8-12 and 305 in the Presence of Rat Liver Microsomes The test compound was incubated with pooled male rat liver microsomes in a mixture (total volume 500 uL) comprising the following: rat liver microsomes (0.3 mg microsome protein/mL), test compound (6 except cysmethynil which was evaluated at 3 µM) and phosphate buffer (0.1 M, pH 7.4, containing 1 mM EDTA). The mixture was preincubated for 5 min at 37° C. in a shaking water bath, after which the reaction was initiated by adding 50 pit of 10 mM NADPH (freshly prepared in phosphate buffer) to give a final concentration of 1 mM NADPH in the mixture. Aliquots of 50 µL were withdrawn immediately on addition of NADPH (time 0) and subsequently at 5, 15, 30 and 45 min. On removal of the sample, reaction was quenched by addition of chilled methanol (100 µL) which also contained the internal standard (diethyl-[5(4-methanesulfonyl-phenyl)-1-octyl-1H-indol-3yl methyl]-amine at 2 µM). The mixture was then centrifuged at 10,000×g to remove the protein and the content of the test compound in the supernatant was subsequently measured by LCMS.

For each test compound, the metabolic stability of a positive control, midazolam (5 µM) which is a known cytochrome P450 substrate, was concurrently determined to evaluate the adequacy of the experimental conditions. The stability of the test compound to microsomal degradation in the absence of NADPH was also monitored.

Analysis was carried out by LC-MS-MS on a 1200 HPLC instrument (Agilent Technologies, Palo Alto, Calif., USA) coupled to a Q Trap™ 3200 hybrid triple quadrupole linear ion trap mass spectrometer (Applied Biosystems/MDS Sciex, Concord, Ontario, Canada) for cysmethynil, or a Shimadzu UFLC system (Shimadzu Scientific Instruments, Columbia, Md.) coupled to a Q Trap™ 3200 hybrid triple quadrupole linear ion trap mass spectrometer (Applied Biosystems/MDS Sciex, Concord, Ontario, Canada) for the other compounds. Separations were made on a $C_{18}$ column (Luna 3u C18(2) 100A column (2.0×50 mm, i.d., 3 µM, Phenomenex, Aschaffenburg, Germany or Eclipse Plus C18 column, 4.6×150 mm, i.d., 3.5 µM Agilent Technologies, Palo Alto, Calif., USA) with a security guard cartridge (3.0×4 mm, Agilent Technologies, Palo Alto, Calif., USA). Mobile phase was 0.1% formic acid in acetonitrile-water as mobile phase. Flow rate was set at 0.2 or 0.6 mL/min and the column temperature was at 30° or 40° C. 2 or 5 µL full loop sample injection was used.

Data processing was performed with Analyst™ 1.4.2 software package (Applied Biosystems, MA., USA). The corresponding MRM transition of this candidate was selected and used for peak configuration in Analyst 1.4.2 for semi-quantitation. The peak areas of test compound at different time points were expressed as a % of the peak area of test compound at time=0 min. The resulting % of intact (or remaining) test compound (average of 3 measurements with SD) was plotted against incubation time drug (Figure xx). In vitro half life ($T_{1/2}$, min) was calculated from Equation 3 (Lu C, Li P, Gallegos R, Uttamsingh V, Xia C Q, Miwa G T, et al. Comparison of intrinsic clearance in liver microsomes and hepatocytes from rats and humans: evaluation of free fraction and uptake in hepatocytes. *Drug Metab Dispos* 2006; 34: 1600-5).

$$T_{1/2}=0.693/k(\min) \quad \text{Equation 3:}$$

Where k is the slope of the plot
Estimated in vitro clearance was determined from Equation 4:

$$CLint, \text{ in vitro}=V\times 0.693/T\tfrac{1}{2} \quad \text{Equation 4:}$$

where V (µL/mg)=Volume of incubation/amount of microsomal protein in the incubation (µL/mg)

Ames Test for Mutagenicity

The Ames Test for mutagenicity was carried out following the instructions listed in the *Salmonella* Mutagenicity CompleteTest Kit 31-100.2 from Molecular Toxicology Inc (Boone, N.C.).

Discussion

The purpose of the present investigation was to explore design strategies that would serve to enhance the drug-like and potency profiles of cysmethynil. To this end, the inventors have identified the inclusion of N-containing heterocycles and in particular the 2-aminopyridimidinyl ring, as a promising approach. This is evident from the outstanding activity and physicochemical profile of 8-12, which was modified from an early hit compound by substituting a m-tolyl with 2-aminopyrimidinyl. The presence of this entity resulted in remarkable improvements in solubility (pH 7.4) and PAMPA permeability which were achieved with concurrent gains in Icmt inhibitory and antiproliferative activities. Furthermore, 8-12 unlike its m-tolyl analogue, did not demonstrate detectable aggregation. The potential of the 2-aminopyrimidinyl moiety is further validated by compound 305 which has a cyclized amino side chain. Cyclization of the amino side chain is seen here to be a less promising design strategy. Nevertheless, compound 305 was significantly soluble, had good PAMPA permeability, low aggregation potential and good Icmt/antiproliferative activities. In terms of susceptibility to in vitro rat microsomal metabolism, the 2-aminopyridiminyl moiety in compounds 8-12 and 305 did not appear to have a major influence.

The 2-aminopyrimidinyl moiety is intrinsically hydrophilic with pronounced hydrogen (H) bonding capacities. These properties may account for its ability to enhance the drug-like profiles of cysmethynil which is a highly lipophilic compound.

Overall, the present study highlights the potential of the 2-aminopyridiminyl moiety as drug-like fragment which in the present context was successfully employed to identify potent Icmt inhibitors with good in vitro antiproliferative activities and desirable physiochemical profiles.

Further Investigations on the Antiproliferative Activity of Compound 8-12 [

Compound 8-12 {5-[3-(diethylamino)methyl-1-octyl-1H-indol-5-yl]pyrimidine-2-amine} was identified above as a promising analog in terms of antiproliferative activity and Icmt inhibition. Here, the antiproliferative activity of 8-12 was explored in detail, in order to address the following questions. First, it was of interest to determine if 8-12 would retain activity on a wider range of malignant cell types, and importantly to if it affected viability of non-malignant cells. Second, there was a need to understand how 8-12 arrested the proliferation of malignant cells and if the antiproliferative activity of 8-12 was complemented by induction of cell death. Third, tissue invasion is an acquired capability of cancer cells and the ability to halt cell migration is a desired attribute of an anti-cancer agent. It was of interest to determine if this property characterized 8-12.

To investigate these questions, the following experiments were carried out. The growth activities of 8-12 were determined on two additional malignant cells—human hepatocellular carcinoma HepG2 and human pancreatic MIA-PACA II cells. In total, 8-12 was evaluated on a panel of 4 malignant cells (prostate PC3, breast MDA MB 231 above). It was also evaluated on non-malignant human lung fibroblast cells IMR90 to assess if it acts selectively on malignant cells. To supplement the antiproliferative evaluation, a clonogenic assay was carried out to assess if a representative malignant cell (PC3) retained reproductive capacity after treatment with 8-12. As for the second question, an assessment on the cell cycle would be an appropriate starting point, particularly to determine if the key checkpoints (G1/S, G2/M) were disrupted by 8-12 in a concentration dependent manner. Cell death may be induced by different mechanisms-necrosis, apoptosis, autophagy and in this chapter, these options were explored for 8-12 on representative malignant cell lines. The effects on cell migration were determined by a "scratch" assay, which is a preliminary method for the analysis of this phenomenon.

Experimental Methods
Determination of Cell Viability

Human hepatocellular carcinoma HepG2 and human pancreatic cancer MIA PACA II cells were obtained from ATCC (Rockville, Md.). They were grown in DMEM (high glucose, Invitrogen) supplemented with 10% FBS, 50 μg/mL penicillin and 50 μg/mL streptomycin, 37° C., 5% $CO_2$ until they reached 80-90% confluency, after which they were subcultured. Passage numbers were kept within 7-14 passages for both cell types.

The growth inhibitory activity of 8-12 on IMR90 cells was assessed as follows. Human lung fibroblast IMR90 cells were purchased from ATCC (Rockville, Md.) and grown in Eagle's Minimal Essential Media (EMEM, Sigma Aldrich, Singapore) at 37° C., 5% $CO_2$. The media was supplemented with 10% fetal bovine serum (heat treated), 100 mg/L penicillin-G and 100 μg/mL streptomycin. Cells were subcultured at 80-90% confluency and used within 4-10 passages respectively. Seeding density was maintained at 4000 cells per well.

Colony Formation

A flask (75 $cm^3$) of PC3 cells in media (DMEM high glucose, 10% fetal bovine serum, 50 μg/mL penicillin, 50 μg/mL streptomycin) was grown to 80-90% confluency. The media was removed by pipetting and the cell layer washed with 1×PBS (5 mL). An aliquot of trypsin (1 mL, 0.25% trypsin-EDTA (1×)-phenol red, Invitrogen) was added to the plate, tapped gently for even distribution and incubated at 37° C., 5% $CO_2$ for 1 min. The plate was quickly viewed under the microscope to confirm that cells have rounded up. Media (10 mL) was then added and the cell suspension transferred to a falcon tube (15 mL). An aliquot (10 μl) was transferred to a hemocytometer for cell counting. The suspension was then diluted to give the desired seeding concentration of 1000 cells per well in a 6-well plate. After seeding, the plate was gently tapped to help cells spread out within the wells. Plates were then incubated for 2 h (37° C., 5% $CO_2$) for cell attachment to take place. The media was removed with a pipette, the cell layer in the well washed with PBS and replaced by a solution of the test compound in 2 mL of DMEM (containing 5% FBS, instead of 10% FBS). Test compounds were prepared in DMSO stock solutions. The final concentration of DMSO in the well was 0.05% v/v. Control plates were also prepared in which no test compound was added but with DMSO maintained at 0.05%. The plates were incubated (37° C., 5% $CO_2$) for 2 weeks. After this time, media was removed from the plates by pipetting, carefully rinsed with PBS, followed by addition of methanol-acetic acid (3:1) solution (1 mL per well) to fix the cells to the floor of the well. After 5 minutes at room temperature (25° C.), the solution was removed and crystal violet solution (0.5% v/v in methanol) was added to the plate for 15 min at 25° C. The plate was then carefully rinsed with tap water. Colonies of cells were visible blue dot/patches on the plate which were visible to the naked eye. Each test compound was investigated at 5 concentrations and on three separate occasions.

Cell Cycle Analysis by Flow Cytometry

PC3 cells were seeded at 100 000 cells/mL per well in 6-well plates with media DMEM (high glucose, 10% FBS, 50 μg/mL penicillin, 50 μg/mL streptomycin) and incubated (24 h, 37° C., 5% $CO_2$) to allow cell attachment after which they were treated with test compound (in DMEM, high glucose, 5% FBS, 50 μg/mL penicillin, 50 μg/mL streptomycin) for 48 h. Final volume of DMSO per well was 0.05% v/v. Control wells (without test compound) were similarly treated. After the specified time, supernatant in the well was collected; the cell pellet was trypsinized, combined with the supernatant and pelleted by centrifugation (150 g, 5 min). After rinsing the pellet twice with ice-cold 1×PBS, the cells were suspended in 0.3 mL PBS, to which was added dropwise and with gentle shaking, cold ethanol (0.7 mL) to give a final concentration of 70% ethanol. The cell sample was then kept at 4° C. overnight after which it was centrifuged (150 g, 5 min), the supernatant was removed, the pellet rinsed with cold PBS and re-suspended in a solution of 100 μg/mL propidium iodide (PI, Sigma Aldrich, Singapore) and 0.1 mg/mL ribonuclease A (Sigma Aldrich, Singapore) in PBS (500 μL). The suspension was kept in the dark for 1 h, 25° C. (room temperature) before being analyzed for distribution in the G1,S, G2/M phases on a FCS500 flow cytometer (Beckman Coulter, CA) using the FlowJo® software (http: http://www.flowjo.com/) Each test compound was evaluated at 4 concentrations with 2 repeats per concentration.

Determination of Apoptosis

The Annexing® V-FITC Apoptosis Detection Kit (BD Biosciences, Franklin Lakes, N.J.) was used PC3 cells were seeded at 65 000 cells per well in 6-well plates with DMEM (high glucose, supplemented with 10% FBS) as media. Plates were incubated (24 h, 37° C., 5% $CO_2$) for cells to attach and then treated with test compound (prepared in same media but with 5% FBS) for 48 h. Final volume of DMSO per well was 0.05% v/v. After the specified time, the supernatant in the well was collected, the cell pellet was trypsinized, combined with the supernatant and pelleted by centrifugation (150 g, 5 min). The pellet was rinsed twice with cold 1×PBS and suspended in the proprietary binding buffer (1×) to give a concentration of $10^6$ cells per mL. An aliquot (100 μL) of the suspension containing $10^5$ cells was transferred to the FACS tube (5 mL) to which was added Annexin® V-FITC solution (5 μL) and propidium iodide (PI) solution (5 μL). The solution was gently vortexed, incubated in the dark for 15 min at room temperature (25° C.), after which was added 400 μL of the binding buffer (1×). The sample was analyzed immediately or no later than 1 h, in which case it should be kept in ice and protected from light. Analysis was carried out on a FCS500 flow cytometer (Beckman Coulter, CA) using the FlowJo® software (http: http://www.flowjo.com/). Controls comprised untreated cells, cells exposed to Annexin® V-FITC only, and cells exposed to PI only. Each test compound was evaluated at 4 concentrations. Only 1 determination was made per concentration.

Western Blot Analysis

MDA MB231, PC3 and HepG2 cells were seeded at 65 000 cells/mL per well in E-well plates with DMEM (high glucose, supplemented with 10% FBS, 50 μg/mL penicillin, 50 μg/mL streptomycin) as media. Plates were incubated (24 h, 37° C., 5% $CO_2$) for cells to attach and then treated with test compound (prepared in same media but with 5% FBS) for 24 h or 48 h. Final volume of DMSO per well was kept at 0.05% v/v. After the specified time, the supernatant was removed from the well by pipetting, the cell pellet was trypsinized, and pelleted by centrifugation (150 g, 5 min) and stored in −20° C. Samples were thawed and cells lysed by adding RIPA (radioimmunoprecipitation assay lysis buffer, Thermo Scientific, Rockland, Ill.) (50 μL), kept in ice for 30 min and sonicated for 1 min in an ice bath. Samples were centrifuged (13 000 g, 5 min, 4° C.) to remove cell debris. The supernatant was stored as aliquots at −80° C. and used when required. At the time of use, samples were thawed and protein content determined using the BCA® Protein Assay reagent (Thermo Scientific, Rockland, Ill.). The volume of the lysate was adjusted with deionized water to normalize protein content to 10-20 μg per mL. To this was added Laemmli buffer (4×) and heated to 100° C. for 5 minutes to denature the protein. The samples were resolved by 12% SDS-PAGE gel electrophoresis at 100V for 90 min. The resolved proteins were transferred to polyvinylidene difluoride (PVDF) membranes (Bio-Rad, Singapore) using transfer buffer at 100V for 120 min. Membranes were then treated with 5% blocking buffer (5% non-fat milk and 0.1% Tween-20 in PBS) and probed with the specific antibody (GAPDH, LC3) by incubating the membranes in blocking buffer containing the antibody at 4° C. overnight. After washing the membranes in PBS containing 0.1% Tween 20 (PBST), the membranes were probed with secondary antibodies (horseradish peroxidase anti mouse IgG, Pierce, USA) in blocking buffer at room temperature for 1 h. They were then washed with PBST and developed using an enhanced chemiluminescence procedure (Amersham ECL Advanced Western Blotting Detection Kit, GE, Healthcare, UK). Immunoblots were viewed using the ImageQuant® RT-ECL imager (GE Healthcare) and the image captured with the ImageQuant® TL software. Antibodies were obtained from the following sources: GAPDH (Cell signaling technology, USA), LC3 (Abgent, USA). Test compound was evaluated at 3 concentrations with 2 repeats for each concentration.

Immunofluorescence

Cover slips were placed into the base of each well in a 24-well plate. PC3 cells were seeded at 10 000 cells/mL per well in media (DMEM Hi-glucose, 10% FBS, 50 μg/mL penicillin, 50 μg/mL streptomycin) and incubated for 24 h. After this time, cells were attached as a layer onto the exposed face of the cover slip. The media was carefully removed from the well without disrupting the cell layer on the cover slip. Test compound in DMEM (high glucose, 5% FBS) was added and incubated for 24 h or 48 h. DMSO concentration was kept at 0.05% per well, including control wells. At the end of the incubation period, media was removed, wells were washed thrice with PBS, followed by addition of chilled PBST (200 μL) per well for 10 minutes to permeabilize the cells. Cells were then fixed with 4% paraformaldehyde (300 μL), incubated for 15 minutes, and washed with cold PBS (3 times) to remove the fixing solution. To the cell layer fixed on the cover slip in the well was added 100 μL of anti-LC3 in PBST (1:1000). The plates were kept at 4° C. overnight after which each well was washed 3× with cold PBS. Rhodamine Red-X® secondary antibody (Jackson Immunoresearch Laboratories, West Grove, Pa.) was added, incubated (2 h, 25° C.) and removed by washing with PBS (3 times). The cover slips were carefully removed from the wells and mounted onto glass slides and sealed with nail polish. Visualization was carried out on an Olympus fluorescent microscope fitted with the appropriate excitation and emission filters.

In Vitro "Scratch" Assay.

PC3 cells were seeded at 100 000 cells per well in a 6-well plate in media (DMEM, high glucose, 10% FBS, 50 μg/mL penicillin, 50 μg/mL streptomycin) and incubated (37° C., 5% $CO_2$) for 36 hours until confluent. The cell monolayer was scraped in a straight line with a 1 mL pipette tip to create a "scratch" which was also marked at the bottom of the plate with a marker pen. The media was removed from the well which was then washed with PBS. Test compound in 2 mL DMEM (high glucose, 5% FBS) was added to each well (DMSO concentration of 0.05% v/v per well) and the plates were incubated at 37° C., 5% $CO_2$. Control wells with PC3 monolayers were similarly treated. Scratches of approximately the same size were made on control and treated wells. Photographs of the scratched surfaces in wells were taken with a microscope fitted with a camera at the start of incubation and after 24 h. Magnification was kept constant at 40× for all acquired images. These were further analyzed by downloading the images into a Powerpoint® file and measuring (on-screen) the distances between one side of the scratch and the other. For each "scratch", four or five distances were measured across the length of the scratch in the initial (0 h) image and these same distances were monitored after 24 h. Each compound was tested at 3 concentrations with 3 repeats made for each concentration.

Statistical Analysis

Data was analyzed for statistical significance by one-way ANOVA followed by Dunnett post-hoc test on IBM SPSS Version 19 (Chicago, Ill.). $p<0.05$ was taken as the criterion for significance.

Figure 9:
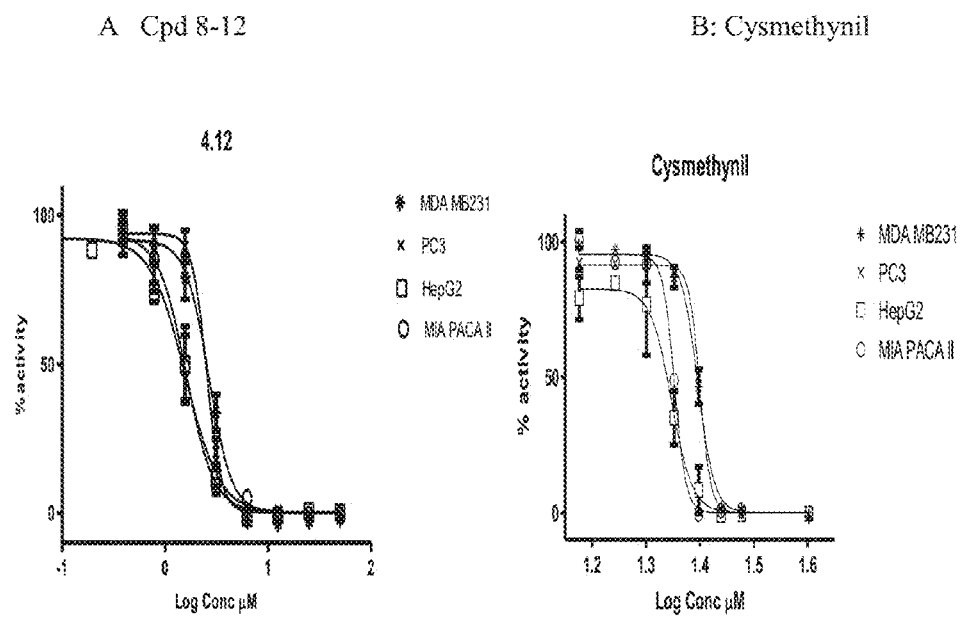
FIG. 9: Concentration versus % viability plots of (A) 8-12 and (B) cysmethynil on different malignant cell types

Results 8-12 Reduces Viability of HepG2 and MIA PACA II Cells 8-12 reduced the viability of HepG2 and MIA PACA II cells in a concentration dependent manner, in the same way as that observed on MDA-MB-231 and PC3 cells. Representative concentration response viability curves obtained for 8-12 on the 4 malignant cell lines are shown in FIG. 9. The close overlap of the curves reveal that 8-12 maintained the same level of potent activity on all the cell lines, as reflected in its $IC_{50}$ values which varied within a narrow range of 1.6-2.6 μM.

Cysmethynil and selected compounds (8-1, 8-10, 4-18, 8-25) also demonstrated concentration-dependence in their antiproliferative activities. Cysmethynil was equally potent on the tested malignant cells and this was also true for the other tested compounds. None of the latter compounds were more potent than 8-12 on the panel of malignant cells.

8-12 was also evaluated for its effects on the viability of the non-malignant human lung fibroblast IMR90 cells. Disappointingly, the non-malignant IMR90 cells were almost as susceptible as PC3 and MDA MB 231 cells to 8-12, but slightly less responsive (1.5×) when compared to HepG2 and MIA PACA II. The same was true for cysmethynil, 8-1 and 8-10, all of which failed to discriminate between the malignant cells and IMR90 to any significant degree.

TABLE 6

Cell viability IC50 values of 8-12, cysmethynil and other Series 4 compounds on a panel of malignant cell types and the non-malignant IMR90 cells

[Structure: 5-R₁-substituted indole with N-C₈H₁₇ on indole nitrogen and CH₂-N(C₂H₅)₂ at 3-position]

| Cpd No | R₁ | HepG2 | MIA Paca II | MDA MB 231[2] | PC3[2] | IMR90 |
|---|---|---|---|---|---|---|
| 8-1 | CH₃-phenyl (m-tolyl) | 6.57 | Not done | 7.90 (1.72) | 6.31 (0.20) | 5.26 (0.14) |
| 8-10 | H₃C-SO₂-phenyl-CH₃ | 3.44 (0.40) | Not done | 5.56 (0.58) | 4.74 (1.31) | 5.52 (0.11) |
| 8-12 | H₂N-pyrimidinyl-CH₃ | 1.65 (0.23) | 1.60 N = 2 | 2.63 (0.43) | 2.55 (0.46) | 2.65 (0.15) |
| 4-18 | H₃C-SO₂-NH-CH₂-phenyl-CH₃ | 6.97 (1.04) | Not done | 7.25 (0.61) | 10.39 (0.93) | Not done |
| 8-24 | H₃CHN-SO₂-phenyl-CH₃ | 4.76 (2.00) | Not done | 8.70 (2.94) | 6.48 (0.17) | Not done |
| Cysmethynil | | 21.78 (0.19) | 22.52 N = 2 | 27.35 (1.10) | 25.22 (0.80) | 29.2 (1.9) |

IC₅₀ (μM)[1]

[1]Mean (±SD) of at least 3 determinations or mean of 2 separate determinations.
[2]From earlier table.

8-12 Arrests the Cell Cycle of PC3 Cells at the G1 Phase

Inhibition of CaaX proteins is expected to impact cell cycle progression. The Icmt inhibitors cysmethynil, N-Ethyl-N-((1-(3-methylbut-2-enyl)-5-m-tolyl-1H-indol-3-yl)methyl)ethanamine and 8-1 were previously reported to disrupt the cell cycle of PC3 and MDA-MB-231 cells at the G1 phase. G1 arrest was observed after 24 h of incubation at concentrations of 25 μM (cysmethynil) and 4 μM (3-2, 4-1). These investigations were carried out by fluorescence activated cell sorter analysis (FACS) using flow cytometry. In a subsequent study, cysmethynil (25 μM) was shown to similarly arrest HepG2 cells at the G1 phase after 48 hours of incubation. When incubation was extended to 72 hours, a significant increase in the sub-G0 phase, indicative of substantial cell death, was observed.

Briefly, at the G1 phase, cells exhibit high levels of biosynthetic activity in preparation for DNA synthesis which occurs in the subsequent S phase. Cells rigorously monitor their cellular environment during this period and depending on the signals received, will proceed with the next phase of the cycle and proliferate, be forced out of the proliferative cycle into the quiescent G0 phase from which they may later reemerge, or permanently relinquish their proliferative potential by entering into a post-mitotic state, for instance by acquiring differentiation traits. Cancer cells normally acquire insensitivity to anti-growth signals arising from the G1 phase. Most if not all of the antigrowth signals involve the retinoblastoma protein (pRb) which when hypophosphorylated, blocks proliferation by sequestering and altering the function of E2F transcription factors that control the genes required for G1→S progression. In cancer cells, pRb is hyperphosphorylated which causes it to dissociate from the E2F/Rb complex thereby activating E2F and promoting the transcription of genes involved in proliferation. Consistent with the findings of G1 arrest in PC3 and HepG2 cells, cysmethynil reduced cyclin D1 and phosphorylated pRb levels.

A range of concentrations encompassing the $IC_{50}$ of 8-12 were incubated with PC3 cells for 48 h and then analyzed by FACS for the distribution of DNA at the G1, S and G2 phase. For comparison, cysmethynil was investigated under similar conditions but at higher concentrations in line with its $IC_{50}$. The results are tabulated in Table 7

TABLE 7

% Cells in G1 and G2 phases of PC3 cells treated with 8-12 and cysmethynil (48 h incubation)

|  | % Cells in G1 phase[1] | % Cells in G2 phase[1] |
|---|---|---|
| Control[2] | 47.17 (1.94, 6) | 27.94 (5.26, 5) |
| 0.8 µM 8-12 | 52.92 (2) | 24.22 (2) |
| 1.0 µM 8-12 | 59.98 (2)[3] | 26.99 (2.77, 3) |
| 1.5 µM 8-12 | 53.84 (2.78, 3) | 22.16 (8.66, 3) |
| 2.0 µM 8-12 | 66.45 (2)[3] | 11.20 (2)[3] |
| 12.5 µM Cysmethynil | 53.0 (2) | 27.87 (2) |
| 15.0 µM Cysmethynil | 51.63 (2) | 37.21 (2) |
| 17.5 µM Cysmethynil | 51.83 (2) | 26.85 (12.28, 3) |
| 20.0 µM Cysmethynil | 54.85 (2) | 32.07 (2) |

[1]Mean values (SD where applicable, number of determinations).
No SD is reported for 2 determinations.
[2]Cells treated with media (0.05% v/v DMSO) in the absence of test compound.
[3]Significantly different (p < 0.05) from control G1 or G2 phase (1-way ANOVA, Dunnett 2-sided post hoc).

It can be seen from Table 7 that compared to the control untreated cells, 8-12 increased cells in the G1 phase while decreasing cells in G2 phase, changes which were indicative of a G1 arrest. These changes were significant for the highest concentration of 8-12 tested (2.0 µM). Cysmethynil had previously been reported to cause G1 arrest in PC3 cells but this was not readily observed here. Although an increase in the G1 population was evident in cysmethynil treated cells, there was no corresponding decrease in G2 phase and the changes in G1/G2 cell populations were not statistically significant.

8-12 Inhibits Colony Formation of PC3 Cells

The ability of cells to propagate and form colonies (defined as a cluster of at least 50 cells) is an indication of its reproductive capability. When cell death occurs, cells lose their reproductive integrity and ability to proliferate indefinitely. The clonogenic (or colony formation) assay is widely used to detect cells that retain the capacity to reproduce after treatments that cause reproductive death such as ionizing radiation or cytotoxic agents. Essentially, the assay tests the ability of individual cells in a population to undergo "unlimited" division.

Figure 10:
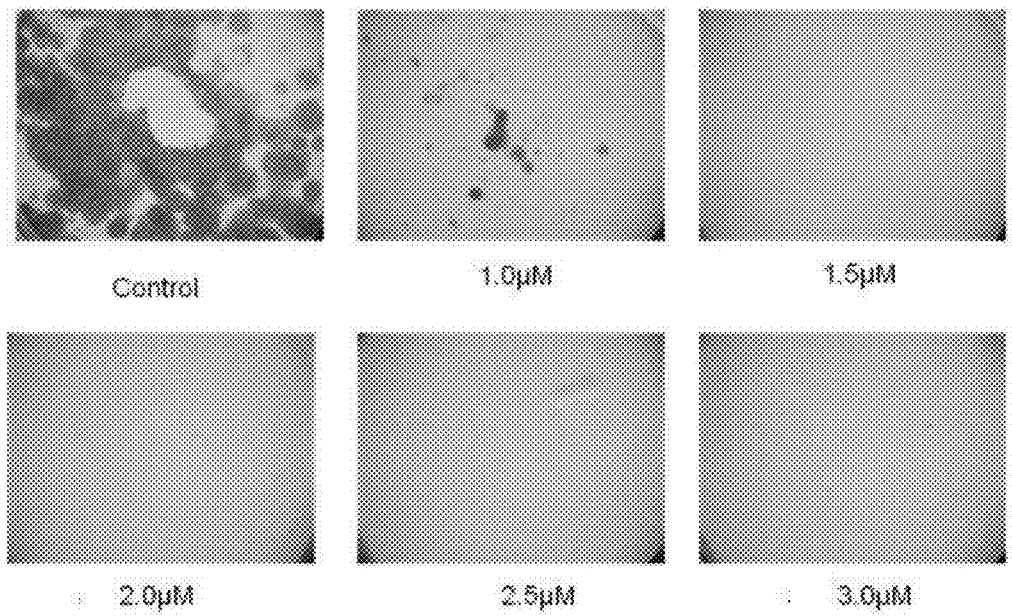
FIG. 10: Photographic images of PC3 cells treated with different concentrations of 8-12 and cysmethynil.
Figure 10:
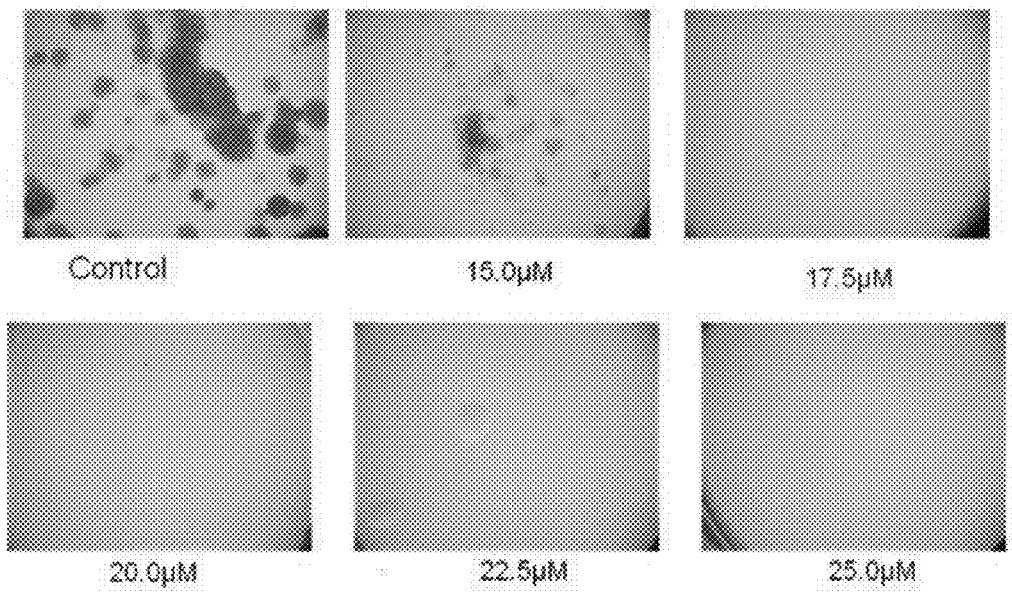

The effects of 8-12 and cysmethynil on colony formation of PC3 cells were investigated over a range of concentrations, namely 1-3 µM for 8-12 and 15-25 µM for cysmethynil. The results are shown in FIG. 10 In the case of 8-12, colony formation was evident only at the lowest concentration of 1 µM and not at higher concentrations (1.5 to 3 µM). Colony formation was observed with 15 µM cysmethynil but not at higher concentrations (17.5 to 25 µM). These were encouraging results as they demonstrated the ability of both compounds to abrogate the reproductive capabilities of PC3 cells at concentrations that were close to their $IC_{50}$ values. In the case of 8-12, colony formation was clearly inhibited at 1 µM.

8-12 does not Induce Apoptotic Cell Death of PC3 Cells

Since 8-12 caused a replication block at the G1 phase of the cell cycle of PC3 cells and limited the reproductive capability of this cell line in the clonogenic assay, the next step was to determine if it causes programmed cell death since stalling the proliferation of cancer cells will lead to a "cellular crisis" and the initiation of apoptosis. For therapeutic efficacy, diminished proliferation would be complemented by an increase in the rate of attrition of cells, namely induction of cell death. Cysmethynil has been reported to trigger apoptosis in HepG2 cells but not in PC3 cells. Cell death by autophagy was however observed in both cell types. The contrasting apoptotic response of PC3 and HepG2 was attributed to differences in their cellular genetic or epigenetic background. 8-12 was investigated for its effects on apoptotic cell death in PC3 cells using a commercial kit based on dual staining by Annexin V and propidium iodide (PI). Briefly, the method is based on the loss of membrane asymmetry in cells undergoing early apoptosis. As a result, phosphatidylserine molecules normally located in the inner surface of the membrane are translocated to the outer membrane leaflet. The exposed phosphatidylserine residues interact strongly and specifically with Annexin V in the presence of calcium. By conjugating Annexin V with a fluorescent tag (fluorescein isothiocyanate, FITC), the binding of Annexin V to the membrane surface can be monitored. The kit includes propidium iodide (PI) which binds to cellular DNA of necrotic cells. In these cells, the cellular membranes are completely compromised and thus permeable to PI. The combination of Annexin V-FITC and PI allows differentiation of cells into 3 phases: normal cells (Annexin V−, PI−), early apoptosis (Annexin V+, PI−), and late apoptosis/necrosis (Annexin V+, PI+). These phases are observed in the lower left quadrant, lower right quadrant, and upper left and right quadrants respectively in the FACS diagram of cells double stained with Annexin V and PI.

Apoptosis was investigated by double staining of PC3 cells with Annexin V and PI at different concentrations of 8-12 and cysmethynil after 48 h. Only one independent determination was carried out for both compounds and thus the results should be regarded as preliminary. Nonetheless, cysmethynil was not found to induce apoptosis, in keeping with earlier findings on PC3 cells. Induction of apoptosis was also not observed for 8-12 (Table 8). Over the 3-fold concentration range of 8-12 investigated, the proportion of normal cells showed limited variation from control untreated cells, the proportion of apoptotic cells showed small increases and % necrotic cells remained largely unchanged from control (Table 8).

TABLE 8

Distribution of normal, apoptotic and necrotic PC3 cells treated with 8-12 and cysmethynil after an incubation period of 48 h.

|  | % Normal[1] | % Apoptotic[1] | % Necrotic[1] |
|---|---|---|---|
| Control[2] | 90.1 | 0.361 | 9.56 |
| 8-12 |  |  |  |
| 0.4 µM | 93.6 | 1.45 | 4.95 |
| 0.8 µM | 91.8 | 1.31 | 6.85 |
| 1.0 µM | 90.4 | 0.71 | 8.84 |
| 1.2 µM | 91.6 | 0.93 | 7.43 |
| Cysmethynil |  |  |  |
| 12.5 µM | 92.1 | 0.92 | 6.94 |
| 15.0 µM | 90.6 | 1.14 | 8.28 |
| 17.5 µM | 89.7 | 1.96 | 8.33 |

TABLE 8-continued

Distribution of normal, apoptotic and necrotic PC3 cells treated with 8-12 and cysmethynil after an incubation period of 48 h.

|  | % Normal[1] | % Apoptotic[1] | % Necrotic[1] |
|---|---|---|---|
| 20.0 μM | 90.7 | 1.23 | 8.06 |
| 22.5 μM | 89.6 | 1.21 | 91.4 |

[1]Determined from one analysis only
[2]Cells treated with media (0.05% v/v DMSO) in the absence of test compound Effect of 8-12 on PC3 Autophagic Cell Death Autophagy involves the degradation and recycling of proteins and intracellular components in response to nutrient deficiency in cells. There is still considerable discussion on the role of autophagy in cancer and whether the therapeutic response of anticancer drugs should be to induce or inhibit autophagy. The general consensus is that the role of autophagy in tumorigenesis is context dependent. In the early phases of tumor growth, autophagy is suppressed in order to promote tumor growth. As the tumor matures, autophagy may be induced to supply nutrients to proliferating cells which may be experiencing cellular stresses like hypoxia and nutrient deprivation. Autophagy protects some cancer cells against anticancer therapy by blocking apoptotic pathways ("protective autophagy") in which case drugs that inhibit autophagy would be beneficial. On the other hand, drugs that induce autophagy would be desirable in tumors with fundamental defects in the apoptotic machinery.

Investigations with cysmethynil have shown that it induced autophagic cell death in PC3 and HepG2 cells. It was further demonstrated that cysmethynil induced apoptosis in HepG2 cells as well and that both autophagic and apoptotic cell death in HepG2 were evoked through the specific inhibition of Icmt. Moreover the robust autophagic response induced by cysmethynil led to apoptotic cell death, indicating that autophagy did not merely serve in a pro-survival or cytoprotective capacity.

The above work has shown several similarities between 8-12 and cysmethynil with respect to their effects on the cell cycle (G1 arrest) and absence of apoptosis in PC3 cells. It was of interest to determine if these similarities would extend to the induction of autophagy in PC3 cells. Earlier, 3-2 and 4-1 were shown to cause autophagic cell death in PC3 and MDA MB 231 cells over a range of concentrations at one time point (48 h). In view of their structural resemblance to 8-12, the same outcome was anticipated for 8-12. The effects of 8-12 on autophagy was therefore investigated in greater detail. First, the autophagic biomarker LC3II was monitored on three cell lines (PC3, MDA MB 231 and HepG2) at different concentrations of 8-12 and at different time points (24 h, 48 h). Second, autophagy was investigated by cell-based immunofluorescence analysis of LC3 aggregation in 8-12 treated PC3 cells after 48 h of incubation.

Briefly, autophagy begins with the isolation of double membrane-bound structures inside an intact cell. As these structures elongate and mature, they recruit microtubule-associated protein 1 light chain 3 (LC3) on their surfaces. The elongated membranes sequester cytoplasmic proteins and organelles (mitochondria, Golgi apparatus) and form autophagosomes. These subsequently fuse with lysosomes to become autolysosomes which carryout the task of degrading the sequestered contents and making them available for recycling. One assay for autophagic cells is to detect the presence of membrane bound LC3 on autophagosomes. Before attaching to the pre-autophagosomal structures, LC3 is ubiquitinated to give LC3-1 which resides in the cytosol. When autophagy is induced, some LC3-I is conjugated to phosphatidylethanolamine to give LC3-II, which associates tightly with the autophagosomal membrane. Hence, immunoblotting of LC3 results in two bands, LC3-I and LC3-II. On SDS-PAGE, LC3-I migrates faster than LC3-II. Increased production of LC3-II and its translocation to the autophagosome are indicators of autophagy induction.

Figure 11:
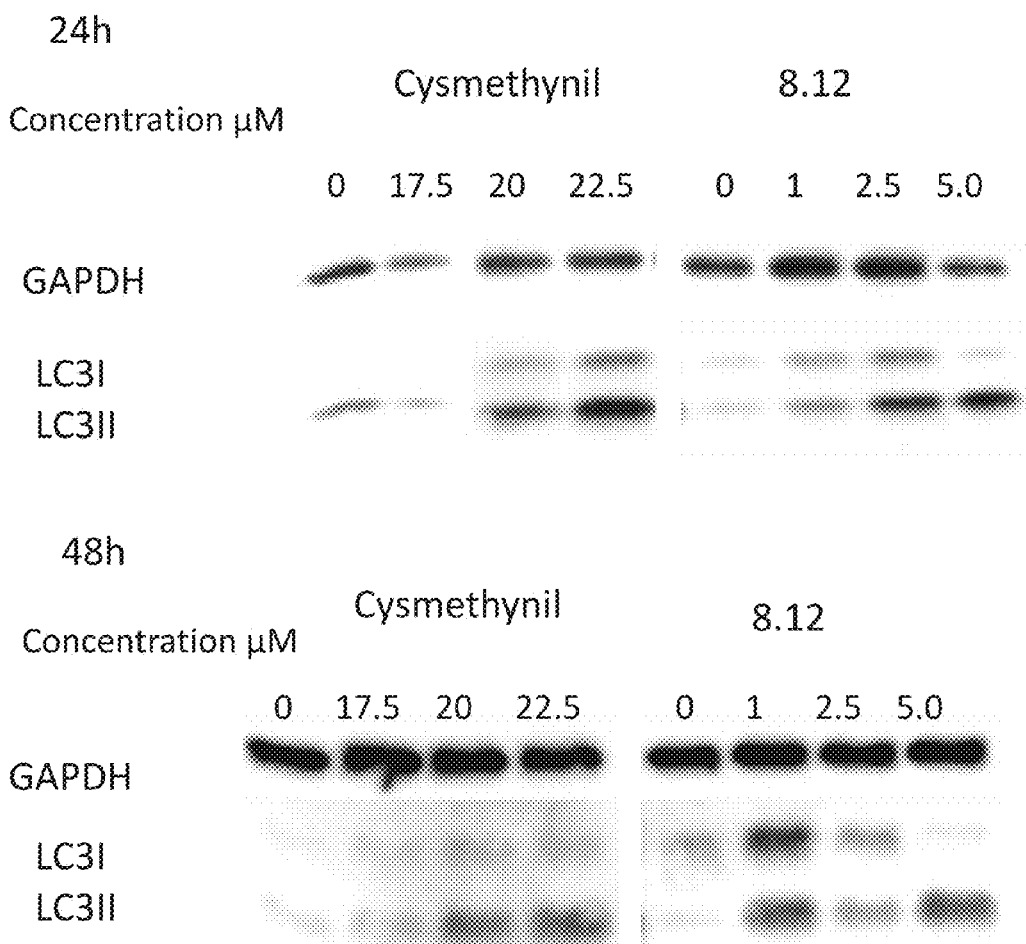
FIG. 11: Representative immunoblots of LC3-I and LC3-II from 8-12 treated cells (PC3, MDA MB 231, HepG2) at 24 h and 48 h time points. 8-12 was investigated at 1, 2.5 and 5 µM on (A) MDA MB 231 and (B) PC3 cells. On HepG2 cells (C), it was investigated at lower concentrations of 0.2 and 0.5 µM. Also included are plots obtained with cysmethynil at various concentrations, and GAPDH (glyceraldehyde-3-phosphate dehydrogenase) which acts as the house keeping protein Immunoblots were obtained from 2 independent repeats.
Figure 11:
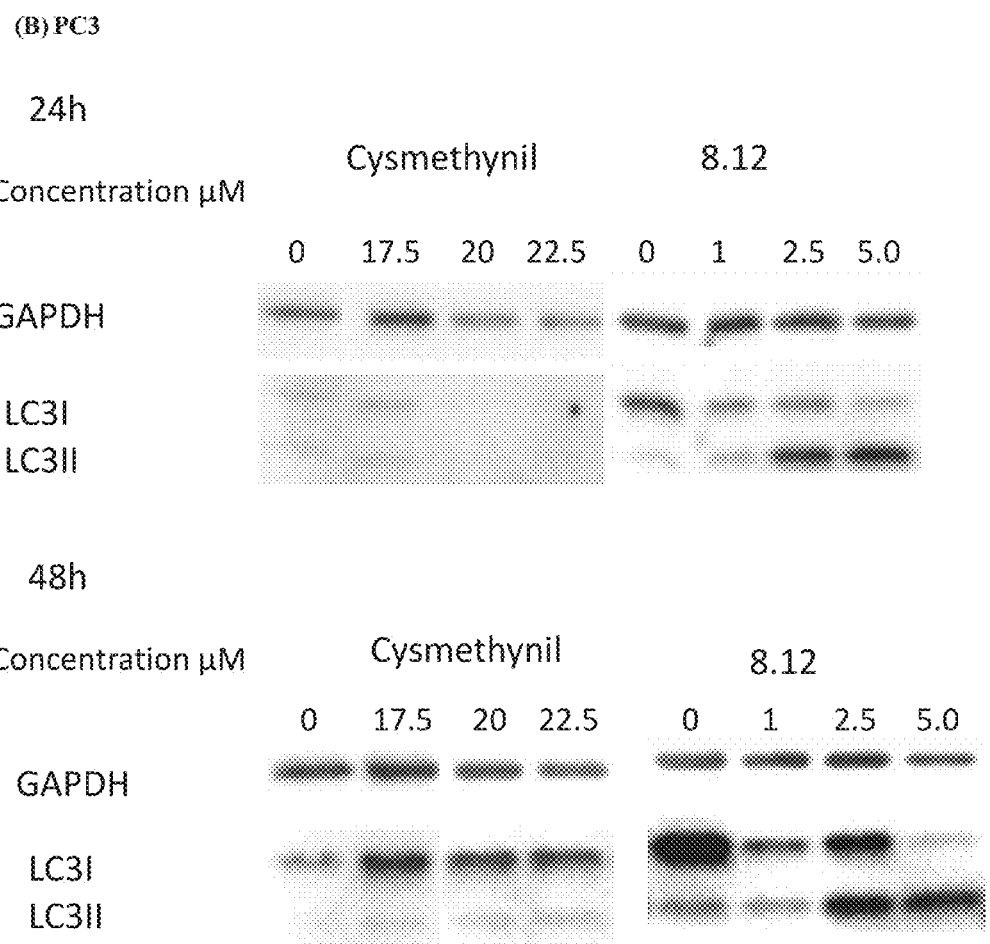
Figure 11:
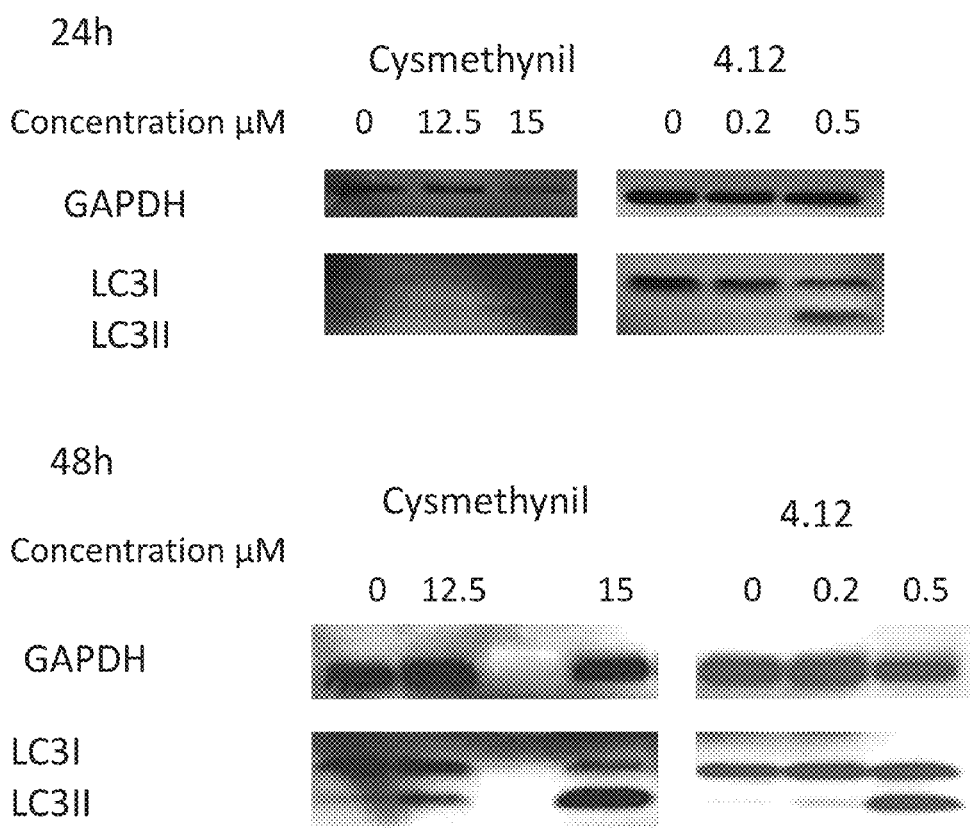

8-12 increased the content of LC3-II of MDA MB 231 and PC3 cells at 1, 2.5 and 5 μM at both time points (24 h and 48 h) (FIG. 11). As the intensities of these blots were not analyzed by densitometry, it was not possible to comment on concentration or time dependent effects. Visual inspection indicated that less LC3II accumulated at the lower concentration of 1 μM compared to the higher concentrations at both time points. The intense LC3II band observed at 1 μM 8-12 in treated MDA MB 231 cells after 48 h may be an aberration because a less intense band was observed at 2.5 μM on the same blot. LC3-II bands were detected in HepG2 cells treated only with 0.5 μM but not 0.25 μM 8-12. These bands were observed at both time points.

Previously, cysmethynil was demonstrated to increase LC3II content in PC3 and MDA MB 231 cells at 25 μM after 48 h of incubation whereas limited LC3 II was observed at 10 μM. FIG. 11 shows that LC3-II accumulation was evident in MDA MB 231 cells treated with cysmethynil at 20 and 22.5 μM, but not at 17.5 μM for both time points. These results were in keeping with those reported earlier. On the hand, negligible LC3II were observed from cysmethynil treated PC3 cells. HepG2 cells were treated with lower concentrations (12.5, 15 μM) of cysmethynil and LC3II accumulation was evident after 48 hours but not 24 h.

Immunofluorescence Assay

Figure 12:
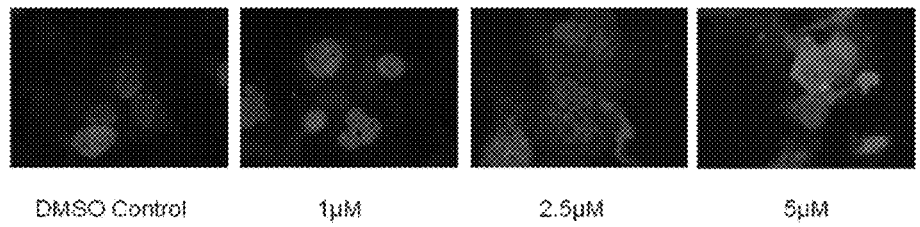
FIG. 12: Analysis of LC3 aggregation in (A) 8-12 and (B) cysmethynil treated PC3 cells (48 h). Fluorescent microscopy analyses of PC3 cells labeled with DAPI (blue) and rhodamine red secondary antibodies against LC3 (red) are shown.
Figure 12:
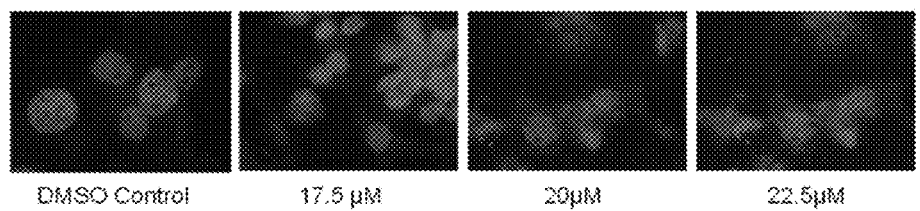

The induction of autophagy by 8-12 was further investigated by using cell-based immunofluorescent analysis to detect autophagosomes. PC3 cells were stained with fluorescence tags for in vitro cell imaging. The cell nucleus was stained blue by DAPI while LC3 protein was stained red by anti-LC3 and rhodamine-red tagged secondary antibodies. FIG. 12 shows that in control untreated cells, the blue fluorescence of the nuclei predominated. When cells were treated with 8-12, punctate LC3-positive (red) vacuoles were observed at 2.5 and 5 μM. Similar observations were evident for 20 and 22.5 μM cysmethynil.

8-12 Inhibits Cell Migration in the In Vitro Scratch Assay

The in vitro scratch assay is a simple and inexpensive method to study cell migration in vitro. It involves creating an artificial gap (scratch or wound) on a confluent cell monolayer and determining if a particular "treatment" (for example, presence of a test compound, varying media components) would affect the natural tendency of the cells at the edge of the scratch to migrate inwards and close the gap. Images are taken at the start of the experiment and at specific time points thereafter to assess the rate at which the cells migrate to effect closure. The method mimics to some extent the migration of cells in vivo but it is not meant to replace other well established methods for chemotaxis like the Boyden chamber or microfluidics-based systems, as no chemical gradient is established in the scratch assay.

Figure 13:
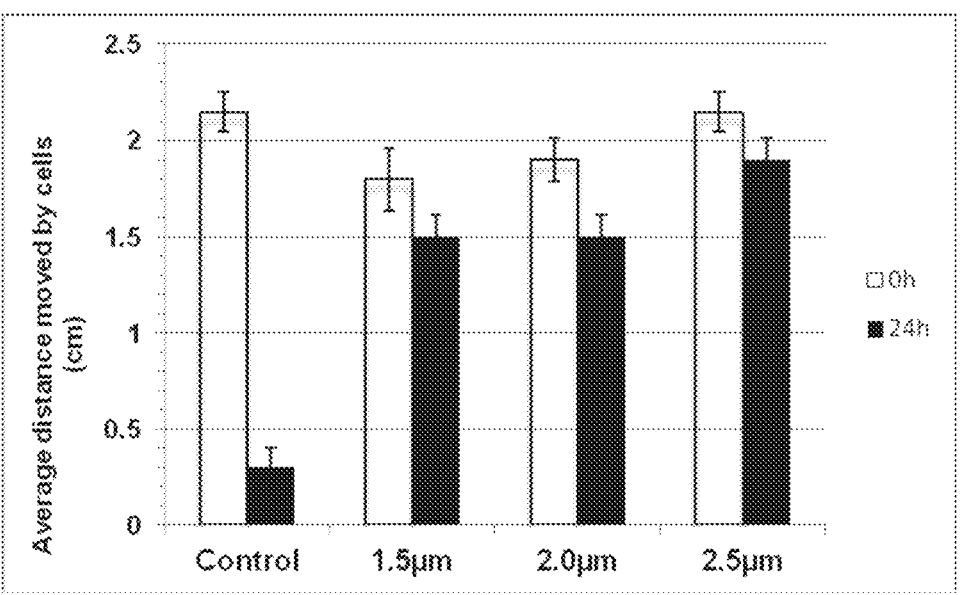
FIG. 13: Average distances between edges of scratches (±SD, n=3) in control wells and wells containing different concentrations of 8-12. Measurements were made at 0 h and 24 h after scratch was created.

The scratch assay was carried out on PC3 cells in the presence of 1.5, 2.0 and 2.5 μM 8-12, with images captured at the start of the experiment (0 h) when the scratch was created and 24 h later. Four distances were marked out across the gap initially on each plate (0 h) and these same distances were measured after 24 h. Visually, the gap was breached in the control (untreated) well after 24 h. In the case of wells treated with 8-12, the gap remained "open" at 2 and 2.5 μM but closed to some extent at a lower concentration of 1.5 μM. The measured distances between the gaps in treated and untreated cells after 24 h are depicted in FIG. 13.

The experiments were concurrently run with cysmethynil at 17.5, 20 and 22.5 μM. As seen from FIG. 13, the gap closed to some degree in the presence of 17.5 and 20 μM cysmethynil after 24 h, but remained open in cells treated with 22.5 μM cysmethynil. Thus, these experiments highlighted the potential of 8-12 and cysmethynil to inhibit cell migration at concentrations that correspond closely to the $IC_{50}$ values.

Discussion

Several important observations have emerged from the investigations described in this chapter. Foremost was the observation that 8-12 retained almost the same level of antiproliferative activity across a panel of diverse malignant cell lines. This was evident from the narrow range of $IC_{50}$ values (1.6 to 2.6 μM) derived from the different cell lines. The cells in the panel have different Ras status—PC3 cells have wild type Ras, MDA-MB-231 cells and MIA-PACA-II cells harbor mutated K-Ras, and HepG2 cells have high levels of mutated N-Ras, but these differences did not appear to have any overt influence on the antiproliferative activity of 8-12. Unfortunately, 8-12 was equally active in curtailing the proliferation of the non-malignant IMR90 cells, with no more than a 1.6 fold difference between the $IC_{50}$ values of IMR90 and MIA Paca II cells which was more susceptible to 8-12. Cysmethynil was equally non-selective in its antiproliferative activity although it was reportedly well-tolerated when administered to healthy animals.

The antiproliferative activity of 8-12 was traced to its ability to arrest the cell cycle at the G1 phase. In PC3 cells incubated with 2 μM 8-12 for 48 hours, significant changes were observed in the proportion of cells in G1 (increased) and G2 (decreased) compared to control untreated cells. G1 arrest is normally associated with changes in specific molecular marker proteins such as cyclin D1, p27 and phosphor-Rb.

8-12 was observed to arrest the colony forming capabilities of PC3 cells. The implication was that 8-12 not only arrested proliferation of these cells but also effectively curtailed their reproductive capability over time. In other words, PC3 cells were essentially killed by the compound. Cell death may be evoked by several mechanisms and in the case of 8-12, autophagic-induced cell death was found to play a prominent role. 8-12 increased the levels of the autophagosomal marker LC3-II in 3 malignant cell lines (PC3, MDA MB 231, HepG2). It also induced aggregation of LC3 protein in vesicular structures characteristic of autophagosomes. By contrast, preliminary assessment by dual staining with Annexin-V and PI showed limited apoptotic cell death in 8-12 treated PC3 cells.

Another pertinent observation related to the ability of 8-12 to promote cell migration as seen from the in vitro scratch assay. Although not directly linked to cell viability and proliferation, several processes related to cell migration like angiogenesis are hallmarks of carcinogenesis.

The results described above have provided evidence that 8-12 affected several processes that are critical in carcinogenesis, namely antiproliferation, disruption of cell cycle, induction of autophagy and cell migration. In spite of the diversity of these phenomena, the effects of 8-12 were observed over a narrow and recurring concentration range (1-5 μM). Compared to cysmethynil which also affected these processes in a qualitatively similar manner, 8-12 was clearly more potent by at least 10 folds magnitude.

Summary 8-12 was found to retain the same level of antiproliferative activity on a panel of diverse malignant cell types of different Ras status The antiproliferative activity of 8-12 on PC3 cells stemmed from G1 arrest. 8-12 also curtailed the reproductive integrity of PC3 cells, which was indicative of cell death. Investigations revealed that 8-12 induced autophagic cell death in several malignant cell types. There was less convincing evidence that it induced apoptosis. 8-12 inhibited in vitro cell migration and should be investigated for its effects on angiogenesis. 8-12 and cysmethynil shared many similarities in their activity profile but the effects of 8-12 were observed at a 5 to 10-fold lower concentration.

In Vivo Evaluation of 8-12 in Mice Bearing Xenografts Induced with Human Heptocellular Carcinoma HepG2 Cells Introduction This work describes investigations aimed at demonstrating the in vivo efficacy of 8-12 on xenografts induced by human heptocellular carcinoma HepG2 cells in immunocompromised mice. Before this evaluation could be carried out, two experiments on 8-12 were required. The first involved determining the maximal tolerated dose (MTD) of 8-12 in mice in order to establish the dose range to be administered in the xenograft experiments. Once proposed concentrations of 8-12 were identified, the next step was to confirm that mice receiving these doses would achieve concentrations in plasma that were comparable to the in vitro $IC_{50}$ of 8-12. In this way, appropriate doses of 8-12 could be delivered to the xenograft bearing animals for in vivo evaluation. An attempt to identify the possible metabolites of 8-12 in rat was also described herein.

Experimental Methods

Determination of Maximal Tolerated Dose (MTD)

Approval for the experimental protocol was obtained from the SingHealth Institutional Animal Care and Use Committee (Application number #2011/SHS/688). Experiments were carried out on female Balb/c mice (6-8 weeks old, 20-22 g) obtained from the Biological Resource Centre, Agency for Science, Technology and Research, Singapore. Animals were kept under controlled environmental conditions (19-26° C., relative humidity <70%, 12 h dark-light cycle) at the animal holding facility at Duke NUS medical school vivarium. Animals were given free access to water and standard feed. They were randomly assigned to 10 groups with 2 animals per group. Five groups were assigned for the determination of MTD of 8-12 and the remaining groups for cysmethynil. 8-12 was investigated at the following doses: 10, 20, 50 and 100 mg/kg. In the case of cysmethynil, doses were 20, 50, 100 and 200 mg/kg. The test compound was administered intraperitoneally using a 23G gauge needle to the animal in a volume of vehicle that was tagged to the body weight, namely 0.2 mL for 20 g animal and so on. The vehicle was formulated from ethanol, PEG 400 (Sigma Aldrich) and 5% dextrose (Sigma Aldrich) in the ratio 1:6:3. The test compound was first dissolved in ethanol, PEG400 was added and the solution was vortexed, followed by 5% dextrose and further vortexing. The solutions were freshly prepared before administration. For the determination of MTD, one group of 2 animals received the vehicle without test compound. Another group of 2 animals received the lowest dose of test compound by IP injection and were observed for 45 min. If they did not show signs of toxicity (vomiting, vocalization, hunched posture, shivering, decreased activity, immobility or moribund state), another group of 2 animals were given the next higher dose and the process was repeated until all the doses were tested. Animals in each group were observed for 24 hours thereafter.

Pharmacokinetic Study

Experiments were carried out on female Balb/c mice (6-8 weeks old, 20-22 g) obtained from the Biological Resource Centre, Agency for Science, Technology and Research, Singapore and maintained under similar conditions as described in 5.2.1. 8-12 was tested at two doses of 10 mg/kg and 25 mg/kg which were administered intraperitoneally (IP) to the mice, and blood was withdrawn at the following time points thereafter: 5 min, 15 min, 45 min, 1.5 h, 3 h, 8 h, 24 h and 48 h. Cysmethynil was tested at 20 mg/kg and 100 mg/kg in a similar manner and blood was withdrawn at the same time points.

12 mice were used for each dose. They were divided into 4 groups of 3 mice. All the mice received the test compound prepared in the vehicle described in 5.2.1. The volume administered was tagged to the animal's weight (for example, 0.2 mL for 20 g and so on). Collection of blood was staggered as follows: blood was withdrawn at 5 min and 3 h for the 1 St group of mice, 15 min and 8 h for the $2^{nd}$ group, 45 min and 24 h for the $3^{rd}$ group, 1.5 h and 48 h for the $4^{th}$ group. For the $1^{st}$ time point, blood was drawn from the sub-mandibular vein using a 21 G gauge needle. For the final time point, the animal was anaesthesized with an anesthetic mixture comprising ketamine (0.1 mL, 100 mg/kg), diazepam (0.1 mL, 5 mg/kg) in saline (0.8 mL). Each mouse was given 0.2 mL of the mixture (IP) and blood was withdrawn by cardiac puncture. The blood was collected in EDTA-coated tubes, centrifuged at 15800 g for 10 min at 4° C. and stored at −20° C. until analyzed. Naive blood samples were also collected from 4 untreated animals (submandibular route) to obtain the calibration curves required for LCMS quantification.

Samples for the calibration curves were obtained as follows: To a microcentrifuge tube was added the naïve plasma sample (45 μL), internal standard (20 μL) and test compound (5 μL). The internal standard was cysmethynil (50 μg/mL) for 8-12, and 8-12 (50 μg/mL) for cysmethynil. The test compound was added over a range of concentrations which were 2 μg/mL to 200 μg/mL for 8-12, and 2 μg/mL to 100 μg/mL for cysmethynil. The contents of the tubes were mixed well by shaking on a plate shaker for 5 min, after which ice cold methanol (150 μL) was added, shaking continued for another 15 min and then centrifuged (15800 g, 4° C., 15 min). The supernatant was transferred to an autosampler vial and an aliquot (10 μL) was injected into an LC/MS/MS instrument for analysis. In order to assess variations due to instrument fluctuations, calibration was repeated twice during the period of analysis. In the case of samples from treated animals, the procedure was the same except that 50 μL of plasma was added to the micro centrifuge tube and the test compound (5 μL) was omitted.

The instrument used for analysis was a Shimadzu UFLC system (Shimadzu Scientific Instruments, Columbia, Md.), with the Waters X-Terra® $C_{18}$ column (4.6×50 mm, 5 μM) maintained at an oven temperature of 30° C. and coupled to a QTRAP 3200 triple quadruple mass spectrometer (Applied Biosystems, Foster City, Calif.). Instrument control and data acquisition were performed using Applied Biosystems software Analyst 1.4.2. The mobile phase comprised (A) 10 mM ammonium formate in 0.1% formic acid and (B) acetonitrile, run on gradient mode. Flow rate was 0.6 ml/min, and a 20 μl injection loop was used. The settings on the LC/MS/MS for quantification are listed as follows:

| Cpd | Precursor Ion Mass (amu) | Product Ion Mass (amu) | Dwell Time (msec) | Declustering Potential (V) | Entrance Potential (V) | Collision Cell Entrance Potential (V) | Collision Energy (eV) | Collision Cell Exit Potential (V) |
|---|---|---|---|---|---|---|---|---|
| Cysmethynil | 377.8 [M + H] | 333.3 | 200 | 35.00 | 7.60 | 16.80 | 13.00 | 5.00 |
| 8-12 | 408.3 [M + H] | 335.2 | 200 | 62.00 | 9.00 | 16.00 | 53.00 | 3.00 |

Plasma concentrations from three mice were obtained at each time point and the mean value was plotted against time to give a plasma concentration versus time plot for each dosing regimen. Pharmacokinetic parameters were calculated by WinNonlin® (Standard Version 5.0.1, Pharsight, Sunnyvale, Calif.) using non-compartmentalized analysis for PO dosing.

In Vitro Metabolite Structure Identification

The test compound was incubated with rat liver microsomes for 45 minutes, after which aliquots were analyzed by LC/MS/MS for the presence of metabolites. The test compound was incubated with pooled rat liver microsomes (BD Gentest Corp, Woburn, Mass.) in a mixture (final volume 500 μL) comprising the following: rat liver microsomes (7.5 μL of 20 mg microsomal protein to give final concentration of 0.3 mg microsome protein/mL), test compound (2.5 μL of 1 mM test compound in acetonitrile to give final concentration of 10 μM) and phosphate buffer (440 μL of 0.1 M, pH 7.4, containing 1 mM EDTA). The mixture was preincubated for 5 min at 37° C. in a shaking water bath, after which-reaction was initiated by adding 50 μL of 10 mM NADPH (freshly prepared in phosphate buffer) to give a final concentration of 1 mM NADPH in the mixture. Aliquots of 50 μL were withdrawn immediately on addition of NADPH (time 0) and 45 min later. On removal of the sample, reaction was quenched by addition of chilled methanol (100 μL). The mixture was then centrifuged at 10,000 g to remove the protein and the supernatant was analyzed by LC-MS-MS.

Liquid chromatography was performed on an Agilent® 1200 series HPLC system interfaced with a QTRAP 3200 triple quadruple mass spectrometer (Applied Biosystems, Foster City, Calif.). Instrument control and data acquisition were performed using Applied Biosystems software Analyst 1.4.2. Separation was carried out on a Phenomenex Luna® $C_{18}$ column (50×2.0 mm, 3 μM) with 10 mM ammonium formate in 0.1% formic acid (mobile phase A) and acetonitrile (mobile phase B) as eluting solvents, run on gradient mode, details of which are as follows:

| Step | Total time (min) | Mobile Phase A % | Mobile Phase B % |
|---|---|---|---|
| 0 | 0 | 98 | 2 |
| 1 | 2 | 98 | 2 |
| 2 | 8 | 2 | 98 |
| 3 | 10 | 2 | 98 |

| Step | Total time (min) | Mobile Phase A % | Mobile Phase B % |
|---|---|---|---|
| 4 | 10.2 | 98 | 2 |
| 5 | 11 | 98 | 2 |

Column temperature was maintained at 50° C., injection volume was 10 μL and flow rate 400 μL/min. The mass spectrometer was operated in the turbo spray mode with positive ion detection. The optimized instrument parameters were source temperature 650° C.; turbo spray voltage 5500 V; curtain gas ($N_2$) 10; Nebulising gas ($N_2$) 40-60; turbo ion spray gas ($N_2$) 50; collision gas (argon) medium; dwell time 200 ms.

Full scan spectra of 8-12 and cysmethynil were first obtained, after which Extracted Ion chromatogram (XIC) spectra were derived based on predicted metabolites. Metabolite peaks that had total ion current of $1 \times 10^5$ counts per second (cps) or more were shortlisted and the product ion spectra were obtained by adjusting the declustering potential (V) and collision energy (eV).

Evaluation of In Vivo Activity on Xenograft Bearing Mice

Approval for the experimental protocol was obtained from the SingHealth Institutional Animal Care and Use Committee (Application number #2011/SHS/688). HepG2 cells were grown in DMEM and 10% FBS until near confluence and then harvested after trypsinization. Cells ($1 \times 10^7$) were mixed with Matrigel® (BD Biosciences, Catalog No. 354234) to achieve 40% Matrigel in the final mixture. The cell preparation was injected subcutaneously Into the flanks of female immunodeficient SCID mice (6-8 weeks old, 20-22 g). When tumors were palpable (100-200 $mm^3$), the animals were randomly assigned to 5 groups of 8 mice each, namely (i) a control group which received vehicle IP, on alternate days; (ii) two groups that were given 75 mg/kg and 150 mg/kg cysmethynil respectively (IP, on alternate days); and (iii) two groups that received 15 mg/kg and 30 mg/kg 8-12 respectively (IP, daily). Fresh stock solutions were prepared daily or on alternate days for each dose regimen (for example, 7.5 mg/mL stock for dose of 75 mg/kg). The vehicle was ethanol-PEG400-dextrose solution as described in 5.2.1. The animals were monitored daily for changes in their general appearance, weight and tumor volume. Tumor volume was calculated using the formula: $V=4/3 (\pi \times L \times W^2)/6$. Length (L) and width (W) of the tumor were measured with a digital vernier caliper and reported to 2 decimal places. The shorter of the 2 distances was taken as width. The mice were monitored—for 25-days after which they were euthanized with $CO_2$, the tumors removed by dissection and weighed. Animals were also euthanized (before Day 25) if they showed any of the following characteristics: tumor volume $>2$ $cm^3$; tumor ulceration, infection or inflammation; ruffled fur, hunched back appearance or inappetent state; 10% or more body weight loss over 24 h or 20% body weight loss over one week moribund or premoribund state.

Statistical Analysis 242.1. Tumour volume and tumor weight data were analyzed by One-way ANOVA with Dunnett post-hoc on IBM SPSS Statistics Version 19.0 (Chicago, Ill.). p-values $<0.05$ were considered significant.

Results

Maximal Tolerated Dose of 8-12 and Cysmethynil in Balb/c Mice 8-12 was well tolerated at 10, 20 and 50 mg/kg but at 100 mg/kg, one of the 2 mice died within the 45 min observation period. The animals were monitored for the next 24 h, and during this time, no morbidity was observed. In the case of cysmethynil, it was well tolerated at all doses (20 mg/kg to 200 mg/kg) and no deaths were observed.

Pharmacokinetic Evaluation of 8-12 and Cysmethynil in Balb/c Mice

Figure 14:
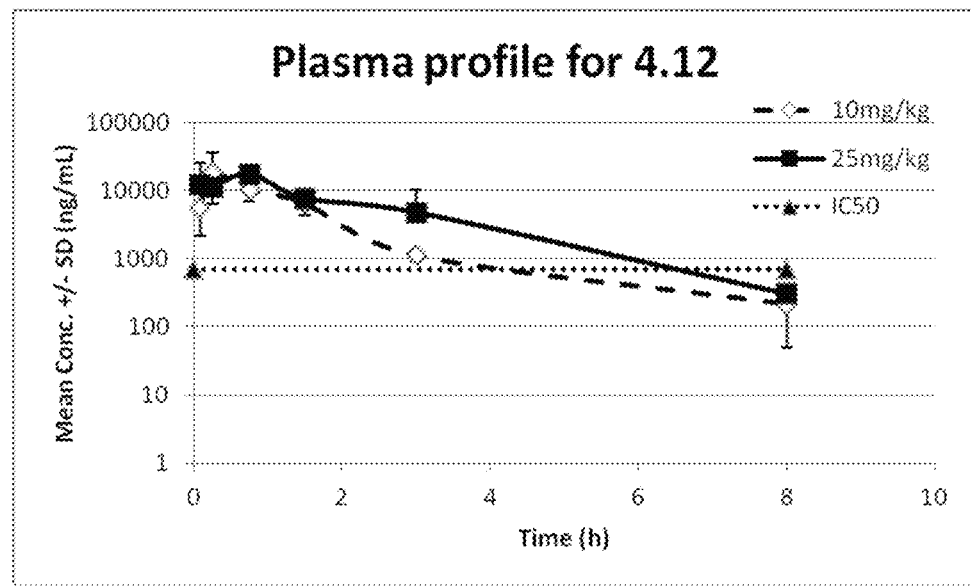
FIG. 14: Mice plasma concentrations of 8-12 at various time points. 8-12 was administered at 10 mg/kg and 25 mg/kg IP. Each data point was obtained from 3 animals.

In view of the results obtained for the maximal tolerated doses of 8-12 and cysmethynil, a decision was made to evaluate 8-12 at 10 mg/kg and 25 mg/kg, and cysmethynil at 20 mg/kg and 100 mg/kg. FIG. 14 shows the change in plasma concentration with time for the two doses of 8-12. 842 was not detected after 24 h and 48 h.

The plasma data was analyzed assuming non-compartmentalized pharmacokinetics. Table 9 lists some apparent pharmacokinetic (PK) parameters derived from this analysis.

TABLE 9

Apparent pharmacokinetic parameters of 8-12 and cysmethynil derived from WinNonLin ® software based on non-compartmental model

| Parameters | 8-12 | | Cysmethynil | |
|---|---|---|---|---|
| | 10 mg/kg | 25 mg/kg | 20 mg/kg | 100 mg/kg |
| $C_{max}$ (ug/mL)[1] | 17.9 | 17.4 | 210 | 1162 |
| $T_{max}$ (h)[2] | 0.25 | 0.75 | 0.75 | 0.75 |
| AUC all (μg · h/mL)[3] | 24.63 | 40.81 | 843 | 7692 |
| $T_{1/2}$ (h)[4] | 1.25 | 1.36 | 1.55 | 42.6 |
| Volume of Distribution[5] (mL/kg) | 721 | 1185 | 52.9 | 79.9 |
| Clearance[6] (mL/h/kg) | 400 | 604 | 23.7 | 13 |

[1]Peak concentration in plasma.
[2]Time at which peak concentrtion was observed.
[3]Area under the time-concentration curve. Indicates drug exposure
[4]Half life which is the time of for the concentration in plasma to be reducted by half.
[5]Indicates how widely compound is distributed in system.
[6]Indicates how rapidly compound is extracted from the circulation and eliminated As seen from Table 9, the pharmacokinetic parameters of 8-12 given at 10 mg/kg or 25 mg/kg did not differ markedly. The peak concentration in plasma ($T_{max}$) was achieved within an hour. 8-12 had a large volume of distribution exceeding volume of blood (ca 70 mL/kg), suggesting that it was extensively distributed into tissue compartments like muscle and fat and not restricted to the circulation by binding to plasma proteins. Its clearance from the systemic circulation was rapid and 8-12 was estimated to have a moderately short half life ($<3$ h). In view of these findings, it may be necessary to administer 8-12 more frequently to animals for the in vivo experiments if adequate tissue levels are to be achieved.

Figure 15:
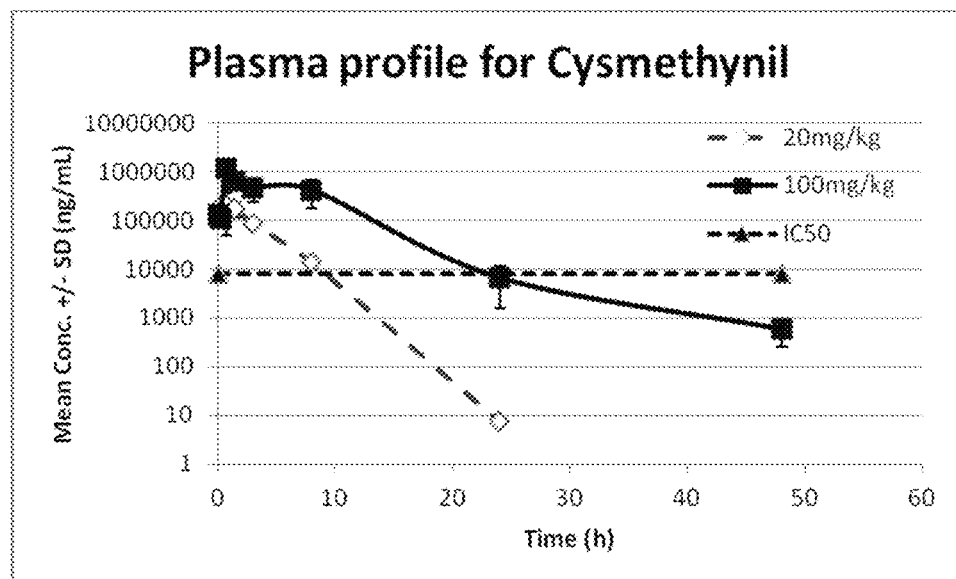
FIG. 15: Mice plasma concentrations of cysmethynil at various time points. Cysmethynil was administered at 20 mg/kg and 100 mg/kg IP. Each data point was obtained from 3 animals.

FIG. 15 shows the change in plasma concentration with time for the two doses of cysmethynil. Plasma was collected from animals dosed with 20 mg/kg up to 24 h only because cysmethynil could not be detected in plasma beyond this time. For animals dosed with 100 mg/kg, plasma collection continued up to 48 hours. The different plasma collection time points (24 h for 20 mg/kg and 48 h for 100 mg/kg) could have led to some differences in their pharmacokinetic parameters (notably the half life which was longer (4.3 h) for the higher dose compared to the lower dose (1.6 h).

The apparent pharmacokinetic parameters of 8-12 and cysmethynil were compared at 20 mg/kg and 25 mg/kg respectively. One obvious difference was noted in the volumes of distribution of the two compounds. The average volume of blood in a mouse is 70 mL/kg and volumes of distribution that are close to or less than this value indicate that the compound is confined to the blood stream, probably by plasma protein binding. Volumes of distribution that approach (or exceed) the volume of body water (700 mL/kg) indicate that the compound is distributed throughout the blood and tissues. Thus, it is deduced that cysmethynil (53 mL/kg) was largely restricted to the blood stream by plasma protein binding, whereas 8-12 (721 mL/kg) was distributed throughout body water (blood and tissues) with limited binding to plasma proteins. The clearance of the two compounds also differed. 8-12 was rapidly cleared in contrast to cysmethynil which had a slow clearance. Half lives were however comparable (<1 h) as it is determined by volume of distribution and clearance (half life=volume of distribution/clearance). A caveat on the interpretation of these results is that the plasma-time curves spanned different time periods, namely 8 h for 8-12 and 24 h for cysmethynil, and this difference could have influenced the magnitude of the pharmacokinetic values.

FIGS. 14 and 15 include a horizontal line which corresponds to the in vitro $IC_{50}$ of 8-12 (1.70 μM) and cysmethynil (22.0 μm). For both compounds, the lines were below the estimated $C_{max}$ values, which implied that plasma levels associated with antiproliferative activities were attained for both compounds.

In Vitro Metabolite Identification

Profiles of the major metabolites of 8-12 and cysmethynil were obtained by microsomal incubation followed by LC/MS/MS analysis. Based on the structures of the compounds, phase I metabolites were predicted, such as metabolites arising from hydroxylation, dihydroxylation or demethylation. Each of these metabolites would result in a characteristic molecular ion (for example +16 for hydroxylation, −14 for demethylation) and if these were found in the extracted ion chromatogram (XIC) of the compound, the MS/MS product ion spectrum (daughter spectrum) of each component was extracted. In the case of 8-12, four metabolites were proposed based on the presence of molecular ions which were not found in the microsomal control sample. The metabolites arose from mono-hydroxylation (A, MH+16), dihydroxylation (B, MH+32) and deethylation (C, MH−28). Another metabolite D had a mass difference of 30 from 8-12 and was proposed to result from hydroxylation and conversion of a terminal methyl to an aldehyde ($CH_3 \rightarrow CHO$). Table 10 lists these metabolites (A-D) and their retention times on the mass ion spectrum. The daughter spectrum of each metabolite was derived and an attempt was made to assign the fragments arising from the metabolite.

TABLE 10

Proposed metabolites of 8-12 based on LC/MS/MS analysis

| Component | Description | Molecular Ion | m/z | Retention time (min) |
|---|---|---|---|---|
| 8-12 | Parent | MH+ | 408.4 | 5.946 |
| A | Hydroxylation | MH+ + 16 | 424.2 | 5.146 |
| B | Dihydroxylation | MH+ + 32 | 440.2 | 4.572 |
| C | N-Deethylation | MH+ − 28 | 380.4 | 5.869 |
| D | Hydroxylation + oxidation of $CH_3$ to CHO | MH+ + 30 | 438.0 | 4.816 |

Figure 16:
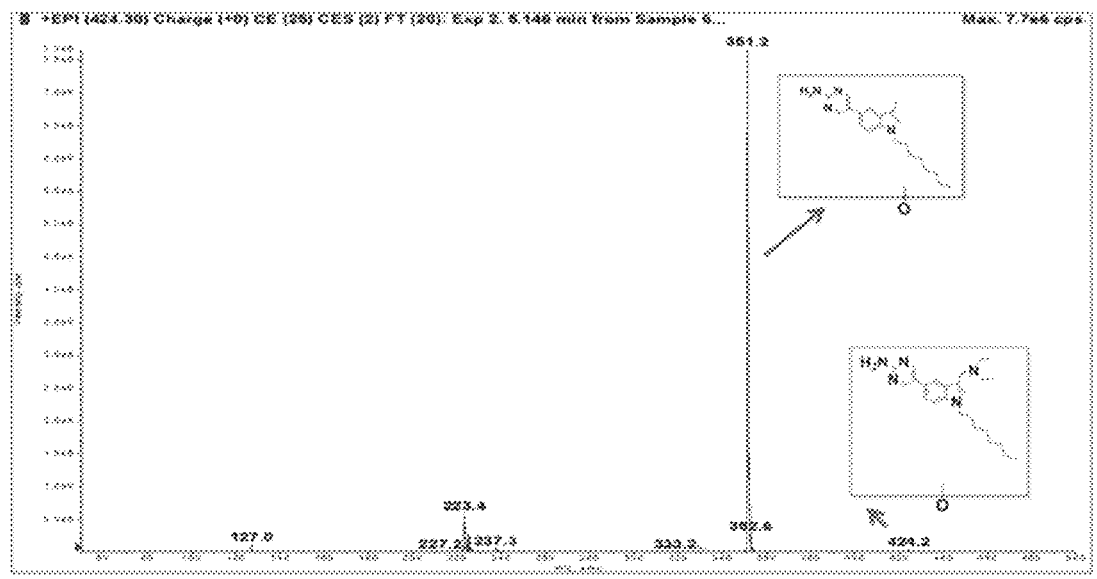
FIG. 16: Product ion spectrum of metabolite A. The "—O" symbol indicates the addition of mass 16 to the specie. Exact site of addition in molecule is not known.

FIG. 16 shows the daughter ion spectrum of the oxygenated/hydroxylated metabolite A. Loss of the diethylamino moiety gave a fragment 351.2 which retained the oxygen-containing/hydroxyl group. Further fragmentation could not reveal where the oxidation has occurred. It could have occurred on the octyl side chain or may have arisen from N-oxidation of the pyrimidine ring.

Figure 17:
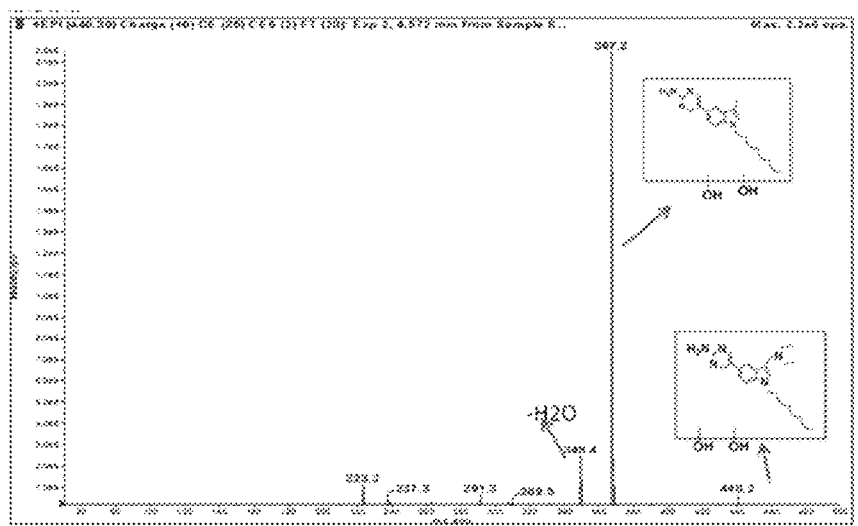
FIG. 17: Product ion spectrum of metabolite B. The "—O" symbol indicates the addition of mass 16 to the specie. Exact site of addition in molecule is not known.

In the case of metabolite B (FIG. 17), the daughter ion spectrum closely resembled that of metabolite A. The fragment with mass 367.2 was again observed and attributed to concurrent oxygenation and loss of the diethylamino side chain (367.2). However, the identity of metabolite B could not be established from the fragmentation pattern.

Figure 18:
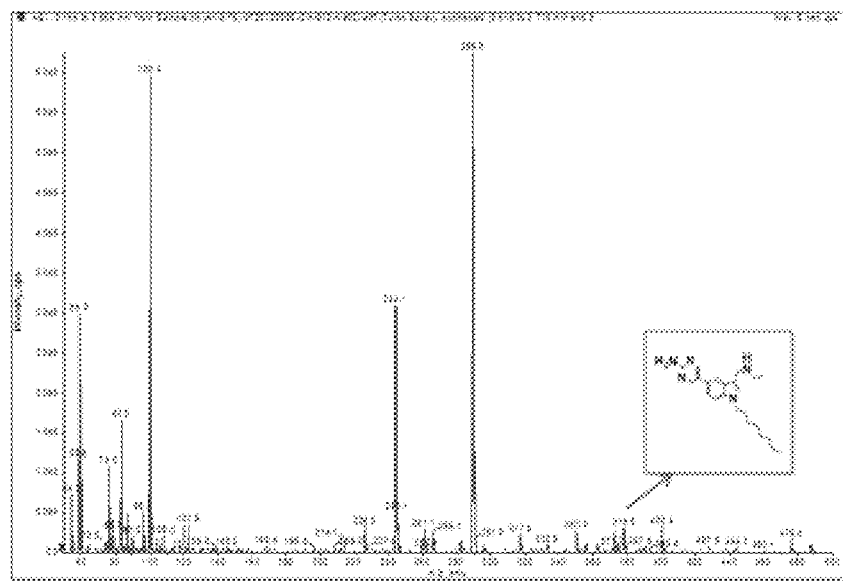
FIG. 18: Daughter ion spectra of metabolites C and D.
Figure 18:
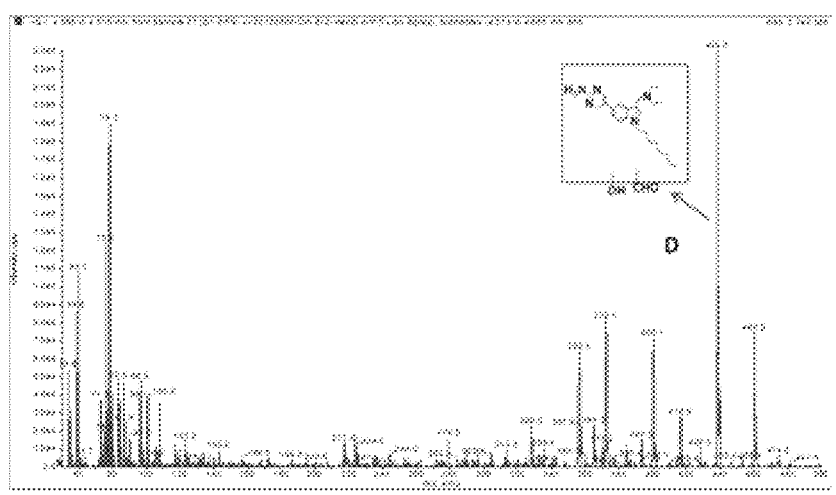
Figure 19:
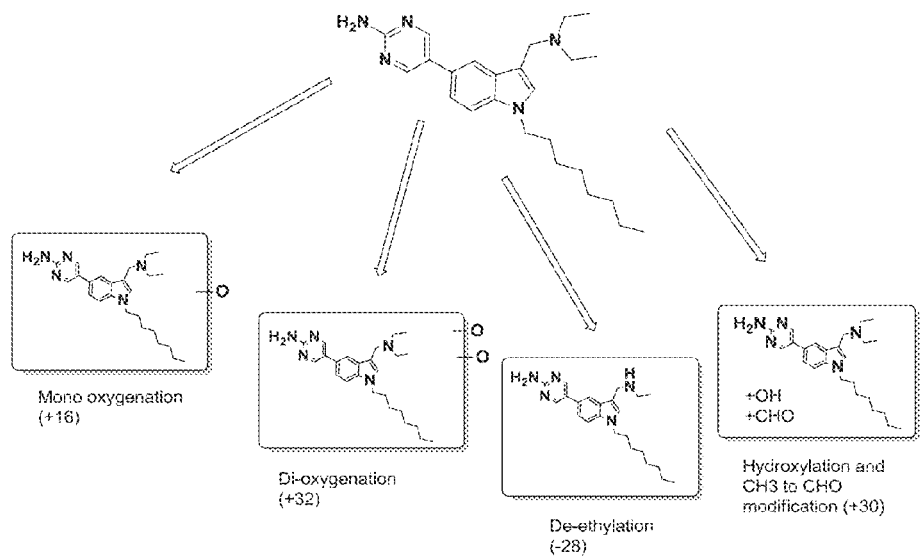
FIG. 19: Proposed metabolites of 8-12

252.1. FIG. 18 depicts the product ion spectra of metabolites C and D. No characteristic fragments could be assigned to the daughter fragments of either metabolite. It is proposed that metabolite C is due the deethylation of the diethylamino moiety. The mass of metabolite D suggested the presence of an oxygen-containing/OH group (+16) and a carbonyl containing group which may have originated from a methyl to aldehyde ($CH_3 \rightarrow CHO$) conversion. This could have occurred on the n-octyl side chain as a similar transformation had been reported for octyl-containing compounds. As metabolites C and D were observed at lower intensities (<$10^6$ cps) than A and B, they may be minor metabolites of 8-12 FIG. 19 summarizes the proposed metabolites derived from 8-12

The same procedure was used to propose the metabolites of cysmethynil. The extracted ion chromatograms of cysmethynil showed 4 mono-oxygenated/hydroxylated metabolites (A-D) at different retention times (Table 11).

TABLE 11

Proposed metabolites of cysmethynil based on LC/MS/MS analysis

| Component | Description | Molecular Ion | m/z | Retention time (min) |
|---|---|---|---|---|
| cysmethynil | Parent | MH+ | 377.3 | 8.158 |
| A | Hydroxylation | MH+ + 16 | 393.3 | 7.870 |
| B | Hydroxylation | MH+ + 16 | 393.3 | 7.580 |
| C | Hydroxylation | MH+ + 16 | 393.3 | 7.347 |
| D | Hydroxylation | MH+ + 16 | 393.3 | 6.980 |

Figure 20:
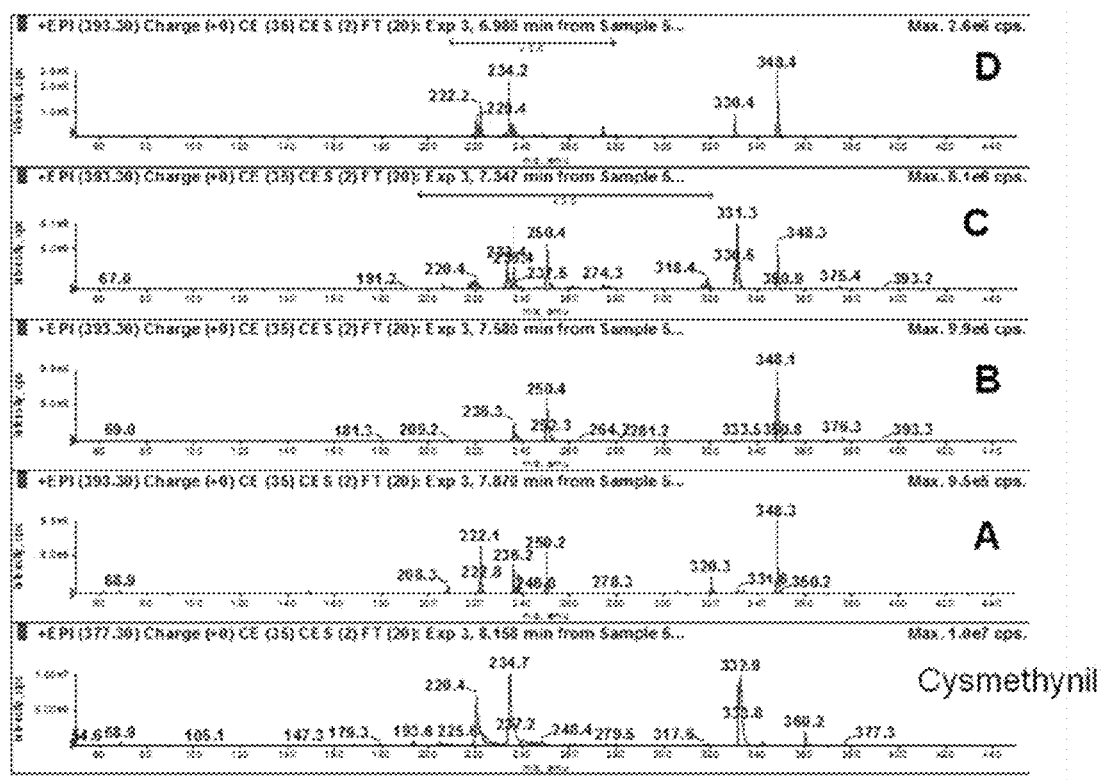
FIG. 20: Extracted ion chromatograms of m/z 393.30 (MH+16)$^+$ from microsomal incubation of cysmethynil
Figure 21:
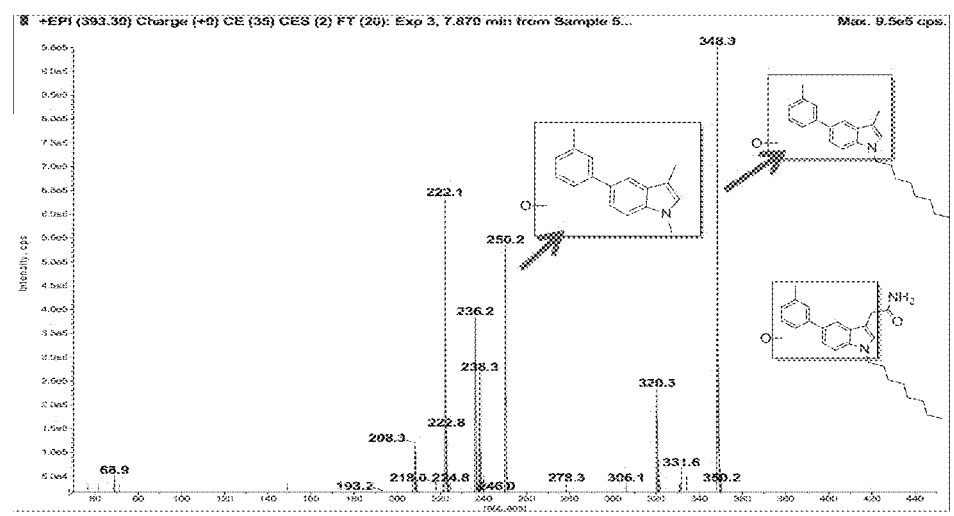
FIG. 21: MS-MS Daughter ion spectra of metabolites A-D of cysmethynil.
Figure 21:
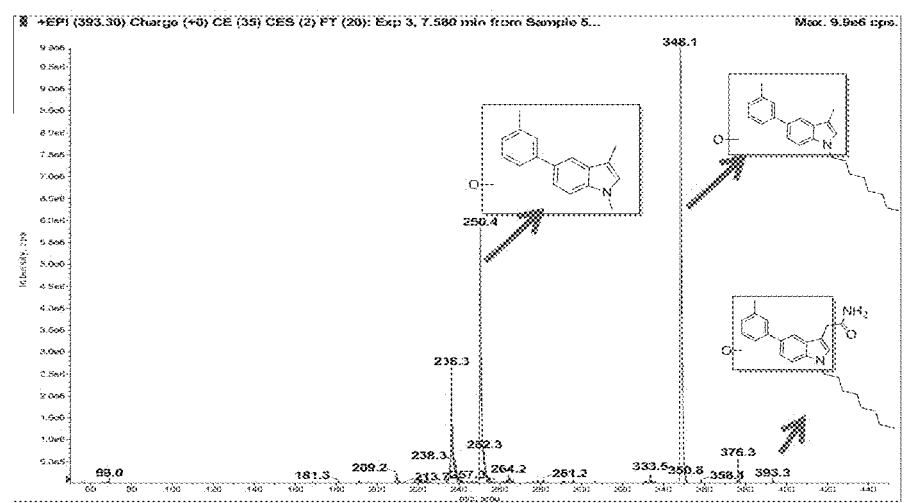
Figure 21:
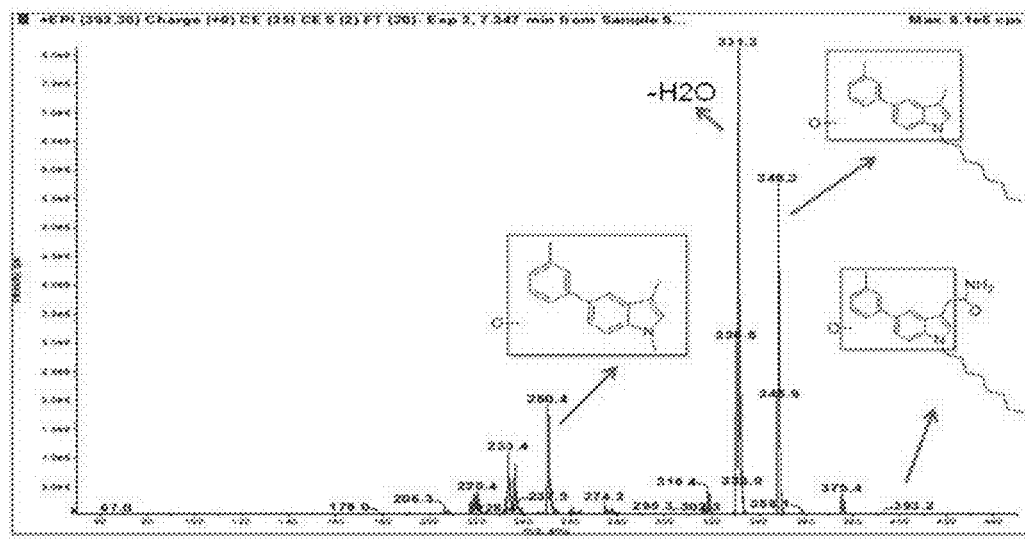
Figure 21:
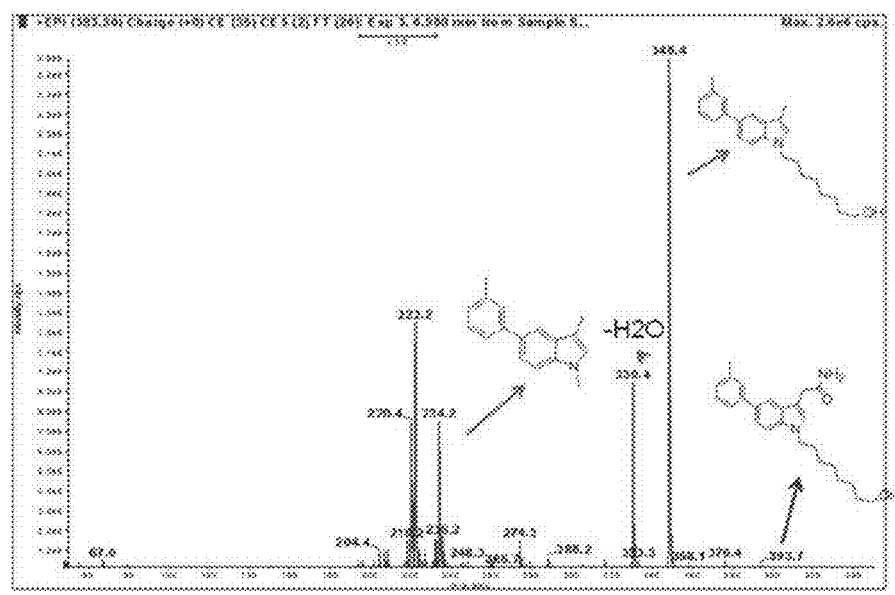
Figure 22:
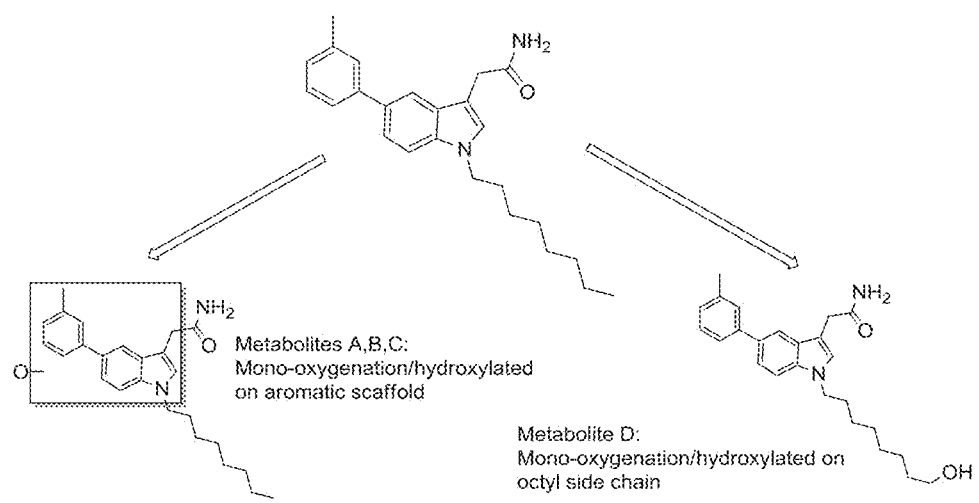
FIG. 22: Summary of metabolites derived from microsomal incubation of cysmethynil
Figure 23:
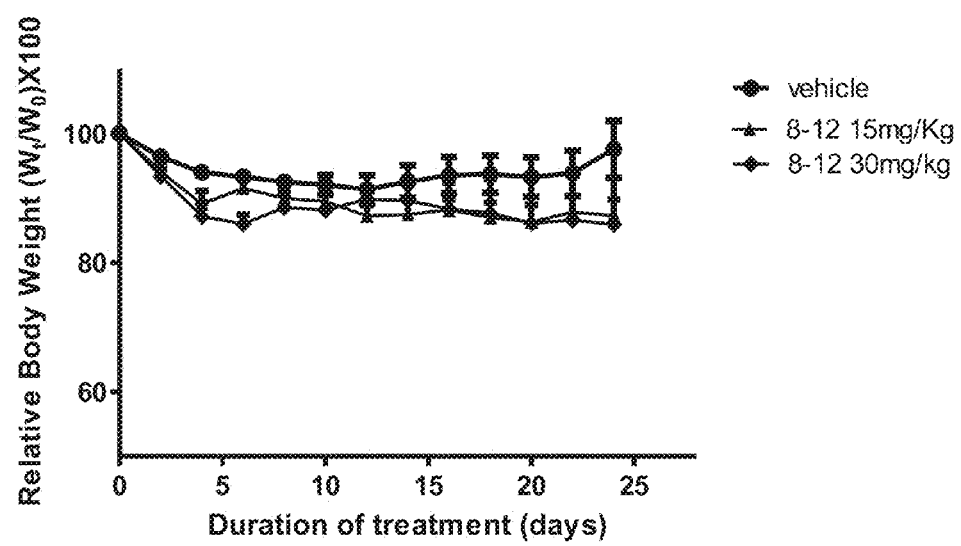
FIG. 23: Changes in body weight (grams) of xenograft-bearing mice treated with vehicle (Control), 8-12 and cysmethynil at indicated doses. Weight (Wt) was expressed as % of initial weight (Wo) at Day 0. Error bars indicate standard deviation.
Figure 23:
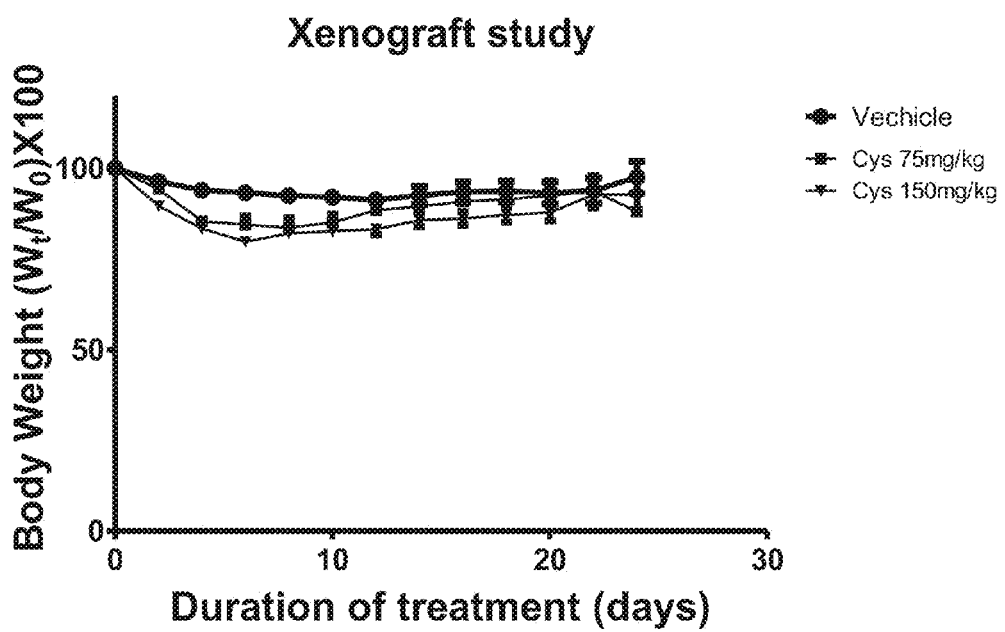

Analysis of the daughter ion spectra showed that oxygenation/hydroxylation occurred on the aromatic scaffold of metabolites A-C. These metabolites showed similar fragments arising from the loss of the amide ($CONH_2$) residue (348.3), and partial loss of the n-octyl side chain and the $CONH_2$ residue (250.2). The retention of oxygen/OH in these fragments was evident from their masses. In the case of D, the fragment with mass 348.3 was also observed in the daughter ion spectra but the mass of the fragment corresponding to partial loss of n-octyl and $CONH_2$ (234.4) was compatible with the absence of oxygen/OH in the ring scaffold. The implication was that the oxygen-containing/OH group was attached to the n-octyl side chain of metabolite D, unlike the other metabolites A-C where the OH was attached to the aromatic rings. FIG. 20 depicts the extracted ion chromatograms of the metabolites A-D and FIG. 21 shows the daughter spectra derived from the metabolites. FIG. 22 summarizes the proposed metabolites derived from cysmethynil.

Effect of 8-12 on Mice Bearing Human Hepatocellular Carcinoma HepG2 Xenografts 8-12 was dosed daily at 15 mg/kg and 30 mg/kg to xenograft-bearing mice for 25 days. These doses were less than the apparent maximal tolerated dose of 8-12 (100 mg/kg). Daily dosing was carried out because the pharmacokinetic investigation (8-12 at 10 mg/kg and 25 mg/kg) showed that 8-12 was rapidly cleared from blood. Cysmethynil was investigated at 75 mg/kg and 150 mg/kg. It was dosed on alternate days as it was cleared at a slower rate than 8-12.

Of the 8 mice that received 15 mg/kg 8-12, one animal died during the treatment period (Day 24). Three deaths were recorded in mice receiving the higher dose of 30 mg/kg 8-12 (Days 4, 8, 22). In the case of mice treated with cysmethynil, 3 of the 8 animals died for each dose regimen (Days 6, 24 for 75 mg/kg; Days 8, 10, 22 for 150 mg/kg). The control group saw 1 death which occurred on Day 23. The deaths were not anticipated, with the animals found dead in their cages overnight. None of the animals were put down due to censored events.

The body weights of the mice were monitored throughout the treatment period. As seen from FIG. 26, mice treated with 8-12 lost weight within the 1$^{st}$ week, with significant losses observed at the higher dose (30 mg/kg) on Days 5 and 7. Thereafter, the animals regained weight and no significant loss was observed by the 25$^{th}$ day. Weight loss was observed up to Day 11 for cysmethynil treated animals at both doses but like 8-12, animals showed good weight recovery by the 25$^{th}$ day.

Figure 24:
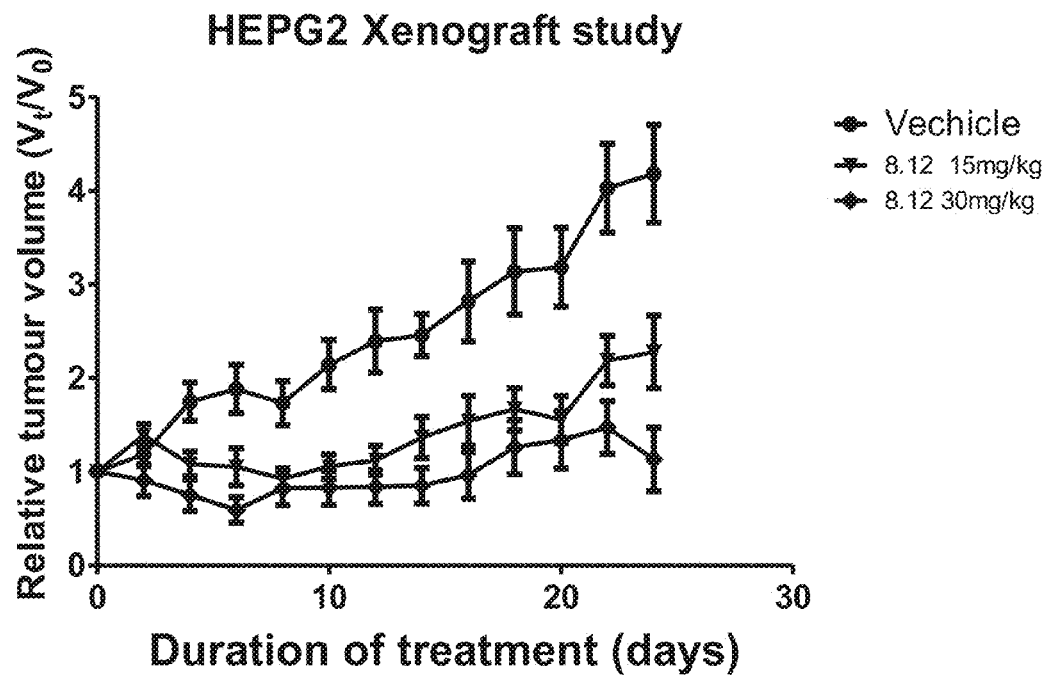
FIG. 24: Changes in relative tumour volume of xenograft-bearing mice treated with vehicle (Control) and 8-12 at 15 mg/kg and 30 mg/kg. Relative tumor volume=(volume at nth day/volume at Day 0)×100%. Reduction in tumor volume was significant from Day 5 and Day 7 onwards for animals dosed with 30 mg/kg and 15 mg/kg respectively (p<0.05, 1-way ANOVA, Dunnett post-hoc). On Days 9 (30 mg/kg) and 15 (15 mg/kg), relative tumour volumes were not significantly different (p>0.05).

Evidence of in vivo efficacy of 8-12 was derived from the change in tumor volume in treated animals. FIG. 24 shows the time dependent changes in relative tumor volumes of animals dosed with 8-12. Significant reduction in tumor volume was evident from Day 5 onwards for animals receiving 30 mg/kg and Day 7 onwards for animals receiving 15 mg/kg (p<0.05, 1-way Anova, Dunnett post-hoc). There were aberrations on Days 9 (30 mg/kg) and 15 (15 mg/kg) where the reductions in volumes were not statistically significant.

Figure 25:
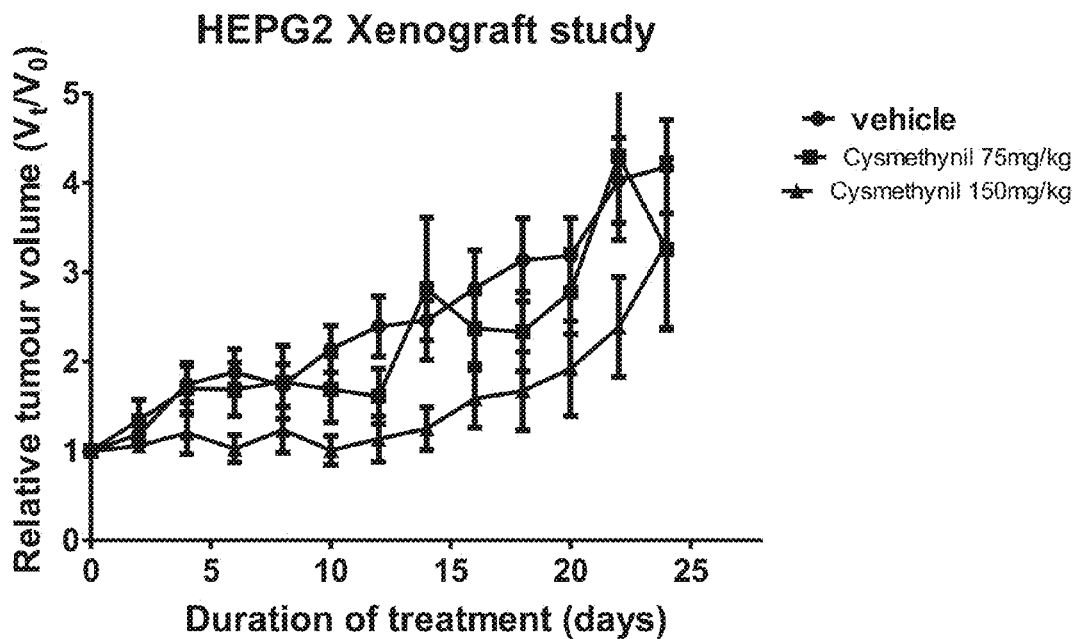
FIG. 25: Changes in relative tumour volume of xenograft-bearing mice treated with vehicle (Control) and cysmethynil at 75 mg/kg and 150 mg/kg. Relative tumor volume= (volume at nth day/volume at Day 0)×100%. Reduction in tumor volume was significant on Day 11 and Day 13 for animals treated with 150 mg/kg. (p<0.05, 1-way ANOVA, Dunnett post-hoc)

FIG. 25 shows the time dependent changes in relative tumor volumes of animals dosed with cysmethynil. The reductions in tumor volume were significant for 150 mg/kg treated animals on Days 11 and 13. Thereafter, tumor volumes increased steadily up to the end of the treatment period. Although smaller tumor volumes were recorded for animals receiving 75 mg/kg, reductions were not statistically significant.

Figure 26:
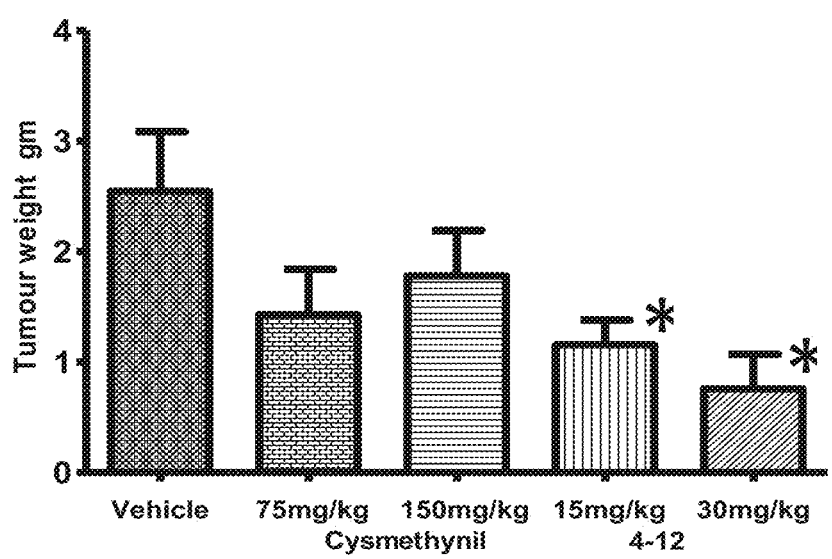
FIG. 26: Weights of tumors excised from control and treated animals after 25 days treatment. * indicates significant reduction in weight of tumor compared to control. (p<0.05, 1-way ANOVA, Dunnett post-hoc).

After 25 days, the tumors were excised and weighed. As seen in FIG. 26, reductions in tumor volumes were observed for all treatments but only those derived from 8-12 treated animals showed significant weight loss compared to control (p=0.024 for 15 mg/kg, p=0.01 for 30 mg/kg).

Discussion

In earlier reports, cysmethynil was investigated at 100 mg/kg and 200 mg/kg in mice bearing xenografts induced by prostate cancer PC3 and hepatocellular carcinoma HepG2 cells. It was well tolerated (dosing by IP administration, alternate days for 28 days) and a reduction in tumor volume was observed at the end of the study period. The same protocol was followed in this chapter except that cysmethynil was administered at lower doses of 75 mg/kg and 150 mg/kg. Reductions in tumor volumes and (final) tumor weights were noted in treated animals, with greater reductions observed in animals receiving the higher dose. However, tumor volume reductions were statistically significant only for animals on the higher dose (150 mg/kg) and for a short period midway (Days 13, 15) in the treatment period. As deaths were observed in the cysmethynil treated animals (3 deaths out of 8 mice, at both dose regimens), the smaller animal cohort may have affected the statistical analysis. Taken together, cysmethynil is generally well tolerated in healthy mice. Its maximal tolerated dose exceeded 100 kg/kg and in xenograft bearing animals, those that survived with reduction in tumor volumes were healthy and maintained their weights after an initial period of weight loss.

Compared to cysmethynil, 8-12 demonstrated greater efficacy on the xenograft model. It reduced tumor volumes at all test doses (15 mg/kg, 30 mg/kg), the reductions were sustained and statistically significant from Days 5 and 7 to the end of the study period, and there were indications of dose dependency in tumor size reductions. The apparent maximal tolerated dose of 8-12 was 100 mg/kg but its in vivo effects were demonstrated at lower concentrations (15 mg/kg, 30 mg/kg). At these doses, animals remained healthy and maintained their weights after an initial period of weight loss.

The potency and efficacy of 8-12 as a potential anti-cancer agent has been demonstrated in this report. 8-12 inhibited Icmt and curtailed proliferation of malignant cells at low micromolar/submicromolar concentrations. In vivo, its efficacy on the xenograft model was evident at 15 mg/kg. Aside from these desirable attributes, lead compounds must demonstrate drug-like properties if they are to progress further in development. A back-of-the-envelopment assessment of 8-12 based on the widely cited Rule of five (Ro5) criteria for drug-likeness shows that it passes muster. 8-12 has a molecular weight of 407.3, 2 hydrogen (H)-bond donor and 5H-bond acceptor groups. Its ClogP (6.6) is out of the Ro5 range, but as it has protonable groups, its lipophilicity would vary with pH and in this context, log D may be a better predictor. Ideally, log $D_{74}$ should fall within 1 and 3 to achieve a good balance of solubility and permeability for oral absorption. The estimated log $D_{7.4}$ of 8-12 (3.54) marginally exceeded the optimal range. The polar surface area of 8-12 was estimated to be 60 Å$^2$ which is near optimal for compounds targeted for oral administration. 8-12 has a high count of rotatable bonds (15) which exceeds exceeding the threshold (<10) for good bioavailability in compounds.

In order to go beyond these theoretical assessments of drug-like character, detailed physicochemical characterization of 8-12 has been undertaken. Properties investigated were solubility, permeability and aggregate forming tendency. The results are summarized in Table 12 with values obtained for cysmethynil included for comparison.

TABLE 12

Summary of physicochemical and in vitro metabolic data of 8-12 and cysmethynil

|  | 8-12 | Cysmethynil |
| --- | --- | --- |
| ClogP[1] | 6.6 | 7.0 |
| Log $D_{7.4}$[1] | 3.5 | 6.9 |
| Solubility (μM)[2] | 155.9 (±6.4) | 1.14 (±0.1) |
| PAMPA $P_e$ (×10$^{-6}$ cm/s)[2] | 14.2 (±1.4) | Nil[3] |
| Dynamic light scattering count rate (kcps)[4] at concentrations of |  |  |
| 10 μM | 53.3 | 164.0 |
| 1 μM | 24.5 | 22.6 |
| Estimated Half-life (min) from in vitro rat microsomes | 11.3 (±0.4) | 44.8 (±8.0) |
| Estimated Intrinsic Clearance (μL/min/mg) from in vitro rat microsomes | 204.0 (±9.0) | 53.6 (±9.0) |

[1]Estimated with ChemDraw Ultra 12.0 (ClogP) and ACD/Labs 12.0 (log D 7.4).
[2]Determinations were made at pH 7.4, 24 h (solubility) or 16 h (PAMPA $P_e$) agitation. Mean (SD) of 3 separate determinations.
[3]Could not be determined under existing experimintal conditions.
[4]Mean count rates (kilocount per sec) from 3 separate determinations at 10 μM or 1 μM test compound (1% DMSO, potassium phosphate buffer 5 mM pH 7.4).

Solubility was determined on Multiscreen® solubility filter plates from Millipore in phosphate buffer pH 7.4 (1% v/v DMSO) at 25° C. with agitation for 24 h. Permeabilities were determined by the parallel artificial membrane permeability assay (PAMPA) at pH7.4 with lecithin-dodecane as the simulated cellular barrier. At pH 7.4, 8-12 was at least 100× more soluble than cysmethynil. Its solubility (156 μM or 64 μg/mL) was close to the minimum accepted drug solubility (50 μg/mL) for a compound with "average"

potency and permeability. Without wishing comment on the clinical potency of 8-12, its permeability as assessed by effective permeability (Pe) was $14.2 \times 10^{-6}$ cm/s exceeded that of verapamil ($10.2 \times 10^{-6}$ cm/s, determined under similar conditions) which is normally used as a high permeability standard. The higher $P_e$ of 8-12 suggests above average permeability. The permeability of cysmethynil could not be determined by the present method because its low solubility limited its analysis in the donor and receiving compartments of the PAMPA plates.

Table 12 includes determinations of dynamic light scattering by 8-12 and cysmethynil at two concentrations. These determinations were undertaken to assess the aggregate-forming tendencies of the compounds and they were prompted in part by the amphipathic nature of both compounds (lipophilic n-octyl side chain combined with polar amide/tertiary amine). These features may promote formation of micelles and of greater concern, soluble colloidal aggregates which are widely associated with promiscuous behavior, such as non-specific inhibition of enzymes. Compounds that form soluble or colloidal aggregates normally exist as particles of 30-1000 nm in diameter which are detectable by light scattering. Aggregators exhibit significant increases in aggregate formation with relatively small increases (2-3 fold) in concentration. As seen from Table 12, cysmethynil caused a 7 fold increase in light scattering when concentration was increased from 1 μM to 10 μM whereas 8-12 caused a 2-fold increase for the same change. 8-12 may thus have a lower tendency to form aggregates compared to cysmethynil.

A preliminary assessment of the pharmacokinetics of 8-12 and cysmethynil was carried out in mice to assist in the dosing schedule for the in vivo xenograft experiments. Both compounds have broadly similar half-lives but very different volumes of distribution and clearance values. The more lipophilic and poorly permeable cysmethynil had a smaller volume of distribution suggestive of marked plasma protein binding. The more permeable and water soluble 8-12 was widely dispersed in body water and tissues and thus have a larger volume of distribution. Further support for the different pharmacokinetic profiles of 8-12 and cysmethynil came from investigations on the metabolic stabilities of these compounds when incubated with rat microsomes. Both compounds were deemed to be metabolically more stable than midazolam which was determined under similar conditions. Half lives and intrinsic clearance values estimated from the incubation period (45 min) supported the view that 8-12 was more rapidly cleared than cysmethynil. The metabolites arising from rat microsomal metabolism were analyzed and some marked differences were evident. Cysmethynil was largely mono-hydroxylated on the aromatic scaffold and the n-octyl chain, whereas hydroxylation of 8-12 was confined to the n-octyl side chain. There was evidence of N-dealkylation of the tertiary amino side chain.

Summary

The findings herein have provided evidence that 8-12 was effective in reducing tumor xenografts induced in mice. Some insight was obtained into the pharmacokinetic characteristics of 8-12. It was found to have a large volume of distribution in treated mice, to be rapidly cleared from the systemic circulation and to possess a relatively short half life of <1 hour. Metabolites of 8-12 predicted from rat microsomal incubation experiments point to the presence of hydroxylated metabolites, an N-dealkylated metabolite and a less well defined oxygenated metabolite.

The invention claimed is:

1. A 1,3,5-substituted indole wherein:
    the substituent at position 1 is a $C_6$ to $C_{12}$ alkyl group;
    the substituent at position 3 is $CH_2NR^1R^2$ wherein $R^1$ is H or $C_1$ to $C_3$ alkyl, $R^1$ being optionally substituted with —OH, —SH, —$NH_2$ or NHalkyl, wherein alkyl is a $C_1$ to $C_4$ alkyl group, and $R^2$ is $C_1$ to $C_3$ alkyl or $(CH_2)_n$ bonded to position 2 of the indole, wherein n is 1, 2 or 3; and
    the substituent at position 5 is either an optionally substituted nitrogen containing heteroaromatic ring or an aminosulfonylphenyl group or an alkylsulfonylphenyl group.

2. The indole of claim 1 wherein the substituent at position 1 is a straight chain alkyl group.

3. The indole of claim 1 wherein the substituent at position 1 is octyl.

4. The indole of claim 1 wherein $R^1$ and $R^2$ are both ethyl.

5. The indole of claim 1 wherein $R^1$ is H or Me and $R^2$ is $(CH_2)_2$ bonded to position 2 of the indole.

6. The indole of claim 1 wherein the substituent at position 5 is a 6-membered heteroaromatic ring containing no heteroatoms other than N.

7. The indole of claim 6 wherein the substituent position 5 contains 1 or 2 ring nitrogen atoms.

8. The indole of claim 7 wherein the substituent at position 5 is 2-aminopyrimidine-5-yl.

9. The indole of claim 1 having lipophilicity (log D at pH 7.4) of less than about 5.

10. The indole of claim 1 having an aqueous solubility of greater than about $10^{-4}$ M at pH 7.4.

11. The indole of claim 1 having an $IC_{50 MDA-MB-231}$ of less than about 6 μM.

12. The indole of claim 1 having an $IC_{50 PC3}$ of less than about 6 μM.

13. A method if inhibiting Icmt activity comprising administering an indole according to claim 1.

14. A method of inhibiting oncogenesis comprising administering an indole according to claim 1.

15. A method of treating a cancer comprising administering to a patient in need thereof a therapeutically effective quantity of a compound according to claim 1, wherein the cancer is selected from liver cancer, prostate cancer, pancreas cancer, breast cancer, lung cancer, colon cancer, glioblastoma/brain cancer, melanoma, sarcoma, leukemia and cervical cancer.

16. A composition for treatment of cancer comprising a compound according to claim 1 and one or more pharmaceutically acceptable carriers, diluents or adjuvants, wherein the cancer is selected from liver cancer, prostate cancer, pancreas cancer, breast cancer, lung cancer, colon cancer, glioblastoma/brain cancer, melanoma, sarcoma, leukemia and cervical cancer.

17. A compound according to claim 1 when used for one or more of inhibiting knit activity, inhibiting oncogenesis and treating cancer, wherein the cancer is selected from liver cancer, prostate cancer, pancreas cancer, breast cancer, lung cancer, colon cancer, glioblastoma/brain cancer, melanoma, sarcoma, leukemia and cervical cancer.

18. A compound according to claim 1 for use in therapy of cancer, wherein the cancer is selected from liver cancer, prostate cancer, pancreas cancer, breast cancer, lung cancer, colon cancer, glioblastoma/brain cancer, melanoma, sarcoma, leukemia and cervical cancer.

* * * * *